(12) United States Patent
Vermeulin et al.

(10) Patent No.: US 7,160,923 B1
(45) Date of Patent: *Jan. 9, 2007

(54) POLYAMINE ANALOGUES AS THERAPEUTIC AND DIAGNOSTIC AGENTS

(75) Inventors: Nicolaas M. J. Vermeulin, Woodinville, WA (US); Christine L. O'Day, Mountlake Terrace, WA (US); Heather K. Webb, Seattle, WA (US); Mark R. Burns, Shoreline, WA (US); Donald E. Bergstrom, West Lafayette, IN (US)

(73) Assignee: MediQuest Therapeutics, Inc., Bothell, WA (US)

( * ) Notice: Subject to any disclaimer, the term of this patent is extended or adjusted under 35 U.S.C. 154(b) by 749 days.

This patent is subject to a terminal disclaimer.

(21) Appl. No.: 09/713,512

(22) Filed: Nov. 14, 2000

Related U.S. Application Data

(63) Continuation of application No. 09/341,400, filed as application No. PCT/US98/14896 on Jul. 15, 1998, now Pat. No. 6,172,261.

(60) Provisional application No. 60/052,586, filed on Jul. 15, 1997, provisional application No. 60/065,728, filed on Nov. 14, 1997, provisional application No. 60/085,538, filed on May 15, 1998.

(51) Int. Cl.
*A61K 31/27* (2006.01)
*A61K 31/18* (2006.01)
*A61K 31/165* (2006.01)
*A61K 31/17* (2006.01)
*A61K 31/34* (2006.01)

(52) U.S. Cl. .......... 514/626; 514/311; 514/365; 514/378; 514/423; 514/445; 514/471; 514/481; 514/596; 514/602; 514/603; 514/616; 514/617; 514/625; 544/144; 548/200; 548/243; 548/325.1; 548/536; 549/479; 560/157; 564/48; 564/80; 564/83; 564/84; 564/86; 564/161; 564/180; 564/197

(58) Field of Classification Search .......... 514/423, 514/626, 311, 365, 378, 445, 471, 431, 596, 514/602, 603, 616, 617, 625; 548/536, 200, 548/248, 325.1; 564/197, 48, 80, 83, 84, 564/86, 161, 180; 544/144; 549/479; 560/157
See application file for complete search history.

(56) References Cited

U.S. PATENT DOCUMENTS

| | | | |
|---|---|---|---|
| 4,309,442 A | 1/1982 | Bey et al. | 424/319 |
| 4,774,339 A | 9/1988 | Haugland et al. | 548/405 |
| 4,818,770 A | 4/1989 | Weinstein et al. | 514/564 |
| 5,187,288 A | 2/1993 | Kang et al. | 548/110 |
| 5,248,782 A | 9/1993 | Haugland et al. | 548/110 |
| 5,252,714 A | 10/1993 | Harris et al. | 530/391.9 |
| 5,274,113 A | 12/1993 | Kang et al. | 548/405 |
| 5,433,896 A | 7/1995 | Kang et al. | 252/700 |
| 5,451,663 A | 9/1995 | Kang et al. | 530/367 |
| 5,656,671 A | 8/1997 | Bergeron, Jr. | 514/674 |

FOREIGN PATENT DOCUMENTS

| | | |
|---|---|---|
| JP | 2-266858 A | 10/1990 |
| JP | 02 256656 | 1/1991 |
| JP | 09235271 A | 9/1997 |
| WO | WO 8502769 A | 7/1985 |
| WO | WO 9100853 | 1/1991 |
| WO | WO 9214709 A | 9/1992 |
| WO | WO 9521612 A | 8/1995 |
| WO | WO 9622962 A | 8/1996 |
| WO | WO 9638464 A | 12/1996 |
| WO | WO 9903823 | 1/1999 |
| WO | WO 0034226 | 6/2000 |
| WO | WO 0046187 | 8/2000 |

OTHER PUBLICATIONS

Alhonen-Hongisto, L. et al. (1980). "Intracellular Putrescine Deprivation Induces Uptake of the Natural Polyamines and Methylglyoxal Bis(Guanylhydrazone)," *Biochem J* 192:941-945.

Alhohen-Hongisto, L. et al. (1985). "Tumourigenicity, Cell-Surface Glycoprotein Changes and Ornithine Decarboxylase Gene Pattern in Ehrlich Ascites-Carcinoma Cells," *Biochem J* 229:711-715.

Aramaki, Y. et al. (1986). "Chemical Characterization of Spider Toxin, JSTX," *Proc Japan Acad 62, Ser.B:* 359-362.

Asami, T. et al. (1989). "Acylpolyamines Mimic the Action of Joro Spider Toxin (JSTX) on Crustacean Muscle Glutamate Receptors," *Biomedical Res* 10:185-189.

Bardocz, S. et al. (1993) "Polyamines in food; Implication for Growth and Health," *J Biochem Nutr* 4:66-71.

Blagbrough, I.S. et al. (1998). "Practical Synthesis of Unsymmetrical Polyamine Amides,".

(Continued)

Primary Examiner—Peter O'Sullivan
(74) Attorney, Agent, or Firm—Connolly, Bove, Lodge & Hutz, LLP

(57) ABSTRACT

Novel inhibitors of polyamine transport having inhibition constants two orders of magnitude lower than those of known compounds are disclosed. These polyamine analogues are useful pharmaceutical agents for treating diseases where it is desired to inhibit polyamine transport or other polyamine binding proteins, for example cancer and post-angioplasty injury. Novel chemical synthetic methods to obtain polyamine analogues are disclosed, including the production of a combinatiorial polyamine library. These approaches yield analogues with desirable activities both for diagnostic and research assays and therapy. The assays of the invention are useful for high throughput screening of targets in the discovery of drugs that interact with the polyamine system.

49 Claims, 38 Drawing Sheets

OTHER PUBLICATIONS

Bogle, R.G. et al. (1994). "Endothelial Polyamine Uptake: Selective Stimulation by L-arginine Deprivation," *Am J Physiol* 266:C776-C783.

Carrington, S. et al. (1996). "Inhibition of growth of B16 Murine Melanoma Cells by Novel Spermine Analogs,"*Pharm Sci* 2(1):25-27.

Chamaillard, L. et al. (1997). "Polyamine Deprivation Prevents the Development of Tumor-Induced Immune Supression," *Br J Cancer* 76:365-370.

Chao, J. et al (1997). "N1-Dansyl-Spermine and N1-(n-octanesulfonyl)-Spermine, Novel Glutamate Receptor Antagonists: Block and Permeation of N-Methyl-D-Aspartate Receptors," *Mol Pharmacol* 51(5):861-871.

Dhainaut et al. (1996). "New Purines and Purine Analogs as Modulators of Multidrug Resistance," *J Med Chem* 39:4099-4108.

DiPasquale, A. et al. (1978). "Epidermal Growth FActor Stimulates Putrescine Transport and Ornithine Decarboxylase Activity in Cultures Human Fibroblast,"*Exp Cell Res* 116:317-323.

Felshow, D.M. et al. (1997). "Selective Labeling of Cell-Surface Polyamine-Binding Proteins on Leukemic and Solid-Tumor Cell Types Using a New Polyamine Photoprobe," *Biochem J* 328(3):889-895.

Goodnow Jr., R., et al., "*Synthesis of Glutamate Receptor Antagonist Philanthotoxin-433 (PhTX-433) and its Analogs*," Tetrahedron Lett., (1990) 46(9):3267-86.

Green, A.C. et al. (1996). "Polyamine Amides are Neuroprotective in Cerebellar Granule Cell Cultures Challenged with Excitatory Amino Acids," *Brain Research* 717/1-2:135-146.

Ha, H.C. et al., "*The Role of Polyamine Catabolism in Polyamine Analogue -Induced Programmed Cell Death*," Proc. Natl. Acad. Sci., (1997) 94:11557-62.

Hayashi, S. et al. (1996). "Ornithine Decarboxylase Antizyme: A Novel Type if Regulatory Protein," *TIBS* 21:27-30.

Heller, J.S. et al. (1976). "Induction of a Protein Inhibitor to Ornithine Decarboxylase by the End Products of Its Reaction," *Proc Natl Acad Sci USA* 73:1858-1862.

Janne, J. et al. (1978). "Polyamines in Rapid Growth and Cancer," Biochim Biophys Acta 473:241-293.

Karahalios, P. et al., "*The Effect of Acylated Polyamine Derivative on Polyamine Uptake Mechanism, Cell Growth, and Polyamine Pools in Escherichia Coli, and the Pursuit of Structure/Activity Relationships*," Eur. J. Biochem., (1998) 251:998-1004.

Khan, N., Quemener, V. et al. (1994). "Characterization of Polyamine Transport pathways", in *Neuropharmaacology of Polyamines* (Carter, C., ed.), Academic, San Diego, pp. 37-60.

Kossorotov, A. et al. (1974). "Regulatory Effects of Polyamines on Membrane-Bound Acetylcholinesterase," *Biochem J* 144:21-27.

Krapcho, A.P. et al (1990). "Mono-Protected Diamines. N-tert-butoxylcarbonyl-α,ω-Alkanediamines from α,ω-Alkanediamines," *Syn Comm* 20:2559-2564.

Leveque, J. et al (1998). "The Gastrointestinal Polyamine Source Depletion Enhances DFMO induced Polyamine Depletion in MCF-7 Human Breast Cancer Cells In Vivo," *Anticancer Res* 18:2663-3668.

Li, Y. et al. (1997). "Comparative Molecular Field Analysis-Based Predictive Model of Structure-Function Relationships of Pilyamine Transport Inhibitors in L1210 Cells," *Cancer Res* 57:234-239.

Matsufuji, S. et al. (1996). "Reading Two Bases Twice: Mammalian Antizyme Frame Shifting in Yeast," *EMBO Journal* 15:1360-1370.

Matthews, H.R. (1993). "Polyamines, Chromatin Structure and Transription," *BioAssays* 15:561-566.

Moulinoux, J-P. et al. (1991). "Biological Significance of Circulating Polyamines in Oncology," Cell Mol Biol 37:773-783.

Moulinoux, J.P. et al. (1991). "Inhibition of growth of the U-251 Human Glioblastoma in Nude Mice by Polyamine Deprivation," *Anticancer Res* 11:175-180.

Moya, E. et al. (1994). "Synthesis and Neuropharmacological properties of Arthropod Polyamine Amide Toxins," *Neuropharmacology of Polyamines* (Carter, C., ed.), Academic, San Diego, pp. 167-184.

Murakami, Y. et al. (1992). "Ornithine Decarboxylase Is Degraded be the 26S Proteosome Without Ubiquitination," *Nature* 360:597-599.

Persson, L. et al. (1998). "Curative Effect of d,1-2-Difluoromethylornithine on Mice Bearing Mutant L1210 Leukemia Cells Deficient in Polyamine Uptake," *Cancer Res* 48:4807-4811.

Pohjanpelto, P. (1976). "Putrescine Transport is Greatly Increased in Human Fibroblasts Initiated to Prolifarete," *J Cell Biol* 68:512-520.

Porter, C.W. et al. (1984). "Aliphatic Chain Length Specificity of the Polyamine Transport System in Ascites L1210 Leukemia Cells," *J Cancer Res* 44:126-128.

Qaraw, M. et al. (1997). "Optimization of the MMT Assay for B16 Murine Melanoma Cells and Its Application in Assessing Growth Inhibition by Polyamines and Novel Polyamine Conjugates," *Pharm Sci* 3(5/6):235-239.

Quemener, V. et al. (1992). "Polyamine Deprivation Enhances Antitumoral Efficacy of Chemotheraphy," *Anticancer Res* 12:1447-1454.

Raditsch, M. et al. (1996). "Polyamine Spider Toxins and Mammalian N-Methyl-D-Aspartate Receptors. Structural Basis for Channel Blocking and Binding of Argiotoxin 636," *Eur J Biochem* 240:416-426.

Ransom, R.W. et al. (1988). "Cooperative Modulation of [3H]MK-801 Binding to the N-Methyl-D-Aspartate Receptor_Ion Channel Complex by L-Glutamate, Clycine, and Polyamines," *J Neurochem* 51:830-836.

Russell, D. et al. (1968). "Amine Synthesis in Rapidly Growing Systems: Ortithine Decarboxylase Activity in Generating Rat Liver, Chick Embryo, and Various Tumors," *Proc Natl Acad Sci USA* 60:1420-1427.

Sarhan, S. et al. (1989). "The gasrointestial Tract as Polyamine Source for Tumor Growth," *Anticancer Res* 9:215-224.

Scalabrino, G. et al. (1981). "Polyamines in Mammalian Tumors. Part 1," *Adv Cancer Res* 35:151-268.

Scalabrino, G. et al. (1982). "Polyamines in Mammalian Tumors. Part 11," *Adv Cancer Res* 36:1-102.

Schechter, P.J. et al. (1987). "Inhibition of Polyamine Metabolism Biological Significance and Basis for New Therapies," McCann, P.P. et al., eds; pp. 345-364.

Seiler, N. (1987). "Functions of Polyamine Acetylation," *Can Pharmacol* 65:2024-2035.

Seiler, N. et al., "Polyamine Transport In Mammalian Cells," Int. J. Biochem., (1990) 23(3):211-8.

Seiler, N. (1995). "Polyamine Oxydase, Properties and Functions," *Progress in Brain Res* 106:333-344.

Seiler, N. et al. (1998). "Polyamine Sulfonamides with NMDA Antagonist Properties Are Potent Calmodulin Antagonists and Cytotoxic Agents," *Int J Biochem Cell Biol* 30(3):393-406.

Sugiyama, S. et al. (1996). "Crystal Structure of PotD, the Primary Receptor of the Polyamine Transport System in *Escherichia Coli*," *J Biol Chem* 271:9519-9525.

Suzuki, T. et al. (1994). "Antizyme Protects Against Abnormal Accumulation and Toxicity of Polyamines in Ornithine Decarboxylase-Overproducing Cells," *Proc Natl Acad Sci USA*.

Tabor, H. et al. (1976). "1,4-Diaminobutrane (putrescine), Spermidine, and Spermine," *Ann Rev Biochem* 45:285-306.

Tomitori, H. et al. (1999). "Identification of a Gene for a Polyamine Transport Protein in Yeast," *J Biol Chem* 274:3265-3267.

Tsubokawa, H. et al. (1995). "Effects of a Spider Toxin and Its Analoque on Glutamate-Activated Currents in the Nippocampal CA1 Neuron after Ischemia," *J Neurophys* 74:218-225.

Veznik, F. et al. (1991). "Synthese von N1,4-Di(p-cumaroyl)spermin, einem moglichen Biogenese-Vorlaufer von Aphelandrin," *Helvetica Chimica Acta* 74:654-661.

Volkow, N. et al. (1983). "Labeled Putrescine as a Probe in Brain Tumors," *Science* 221:673-675.

Webb, H.K. et al. (1999). "1-(N-Alkylamino)-11-(N-Ethylamino)-4,8-Diazaundecanes: Simple Synthetic Polyamine Analogues That Differentially Alter Tubulin Polymerization," *J. Med Chem* (in press).

Williams, K. (1991) "Minireview: Modulation of the NMDA Receptor by Polyamines," *Life Science* 48:469-498.

Williams, K. (1997). "Interaction of Polyamines with Ion Channels," *Biochem J* 325:289-297.

Wolff, J. (1998). "Promotion of Mircotubule Asembly by Oligocations: Cooperatively between Charged Groups," *Biochemistry* 37:10722-10729.

Xia, C.Q. et al. (1998). "QSAR Analysis of Polyamine Transport Inhibitors in L1210 Cells," *J Drug Target* 6:65-77.

Albanese, L., et al., "Investigations of the Mechanism by which Mammalian Cell Growth is Inhibited by $N^1$ $N^{12}$-Bis(ethyl)spermine," Biochem. j., (1993) 291:131-7.

Ask, A., et al., "Increased Survival of L1210 Leukemic Mice by Prevention of the Utilization of Extracellular Polyamines. Studies Using a Polyamine-Uptake Mutant, Antibiotics and a Polyamine-Deficient Diet," Cancer Lett., (1992) 66:29-34.

Bergeron, R.J., et al., "Antiproliferative Properties of Polyamine Analogues: A Structure-Activity Study," J. Med. Chem., (1994) 37:3464:76.

Bergeron, R.J., et al., "Reagents for the Stepwise Functionalization of Spermine," J. Org. Chem (1988) 53: 3108-11.

Bergeron, R.J., et al., "*Total Synthesis of (+) -15-Deoxyspergualin,*" J. Org. Chem., (1987) 57:1700-3.

Bergeron, R.J. et al., "A Comparison of Structure-Activity Relationships between Spermidine and Spermine Analogue Antineoplastics, " J. Med. Chem., (1997) 40: 1475-94.

Bhaskar Kanth, J.V., et al., "Selective Reduction of Carboxylic Acids into Alcohols Using $NaBH_4$ and $I_2$, " J. Org. Chem., (1991) 56: 5964-5.

Blagbrough, I.S., et al., "Practical Synthesis of the Putative Polyamine Spider Toxin FTX: a Proposed Blocker of Voltage-Sensitive Calcium Channels," Tetrahedron Lett., (1994) 35 (13): 2057-60.

Booth, R.J., et al., "Polymer-Supported Quenching Reagents for Parallel Purification," J. AM. Chem. Soc., (1997) 119: 4882-6.

Borch, R.F., et al., "The Cyanohydridoborate Anion as a Selective Reducing Agent," J. AM. Chem. Soc., (1971) 93 (12): 2897-2904.

Brand, G., et al., "Cyclopolyamines: Synthesis of Cyclospermidines and Cyclospermines, Analogues of Spermidine and Spermine," Tetrahedron Lett., (1994) 35(46): 8609-12.

Bray, A.M. et al., "Simultaneous Multiple Synthesis of Peptide Amides by the Multipin Method. Application of Vapor-Phase Ammonolysis," J. Org. Chem., (1994) 59:2197-2203.

Brown, H.C., et al., "Solvomercuration-Demercuration. I. The Oxymercuration-Demercuration of Representative Olefins in an Aqueous System. A Convenient Mild Procedure for the Markovnikov Hydration of the Carbon-Carbon Double Bond," J. Org. Chem., (1970) 35(6): 1844-50.

Byk, G., et al., "One Pot Synthesis of Unsymmetrically Functionalized Polyamines by a Solid Phase Strategy Starting from their Symmetrical Polyamine-Counterparts," Tetrahedron Lett., (1997) 38(18): 3219-22.

Casero Jr., R.A., et al., "High Specific Induction of Spermidine/Spermine N1-Acetyltransferase in a Human Large Cell Lung Carcinoma," Biochem. J., (1990) 270:615-20.

Chaplinski, V., et al., "*A Versatile New Preparation of Cyclopropylamines from Acid Dialkylamides,*" Angew. Chem. Int. Ed. Engl., (1996) 35(4): 413-4.

Dempcy, R.O. et al., "Design and Synthesis of Ribonucleic Guanidine: A Polycationic Analog of RNA," Proc. Natl. Acad. Sci. U.S.A., (1996) 93:4326-30.

Devraj, R., et al., "A Versatile Solid Phase Synthesis of Lavendustin A and Certain Biologically Active Analogs," J. Org. Chem., (1996) 61:9368-73.

Fleming, S.A., "*Chemical Reagents in Photoaffinity Labeling,*" Tetrahedron, (1995) 51(46): 12479-520.

Furka, A., General Method for Rapid Synthesis of Multicomponent Peptide Mixtures, Int. J. Peptide Protein Res., (1991) 37:487-93.

Gallop, M.A., et al., "Applications of Combinatorial Technologies to Drug Discovery. Background and Peptide Combinatorial Libraries," J. Med. Chem., (1994) 37(9): 1233-51.

Ganem, B., "New Chemistry of Naturally Occuring Polyamines," ACC. Chem. Res., (1982) 15:290-8.

Ganem, B., et al., "Chemistry of Naturally Occurring Polyamines. II Unsaturated Spermidine and Spermine Derivatives," J. Org. Chem., (1987) 52:5044-6.

Ganem, B., et al., "Chemistry of Naturally Occuring Polyamines. 10. Nonmetabolizable Derivatives of Spermine and Spermidine," J. Org. Chem., (1986) 51:4856-61.

Goodnow, Jr. R.A., et al., "Oligomer Synthesis and DNA/RNA Recognition Properties of a Novel Oligonucleotide Backbone Analog: Glucopyranosyl Nuclei Amide (GNA)," Tetrahedron Lett., (1997) 38(18):3199-3202.

Goodnow, Jr., R.A., et al., "Synthesis of Thymine, Cytosine, Adenine, and Guanine Containing N-Fmoc Protected Amino Acids: Building Blocks for Construction of Novel Oligonucleotide Backbone Analogs," Tetrahedron Lett., (1997) 38(18):3195-8.

Gordon, D.W., et al., "Reductive Aikylation on a Solid Phase: Synthesis of a Piperazinedione Combinatorial Library," Bioorg. Med. Chem. Lett., (1995) 5(1): 47-50.

Gordon, E.M., et al., "Applications of Combinatorial Technologies to Drug Discovery Combinatorial Organic Synthesis, Library Screening Strategies, and Future Directions," J. Med. Chem, 91994) 37(10): 1385-1401.

Han, H. et al., "Liquid-Phase Combinatorial Synthesis," Proc. Natl. Acad. Sci. USA, (1995) 92:6419-23.

Hanauske-Abel, H.M. et al., "Detection of a Sub-Set of Polysomal mRNAs Associated with Modulation of Hypusine Formation at the G1-S Boundary Proposal of a Role for elF-5A in onset of DNA Replication," Febs Lett., (1995) 366:92-8.

Hernandez, A.S. et al., "Solid-Supported tert-Alkoxycarbonylation Reagents for Anchoring of Amines During Solid Phase Organic Synthesis," J. Org. Chem., (1997) 62:3153-7.

Iwanowicz, E.J. et al., "Preparation of N, N'- Bis-tert-Butoxycarbonylthiourea,"Synthetic Comm., (1993) 23(10): 1443-5.

Janda, K.D. et al., "*Combinatorial Chemistry: A Liquid-Phase Approach,*" Meth. Enzymol., (1996) 267:234-47.

Jasnis, M.A. et al., "Polyamines Prevent DFMO-Mediated Inhibition of Angiogenesis," Cancer Lett., (1994) 79:39-43.

Kremmer, T. et al., "Comparative Studies on the Polyamine Metabolism and DFMO Treatment of MCF-7 and MDA-MB-231 Breast Cancer Cell Lines and Xenografts," Anticancer Res., (1991) 11:1807-14.

Laguzza, B.C., et al., "A New Protecting Group For Amines. Synthesis of Anticapsin from L-Tyrosine," Tetrahed. Lett., (1981) 22(16):1483-6.

Lakanen, J.R., et al., "α-Methyl Polyamines: Metabolically Stable Spermidine and Spermine Mimics Capable of Supporting Growth in Cells Depleted of Polyamines," J. Med. Chem., (1992) 35:724-34.

Lam, K.S., "Application of Combinatorial Library Methods in Cancer Research and Drug Discovery," Anti-Cancer Drug Des., (1997) 12:145-67.

Lee, J., "Facile Preparation of Cyclopropylamines from Carboxamides," J. Org. Chem., (1997) 62:1584-5.

Li, Y. et al, "Synthesis and Antitumor Evaluation of a Highly Potent Cytotoxic DNA Cross-Linking Polyamine Analogue, 1, 12-Diazindinyl-4, 9-diazadodecane," J. Med. Chem., (1996) 39:339-41.

Lloyd-Williams, P., "*Convergent Solid-Phase Peptide Synthesis,*" Tetrahedron, (1993) 49(48): 11065-133.

Maillard, L., et al., "Percutaneous Delivery of the Gax Gene Inhibits Vessel Stenosis in a rabbit Model of Balloon Angioplasty," Cardiovasc, Res, (1997) 35:536-46.

Marton, L.J., et al., "*Polyamines as Targets for Therapeutic Intervention,*" Annu. Rev. Pharmacol. Toxicol., (1995) 35:55-91.

Muramoto, K., "Preparation and Characterization of Photoactivable Heterobifunctional Fluorescent Reagents," Agric. Biol. Chem., (1984) 48 (11), 2695-9.

Nakaoka, T., et al., "Inhibition of Rat Vascular Smooth Muscle Proliferation in Vitro and In Vivo by Bone Morphogenetic Protein-2," J. Clin. Invest., (1997) 100 (11): 2824-32.

Pfitzner, K.E., et al., "Sulfoxide-Carbodiimide Reactions. I.A. Facile Oxidation of Alcohols," J. AM. Chem. Soc., (1965) 87 (24): 5661-9.

Quemener, V., et al., "Polyamine Deprivation: A New Tool in Cancer Treatment," Anticancer Res., (1994) 14:443-8.

Raines, D.E., et al., "Potential-Dependent Phase Partitioning of Fluorescent Hydrophobic Ions in Phospholipid Vesicles," J. Membrane Biol., (1984) 82:241-7.

Rajeev, K.G., et al., "Conformationally Restrained Chiral Analogues of Spermine: Chemical Synthesis and Improvements in DNA Triplex Stability," J. Org Chem., (1997) 62:5169-73.

Ranganathan, R.S., et al., "Novel Analogs of Nucleoside 3', 5'-Cyclic Phosphates. I. 5'-Mono-and Dimethyl Analogs of Adenosine 3', 5'-Cyclic Phosphate," J. Org. Chem., (1974 39(3):290-8.

Rink, H., "Solid-phase synthesis of Protected Peptide Fragments Using A Trialkoxy-Diphenyl-Methylester Resin," Tetrahed. Lett., (1987) 28(33): 3787-90.

Salemmen, F. R., et al., "Serendipity Meets Precision: The Integration of Structure-Base Drug Design and Combinatorial Chemistry for Efficient Drug Discovery," Structure, (1997) 5(3):319-24.

Sasaki, Y. et al., "Solid-Phase Synthesis and Biological Properties of Ψ[CH$_2$NH] Pseudopeptide Analogues of a Highly Potent Somatostatin Octapeptide," J. Med. Chem., (1987 30(7): 1162-6.

Schallenberg, E.E., et al., "Ethyl Thioltnifluoroacetate As An Acetylating agent with Particular Reference to Peptide Synthesis," J.AM.Chem.Soc., (1955) 77:2779-83.

Seiler, N. et al., "*Polyamine transport in Mammalian Cells. An Update.,*" Int. J. Biochem. Cell Biol., (1996) 2898): 843-61.

Seiler, N. et al., "*Polyamine Transport in Mammalian Cells,*" Int. J. Biochem., (1990) 22(3):211-8.

Shyng, S.-L., et al., "Depletion of Interacellular Polyamines Relieves Inward Rectification of Potassium Channels," Proc. Natl. Acad. Sci. USA, (1996) 93:12014-9.

Siegel, M.G. et al., "Rapid Purification of Small Molecule Libraries b y Ion Exchange Chromatography," Tetrahedron Lett., (1997) 38, (19): 3357-60.

Singh, S. et al., "Characterization of Simian Malarial Parasite (Plasmodium Knowlesi) -induced Putrescine Transport in Rhesus Monkey Erythrocytes," J. Biol. Chem., (1997) 272(21): 13506-11.

Thompson, L.A. et al., "Straightforward and General Method for Coupling Alcohols to Solid Supports," Tetrahed. Lett., (1994) 35:9333-6.

Ventura, C. et al., "Polyamine Effects on [Ca2+]1 Homeostasis and Contractility in Isolated Rat Ventricular Cardiomyocytes," AM. J. Physiol, (1994) 267:H587-H592.

Wang, S.-S., "p-Alkoxybenzyl Alcohol Resin and p-Alkoxybenzyloxycarbonylhydrazide Resin for Solid Phase Synthesis of Protected Peptide Fragments," J. Am. Chem. Soc., (1973) 95(4): 1128-1333.

"The role of polyamine catabolism in polyamine analogue-induced programmed cell death," Ha et al., *Proc. Natl., Acad. Sci.*, vol. 94, pp. 11557-11562, Oct. 1997.

"The natural polyamine spermine fuctions directly as a free radical scavenger", Ha et al., *Proc. Natl. Acad. Sci.*vol. 95, pp. 11140-11145, Sep. 1998.

| # | Structure | Ki (M)[a] | R[b] | Method[c] |
|---|---|---|---|---|
| 3 | 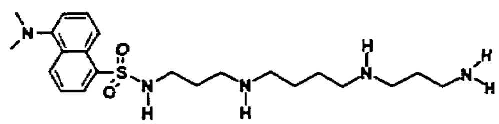 | 0.080 | 20 | I |
| 4 | 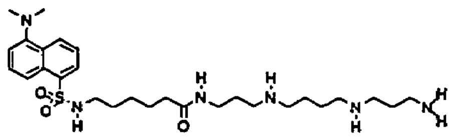 | 0.010 | 400 | IX, XIII |
| 5 | 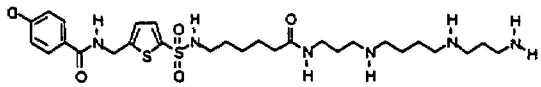 | 0.010 | 210 | XIII |
| 6 | 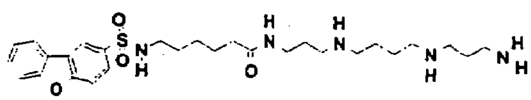 | 0.005 | 220 | XIII |
| 7 | 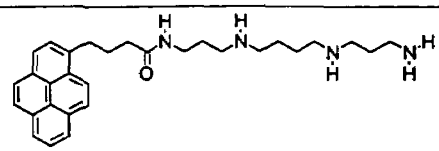 | 0.10 | 3.6 | III |
| 8 | 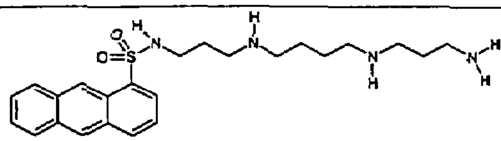 | 0.110 | 3.7 | II |
| 9 | 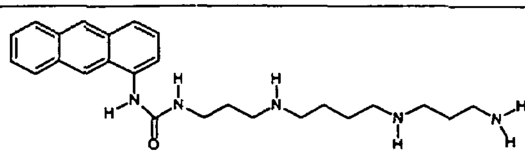 | 0.440 | 2.7 | IV |
| 10 | 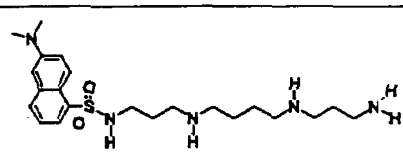 | 0.050 | >10 | XV |
| 11 | | 0.190 | 2.4 | XV | a  Inhibition of polyamine uptake: Ki determined from Lineweaver-Burke double reciprocal plots
b  Inhibition of Tumor Cell Growth: R is ratio of IC50 (compound alone) to IC50 (compound + DFMO)
c  Numbers refer to Examples (describing synthesis)
d  Purchased from Aldrich Chemical Company

Fig. 2/1

| # | Structure | Ki (M)[a] | R[b] | Method[c] |
|---|---|---|---|---|
| 12 | 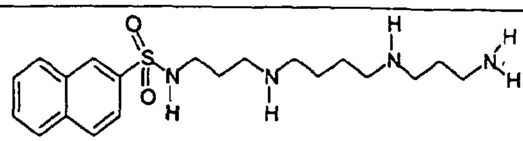 | 0.150 | 4.3 | XV |
| 13 | 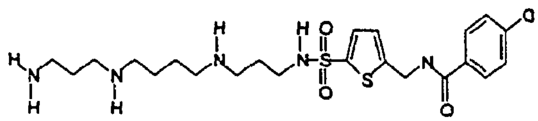 | 0.058 | >47 | XV |
| 14 | 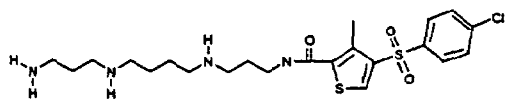 | 0.037 | 14 | XVII |
| 15 | 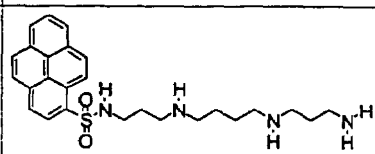 | 0.091 | 2.2 | II |
| 16 | 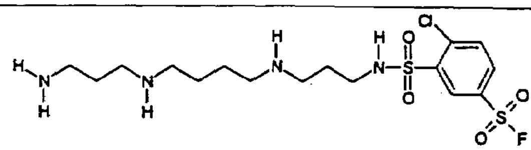 | 0.08 | 2.1 | XV |
| 17 | 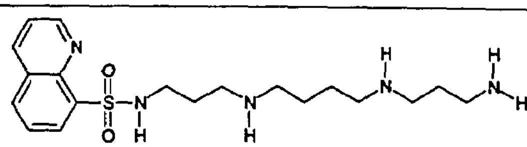 | 0.43 | >31 | XV |
| 18 | 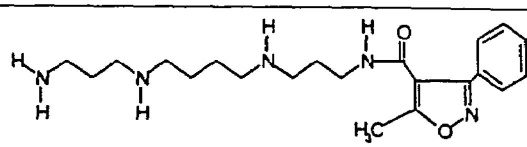 | 0.083 | 40 | XVII |
| 19 | 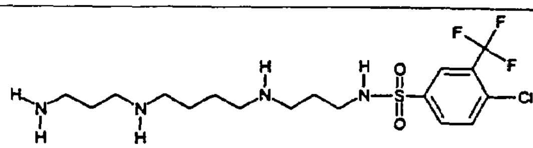 | 0.24 | >10 | XV |
| 20 | 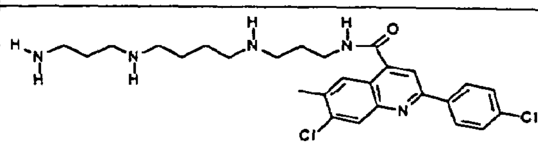 | 0.28 | 1.0 | XVII |
| 21 | 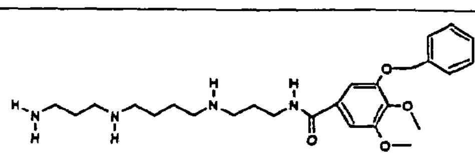 | 0.084 | 1.0 | XVII |

Fig. 2/2

| # | Structure | Ki (M)[a] | R[b] | Method[c] |
|---|---|---|---|---|
| 22 | 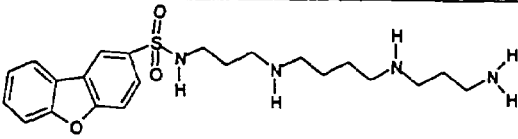 | 0.066 | 11 | XV |
| 23 | 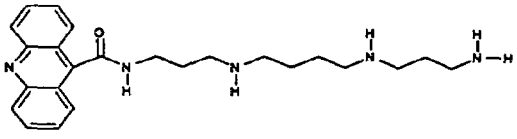 | 0.250 | 6.2 | II |
| 24 | 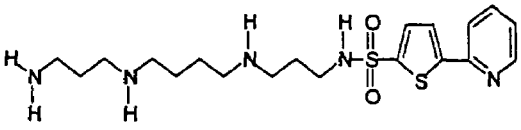 | 0.23 | 10 | XV |
| 25 | 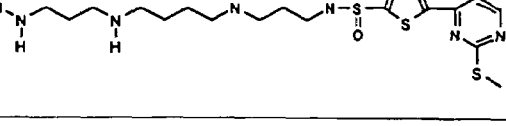 | 0.067 | 8.6 | XV |
| 26 | 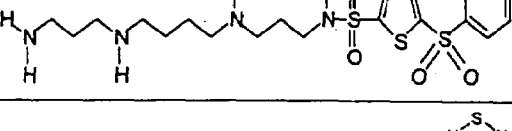 | 0.180 | 15 | XV |
| 27 | 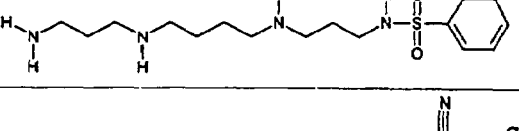 | 0.650 | 9.9 | XV |
| 28 | 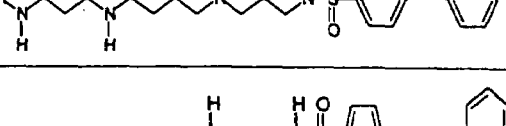 | 0.054 | 9.3 | XV |
| 29 | 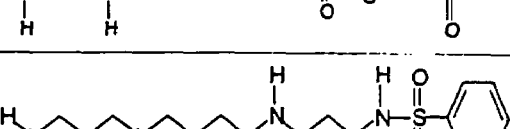 | 0.076 | >46 | XV |
| 30 | 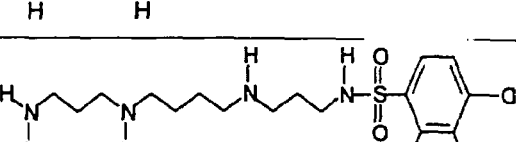 | 0.120 | >10 | XV |
| 31 | 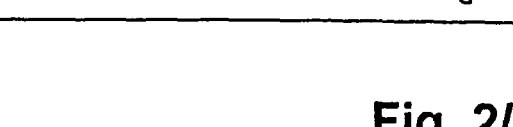 | 0.083 | >12 | XII |
Fig. 2/3

| # | Structure | Ki (M)[a] | R[b] | Method[c] |
|---|---|---|---|---|
| 32 | 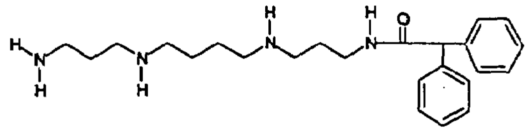 | 0.093 | 2.1 | XVII |
| 33 | 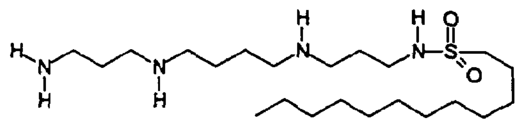 | 0.17 | 1.4 | XV |
| 34 | 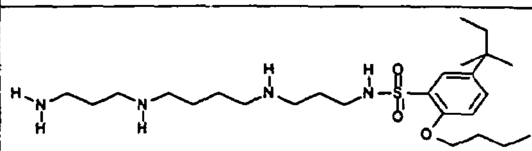 | 0.120 | 1.0 | XV |
| 35 | 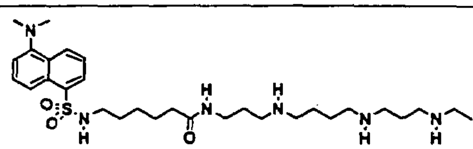 | 0.041 | 33 | XIII |
| 36 | 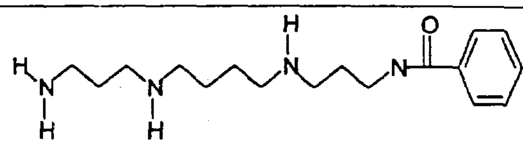 | 0.61 | >2 | XVII |
| 37 | 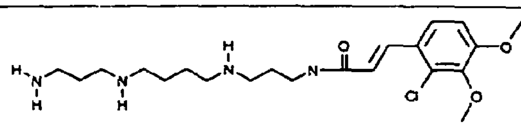 | 0.150 | 2.4 | XVII |
| 38 | 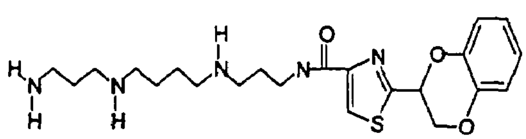 | 0.140 | 1.0 | XVII |
| 39 | 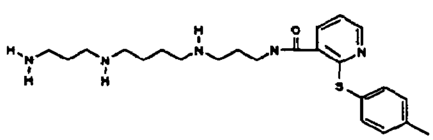 | 0.500 | 1 | XVII |
| 40 | 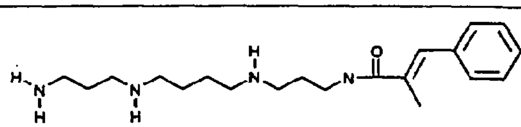 | 0.086 | 18 | XVII |
| 41 | 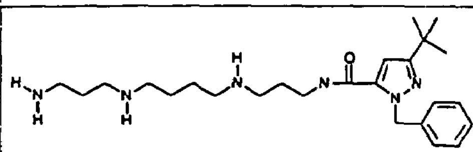 | 0.200 | 1.0 | XVII |

Fig. 2/4

| # | Structure | Ki (M)[a] | R[b] | Method[c] |
|---|---|---|---|---|
| 42 | 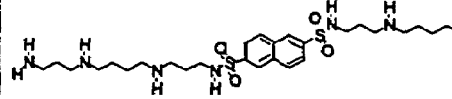 | 0.110 | 1.1 | XIV |
| 43 | 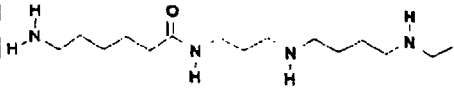 | 0.033 | 76 | XVII |
| 44 | 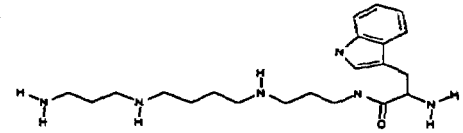 | 0.073 | 39 | XIII |
| 45 | 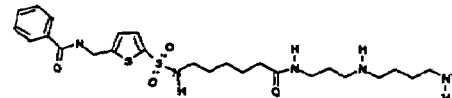 | 0.052 | 3.0 | XIII |
| 46 | 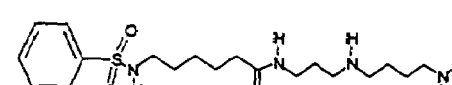 | 0.082 | 63 | XIII |
| 47 | 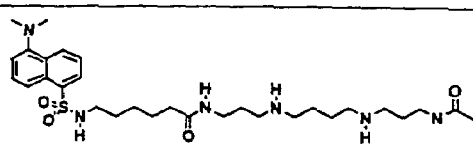 | 2.1 | 6.8 | XIII |
| 48 | 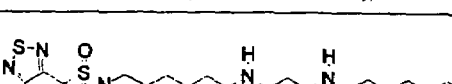 | 0.079 | >49 | XIII |
| 49 | 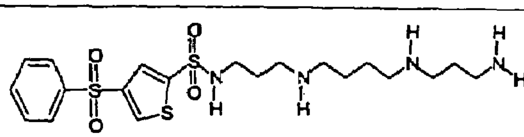 | 0.067 | 3.2 | XV |
| 50 | 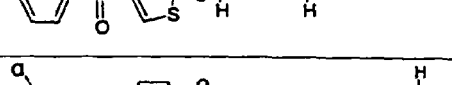 | 0.12 | 1.0 | XVII |
| 51 | 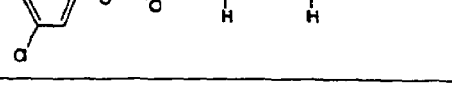 | 0.083 | 1.5 | XV |
Fig. 2/5

| # | Structure | $K_i$ (M)[a] | R[b] | Method[c] |
|---|---|---|---|---|
| 52 | 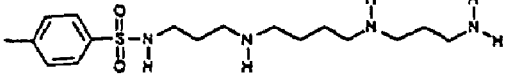 | 0.094 | 5.3 | XV |
| 53 | 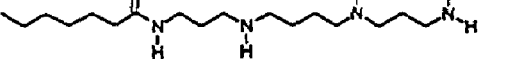 | 0.18 | 1.0 | XV |
| 54 | 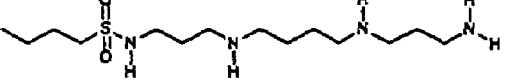 | 0.19 | 2.0 | XV |
| 55 | 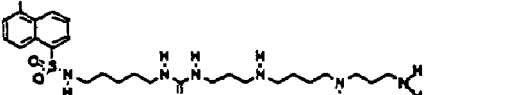 | 0.079 | >1.1 | IV |
| 56 | 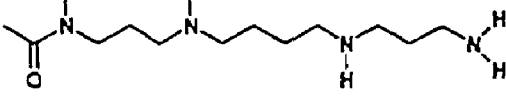 | 0.190 | | d |
| 57 | 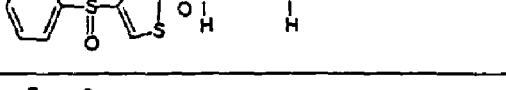 | 0.017 | 170 | XV |
| 58 | 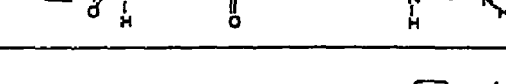 | 0.050 | 189 | XIII |
| 59 | 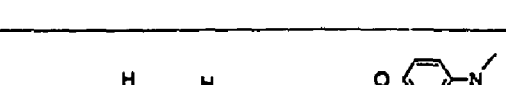 | | >1 | XIII |
| 60 | 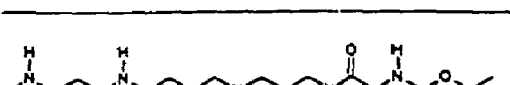 | | >1 | XIII |
| 61 | 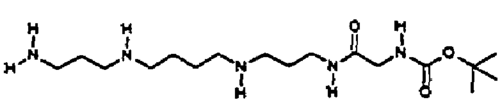 | 0.200 | 1.0 | XIII |
Fig. 2/6

| # | Structure | Ki (M)[a] | R[b] | Method[c] |
|---|---|---|---|---|
| 62 | 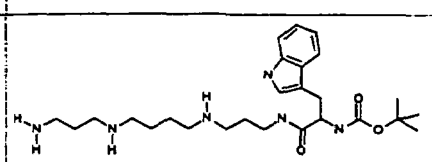 | | >2.0 | XIII |
| 63 | 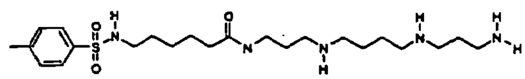 | 0.050 | >1 | XIII |
| 64 | 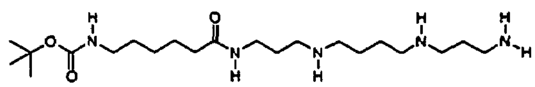 | 0.046 | | XIII |
| 65 | 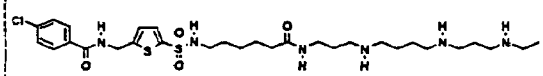 | 0.012 | | XIII |
| 66 | 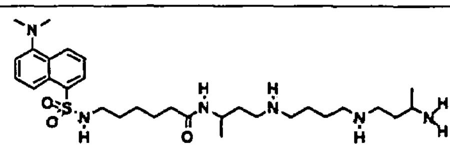 | 0.018 | 27 | XIII |
| 67 | 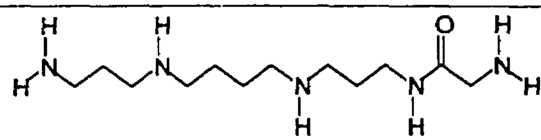 | 0.07 | 1.0 | XIII |
| 68 | 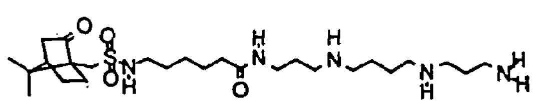 | 0.110 | >4.4 | XIII |
| 69 | 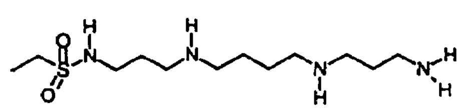 | 0.22 | 1 | XV |
| 70 | 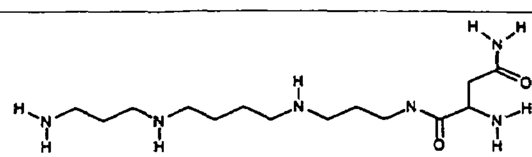 | 0.033 | >12.2 | XIII |
| 71 | 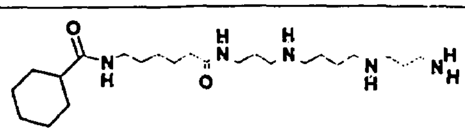 | 0.160 | >1.5 | XIII |

Fig. 2/7

| # | Structure | Ki (M)[a] | R[b] | Method[c] |
|---|---|---|---|---|
| 72 | 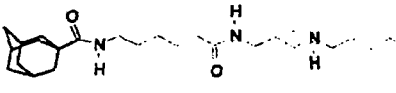 | 0.031 | >100 | XIII |
| 73 | 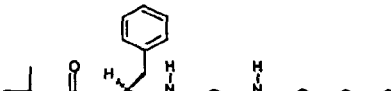 | 0.094 | >1 | XIII |
| 74 | 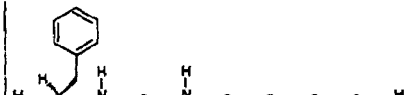 | 0.200 | 1.0 | XIII |
| 75 | 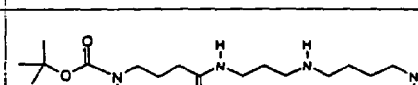 | 0.130 | >1 | XIII |
| 76 | 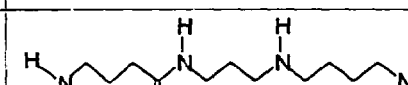 | 0.040 | 1.0 | XIII |
| 77 | 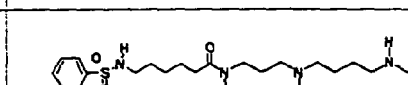 | 0.093 | 1 | XIII |
| 78 | 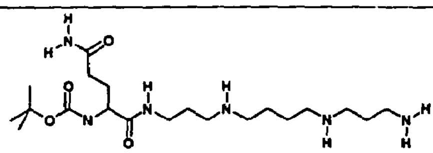 | 0.156 | | XIII |
| 79 | 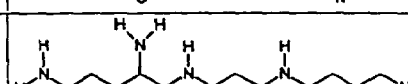 | 0.047 | 1 | XIII |
| 80 | 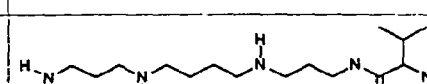 | 0.258 | | XIII |
| 81 | 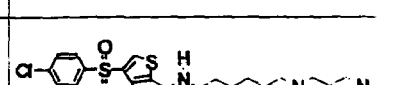 | 0.0096 | 153 | XIII |
Fig. 2/8

| # | Structure | Ki (M)[a] | R[b] | Method[c] |
|---|---|---|---|---|
| 82 | 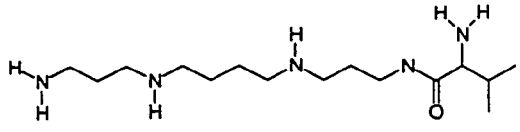 | 0.097 | >54 | XIII |
| 83 | 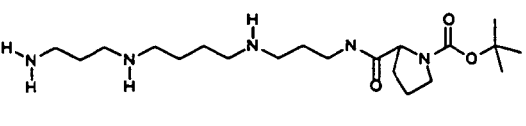 | 0.183 | | XIII |
| 84 | 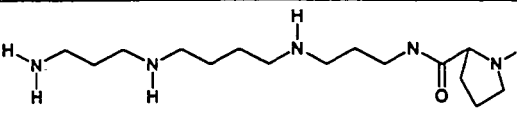 | 0.036 | >3.2 | XIII |
| 85 | 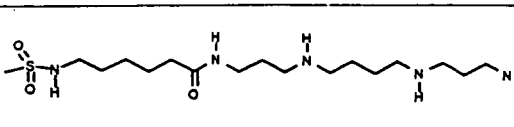 | 0.048 | >6.5 | XIII |
| 86 | 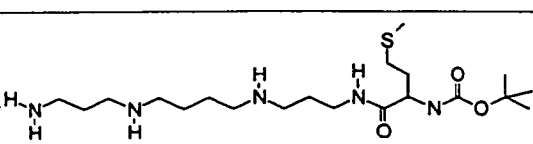 | 0.091 | | XIII |
| 87 | 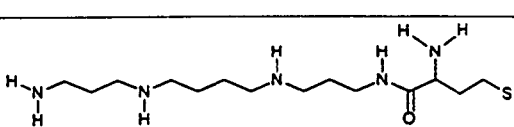 | 0.034 | >1 | XIII |
| 88 | 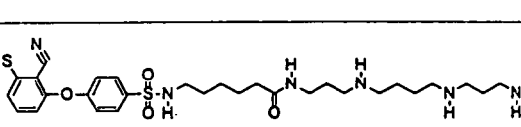 | 0.014 | >40 | XIII |
| 89 | 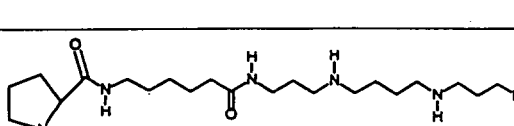 | 0.020 | >1 | XIII |
| 90 | 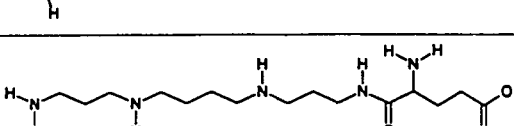 | 0.077 | | XIII |
| 91 | 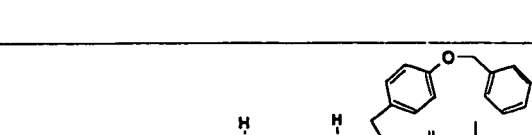 | 0.037 | 1 | XIII |
Fig. 2/9

| # | Structure | Ki (M)[a] | R[b] | Method[c] |
|---|---|---|---|---|
| 92 | 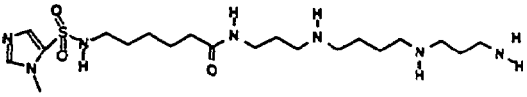 | 0.300 | 1 | XIII |
| 93 | 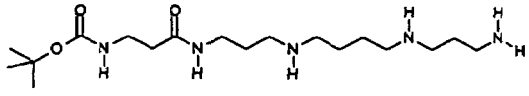 | 0.061 | 1 | XIII |
| 94 | 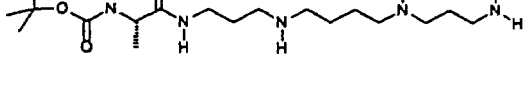 | 0.042 | 1 | XIII |
| 95 | 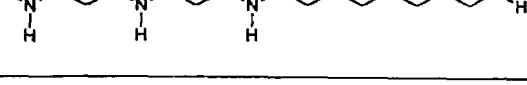 | 0.050 | 1 | XIII |
| 96 | 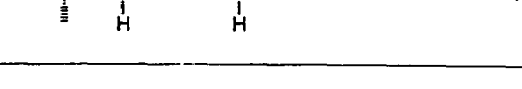 | 0.034 | 1 | XIII |
| 97 | 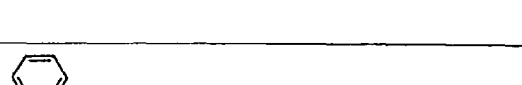 | 0.027 | 1 | XIII |
| 98 | 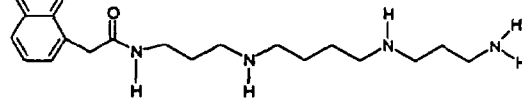 | 0.180 | 12 | d |
Fig. 2/10

Where  X = halide or N-hydroxysuccinimide ester
R = head group
polyamine = spermine (or other)
Y = O or S or NHR
(corresponding to ureas, thioureas and guanidines, respectively

Fig. 10
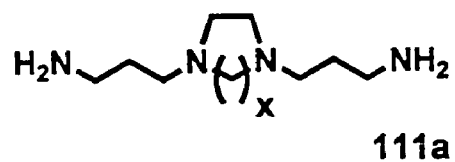
111a
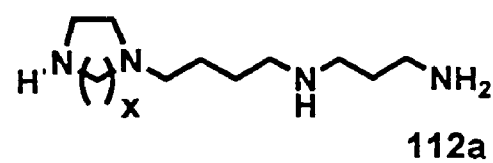
112a
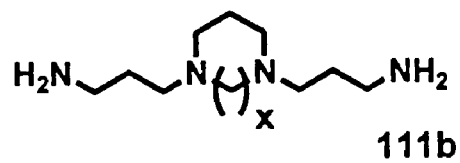
111b
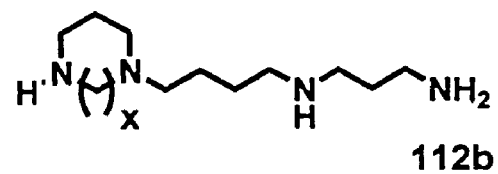
112b
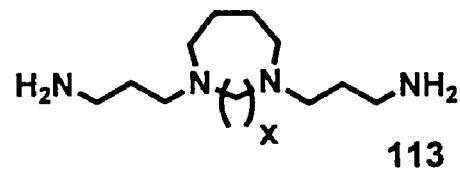
113
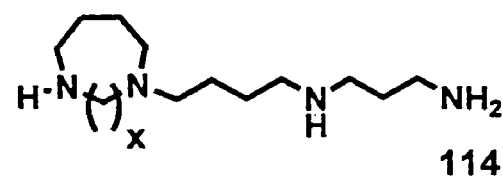
114
x = 1 to 4
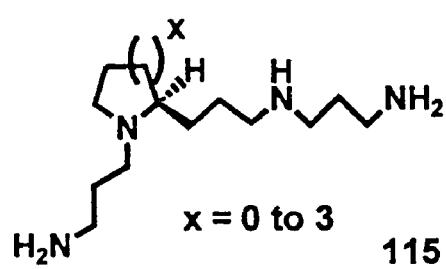
x = 0 to 3
115 where   Y = O, S or NH;
R = various groups including: propylaziridine, propylamine, hexyldansylsulfonamide
$R_1$ = H, $CH_3(CH_2)_n$-, where n=1 to 10;
X = H or halogen

Fig. 15
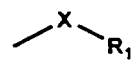
135
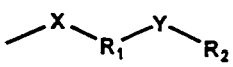
136
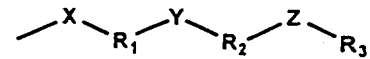
137
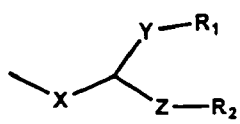
138
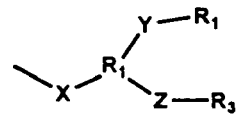
139
Where   X=spacer$_1$; Y=spacer$_2$; and Z=spacer$_3$; and
R$_1$, R$_2$, and R$_3$ can be alicyclic, aromatic, or heterocylic
Fig. 16
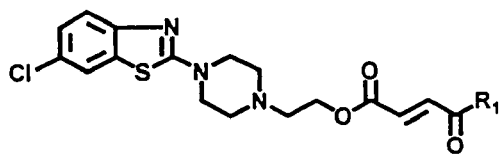
140
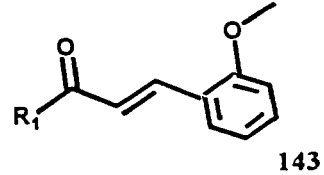
141
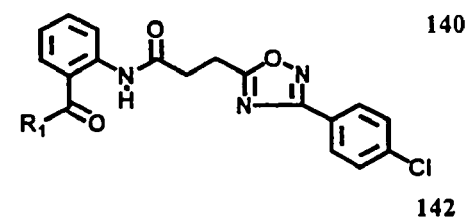
142
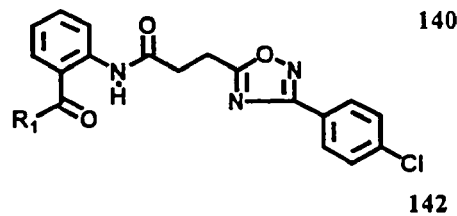
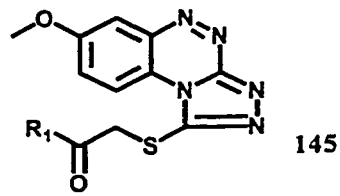
143
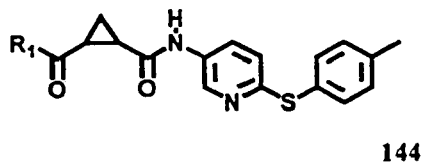
144
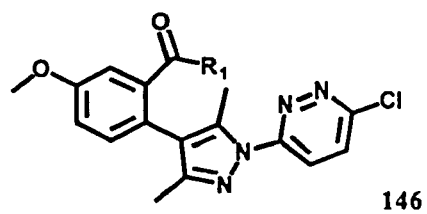
145
146
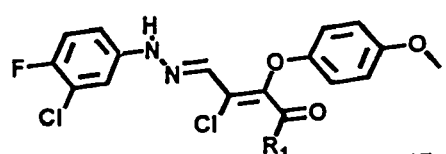
147 stereochemistry:
L is S, D is R

Where R=head group; R"= H, -CH$_3$-, -CH$_2$CH$_3$, -CHF$_2$

DACS with an ODC Inhibitor Enhances the Growth-Inhibition of MDA-MB-231 Breast Carcinoma Cells DACS Inhibits Growth in the Presence of 1.0 $\mu$M Spermidine

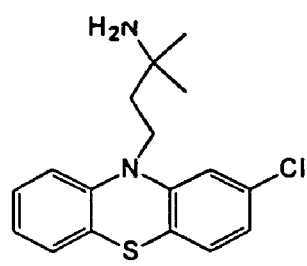
161
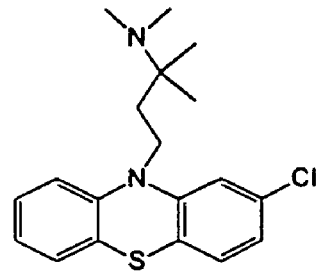
162
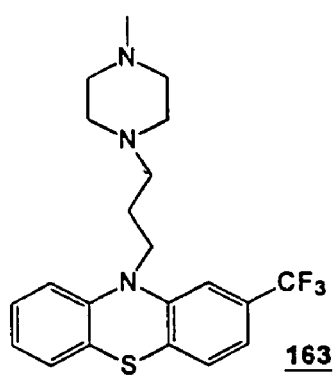
163
trifluoperazine
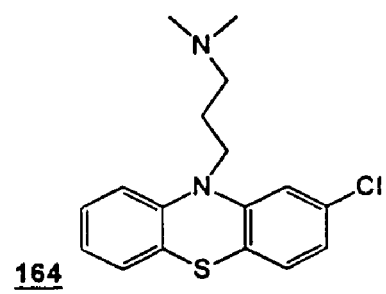
164
Thorazine
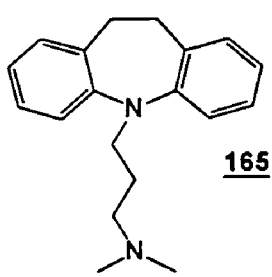
165
Imipramine
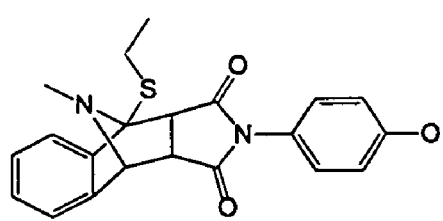
166
Fig. 25

Fig. 31
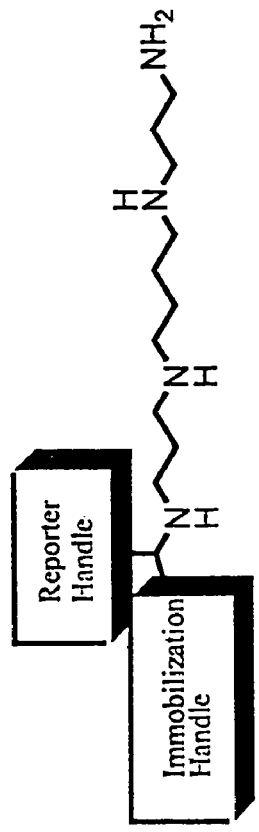
A. Reporter and Immobilization handles are both $N^1$-terminal
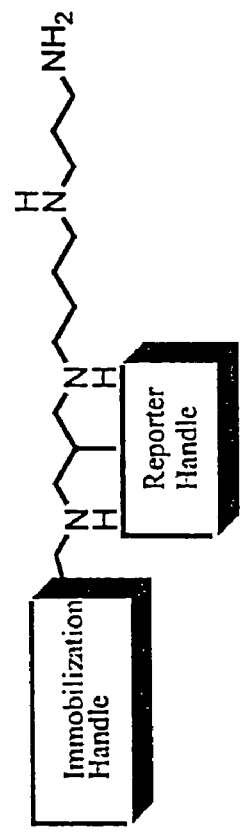
B. Reporter Handle is internal and Immobilization handle is N-terminal.
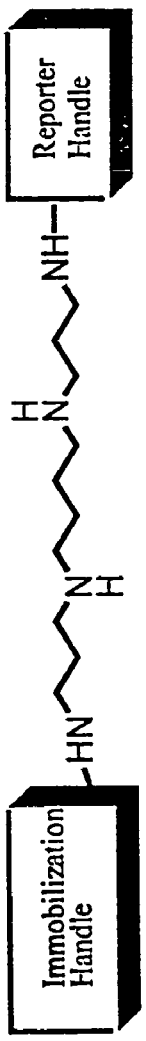
C. Immobilization and Reporter handles are both $N^1$ and $N^{12}$ terminal, respectively

General Scheme

E = Extender
T = Terminator

Other Base / Polyamine Linkers As Terminators

Fig. 40
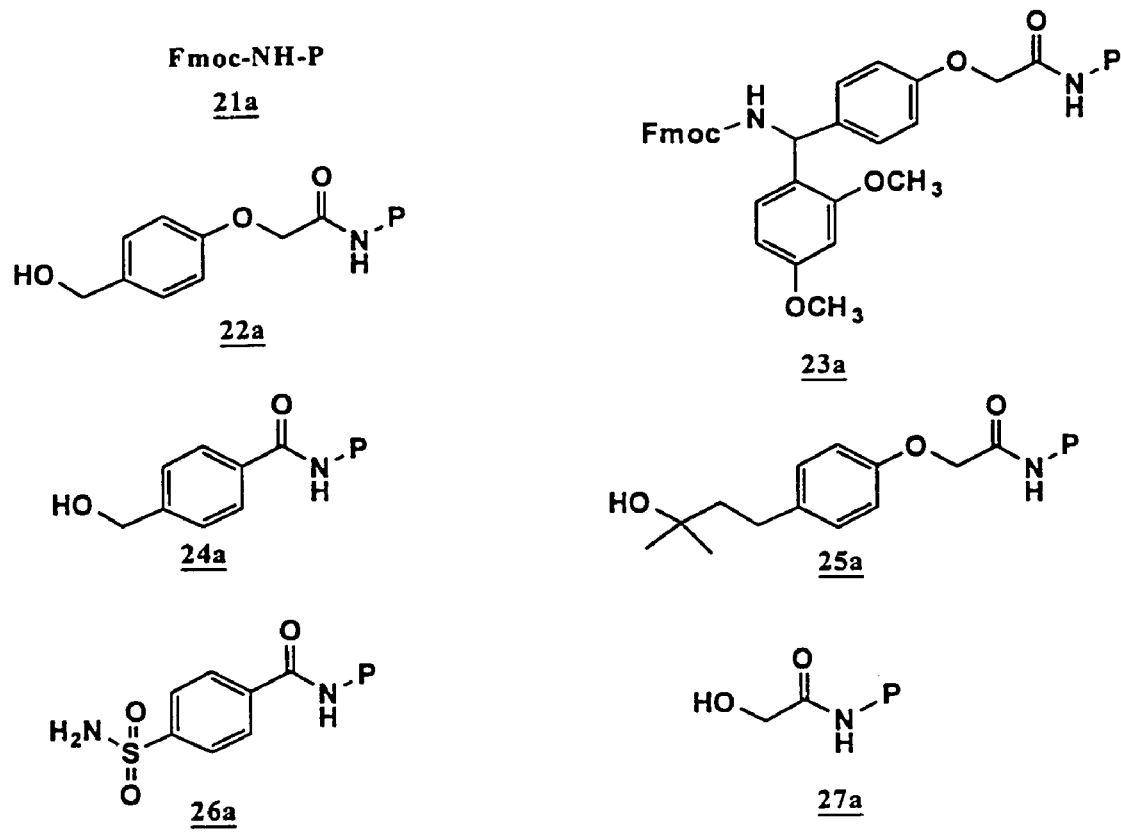
Fig. 41
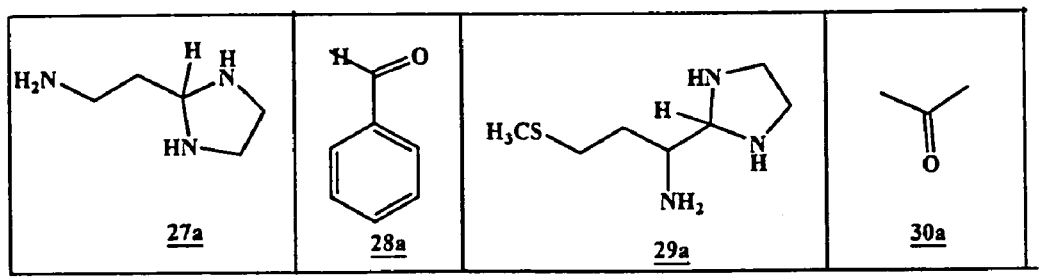
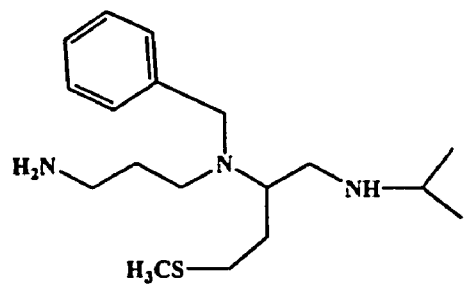

POLYAMINE ANALOGUES AS THERAPEUTIC AND DIAGNOSTIC AGENTS

This application is a continuation of Ser. No. 09/341,400, filed Sep. 3, 1999, U.S. Pat. No. 6,172,269, which is a 371 of PCT/US98/14896, filed Jul. 15, 1998, which claims benefit of priority from U.S. provisional application 60/052,586, filed Jul. 15, 1997, 60/065,728, filed Nov. 14, 1997, and 60/085,538, filed May 15, 1998.

BACKGROUND OF THE INVENTION

1. Field of the Invention

The invention in the field of chemistry and biochemistry relates to the synthesis and use of novel polyamine transport (PAT) inhibitor compounds with pharmacological or agricultural uses and as probes for biochemical assays or for purification of selected polyamine binding targets. As drugs, these compounds are used to treat disorders of undesired cell proliferation, primarily cancer, alone or combined with other agents such as polyamine synthesis inhibitors. An assay employing some of these compounds is useful for monitoring polyamine uptake or transport (PAT) and allows analysis of binding sites for polyamines or for other basic ligands on a variety of molecules. This invention also relates to the synthesis and use of novel polyamine combinatorial libraries. These libraries are used to discover compositions that inhibit PAT and/or that bind to a cellular polyamine transporter (PATr). Various members of these libraries or compounds discovered through use of the libraries have utility as drugs, agricultural chemicals, and as probes. This invention also identifies key elements that comprise the polyamine binding sites of membrane as well as soluble proteins.

2. Description of the Background Art

Polyamines are ubiquitous molecules that provide a "buffer" system for the cell by modulating the activities of proteins, RNA, DNA, and lipids. Polyamines may play a direct role in apoptosis. Mammals and other organisms have an active polyamine uptake and recycling system that complements their polyamine synthetic capabilities. Because polyamines modulate such a large range of molecules and cellular activities, polyamine analogues, as disclosed herein, offer novel approaches for targeting a variety of disease states, particularly cancer, and also provide unique tools to monitor cellular activities.

Polyamines and Cancer

The potential of polyamines as anticancer agents has been long recognized. Polyamines affect chromatin structure in eukaryotes and prokaryotes by binding specifically to DNA (Balasundaram, D. et al., *Mol. Cell. Biol.* 100:129–140, 1991) so that condensation occurs when the binding sites on DNA are saturated. Acetylation of polyamines and histones lowers their affinity for DNA and is believed to occur in tandem to alter the structure and function of the nucleosome, thus regulating DNA replication and transcription by loosening DNA at the ends of the core particle. Because polyamines are absolutely essential for DNA replication, they are of interest in the treatment of cancer. Particular interest has been focused on preventing cell proliferation by lowering intracellular polyamine levels. Polyamine analogues as described herein are useful for preventing or treating cancer and other proliferative diseases by acting at a number of different levels. The present invention focuses on the inhibition of PAT. Other targets include induction of spermine/spermidine acetyltransferase (SSAT), hypusine modification, and other proteins that inhibit the cell cycle or induce apoptosis.

The Polyamine Transporter (PATr)

The increased demand for polyamines by rapidly growing, transformed cancer cells is only partially met by an increased rate of synthesis. To exploit this increased need for polyamines, synthesis inhibitors have been sought. Additionally, lowering polyamine concentrations can result in aberrations in chromatin structure leading to cell death or inhibition of proliferation (Quemener, V. et al., *Anticancer Res.* 14:443–448, 1994; Porter, C. W. et al., *Cancer Res.* 53:581–586, 1993). It has become increasingly apparent that the initial disappointing results observed in the clinic with polyamine synthesis inhibitors arises from compensatory increases in transport of polyamines by a specific active transport system (Seiler, N. et al., *Int. J. Biochem.* 22:211–218, 1990; Seiler, N. et al., *J. Biochem. Cell. Biol.* 28:843–861, 1996). The promising results observed in cell culture with a suicide substrate inhibitor of ornithine decarboxylase, α-difluoromethylornithine (DFMO), or with an inhibitor of S-adenosylmethionine decarboxylase, methylglyoxal bis(guanylhydrazone) (MGBG) did not transfer to human clinical trials (Schecter, P. J. et al., *In Inhibition of Polyamine Metabolism. Biological Significance and Basis for New Therapies*; McCann, P. P. et al., eds; 1987, pp 345–364). Since the only two avenues for carbon transfer into polyamine pools are synthesis or transport, simultaneous inhibition of both of these pathways is considered by the present inventors to be a promising anti-cancer therapeutic approach.

A study confirming the validity of this chemotherapeutic approach used transplanted murine L1210 leukemia cells that were deficient in PAT. Mice transplanted with the wild-type L1210 cancer cells (with intact PAT) died after 12 days, even when treated with DFMO. In contrast, DFMO mice transplanted with PAT-deficient L1210 cells lived longer than 60 days (Ask, A. et al., *Cancer Lett.* 66:29–34, 1992). These authors also showed that treatment of mice harboring wild-type L1210 cells with a combination of (1) DFMO (2) a low polyamine diet and (3) antibiotics (which decrease polyamine production by gut flora) resulted in prolonged survival compared to treatment with DFMO alone.

Augmented PAT into cancer cells promotes cell killing. J. L. Holley et al. (*Cancer Res.* 52:4190–4195, 1992) showed up to a 225-fold increase in cytotoxicity of a chlorambucil-spermidine conjugate compared to chlorambucil alone. A series of nitroimidazole-polyamine conjugates were also effective (Holley, J. L. et al., *Biochem. Pharmacol.* 43:763–769, 1992). Others showed that mice infected with a multi-drug resistant strain of malaria were cured by treatment with a chloroquinoline-putrescine conjugate (Singh, S. et al., *J. Biol. Chem.* 272:13506–13511, 1997). Thus, the effectiveness of cytotoxic compounds could be enhanced by their conjugation with polyamines. These effects may have been due to the exploitation of the PAT system to deliver these compounds into cancer cells. The present invention is therefore directed in part to rapid and efficient testing of many different conjugates between polyamines and known drugs for their transport into cells. Furthermore, as described below, this invention combines the cytotoxic properties of known drugs with the facilitated transport of polyamines, which relies on the present inventors' discoveries surrounding the PATr described herein. By accessing the database of structure-activity-relationships (SARs) of PATr substrates, the present inventors are able to predict the transportability of a novel chemical entity or a novel polyamine conjugate.

Polyamine Transport (PAT) Assays

There is no known high-throughput assay for measuring PAT. A radiochemical assay is used for biochemical analysis of transport and has been used to study PAT in yeast and a variety of mammalian cells (Kakinuma, Y. et al., *Biochem. Biophys. Res. Comm.* 216:985–992, 1995; Seiler, N. et al., *Int. J. Biochem. Cell Biol.* 28:843–861, 1996). See, for example Huber, M. et al. *Cancer Res.* 55:934–943, 1995.

The radiometric assay uses radiolabeled polyamines such as putrescine, spermidine or spermine, but, due to the low signal, large numbers of adherent or non-adherent cells are required. Additional care is required with spermine due to its non-specific adsorption to cells and plastics. Cells are mixed with the test compounds and the radiolabeled polyamine to initiate the assay. The cells are incubated for 1–60 minutes, depending on cell type. The assay is terminated by removal of the medium and cooling the plates to 4° C. The cells are then washed with cold medium three times, dissolved in 0.1% sodium dodecyl sulfate and the radioactivity in solution is then determined by scintillation counting. This assay is difficult to scale up to a high throughput procedure due to the low signal from the radiolabel and the handling requirements inherent in procedures with radioactivity.

Combinatorial Approaches to Polyamines and Analogues

Combinatorial chemistry, a rapidly changing field of molecular exploration, is still in its infancy. For reviews, see Lam, K. S., *Anticancer Drug Des.* 12:145–167, 1997; Salemme, F. R. et al.; *Structure* 5:319–324, 1997; Gordon, E. M. et al., *J. Med. Chem.* 37:1385–1401, 1994; Gallop, M. A. et al., *J. Med. Chem.* 37:1233–1251, 1994). The pharmaceutical industry, is now realizing that the original approach of the combined synthesis of hundreds to thousands of compounds in one "flask" followed by testing and deconvoluting the results is a tedious process with many pitfalls. The more traditional approach of medicinal chemistry, that is, the synthesis and testing of one compound at a time, yields more reliable and informative results about the structure-activity relationship (SAR) around a target. The trend in combinatorial chemistry is therefore towards synthesis of multiple compounds at once, with each in a separate container. Therefore, many have adopted this one-compound/one-well parallel synthetic approach to molecular exploration. While many lead compounds have been generated this way, the chemistries do not necessarily lead to a molecule with the necessary drug-like characteristics.

Combinatorial chemistry, a rapidly changing field of molecular exploration, is still in its infancy. For reviews, see Lam, K. S., *Anticancer Drug Des.* 12:145–167, 1997; Salemme, F. R. et al.; *Structure* 5:319–324, 1997; Gordon, E. M. et al., *J. Med. Chem.* 37:1385–1401, 1994; Gallop, M. A. et al., *J. Med. Chem.* 37:1233–1251, 1994). The pharmaceutical industry, is now realizing that the original approach of the combined synthesis of hundreds to thousands of compounds in one "flask" followed by testing and deconvoluting the results is a tedious process with many pitfalls. The more traditional approach of medicinal chemistry, that is, the synthesis and testing of one compound at a time, yields more reliable and informative results about the SAR around a target. The trend in combinatorial chemistry is therefore toward synthesis of multiple compounds at once, with each in a separate container. Therefore, many have adopted this one-compound/one-well parallel synthetic approach. While many lead compounds have been generated this way, the chemistries do not necessarily lead to a molecule with the necessary drug-like characteristics.

Polyamine analogues are notoriously difficult to synthesize. Due to the polycationic nature of the final products, traditional chromatographic techniques such as silica gel chromatography cannot be used. Intermediates need a lipophilic protecting group that enables purification of the compounds and extraction with organic solvents. Bergeron has solved some of these problems through the use of the mesityl-type amino protecting group (Bergeron, R. J. et al., *J. Med. Chem.* 40:1475–1494, 1997), which not only solved the problems of handling (allowing purification by silica gel and extraction by organic solvents), but also gave a synthetic handle to extend the backbone of the polyamine. After treatment with NaH, a sodium amide anion is produced which can be alkylated with an alkyl halide to extend the backbone.

Although this approach extends synthetic possibilities somewhat, it is still significantly limited. Use of the mesityl group requires that a harsh reagent like HBr/HOAc be employed for removal, thereby limiting the substituents of the resulting polyamine acid-stable ones. The availability of suitable alkyl halides, together with the amino starting materials, is also limited. Therefore, while this approach has made significant inroads toward simpler analogue production, it is severely limited in its potential for structural diversity. Other synthetic approaches suffer from similar limitations (Moya, E. et al., *In Neuropharmacology of polyamines*; Carter, C., ed.; Academic Press: London, 1997; pp. 167–184). Several initial reports of solid phase synthesis of polyamine analogues (Byk, G. et al., *Tetrahed. Lett.* 38:3219–3222, 1997; Furka, A., *Int. J. Peptide Protein Res.* 37:487, 1991) have serious limitations including a covalently attached linker residue and the lack of sufficient diversity of structural components. These deficiencies are effectively addressed by the present invention.

Induction of Spermine/Spermidine Acetyltransferase (SSAT)

Cellular levels of polyamines are tightly regulated so that only a small window of variability in concentration is tolerated. This regulation is mediated by the control of polyamine synthesis, uptake and catabolism. Abnormally high concentrations of polyamines induce the enzyme SSAT which is associated with apoptosis (Parchment, R. E. et al., *Cancer Res.* 49:6680–6686, 1989). Polyamine analogues induce apoptosis by induction of this enzyme (Ha, et al., *Proc. Natl. Acad. Sci.* 94:11557–11562, 1997; Albanese, L. et al., *Biochem. J.* 291:131–137, 1993) in a cell type-specific way, presumably due to the accumulation of the polyamine analogue in the cell and its binding to a polyamine sensitive repressor or activator of SSAT transcription. Acetylated polyamines, the products of the SSAT-catalyzed reaction, are substrates for the enzyme polyamine oxidase which generates stoichiometric release of $H_2O_2$ believed to be responsible a more proximate cause of the apoptotic response.

Hypusine

The protein eIF-5A appears to play a role in protein synthesis, although its exact function remains obscure (Hanauske-Abelm, H. M. et al., *FEBS Lett.* 266:92–98, 1995). EIF-5A is unique in that it is modified by the unusual amino acid hypusine. Hypusine is generated post-translationally by the sequential action of deoxyhypusyl synthase (using spermidine as a substrate) and deoxyhypusyl hydroxylase. Inhibition of this modification of eIF-5A coincides with proliferative arrest late in the G1 phase of the cell cycle. This modification occurs in most, if not all, eukaryotes. The present inventors have noted that inhibitors of deoxyhypusyl synthase would be useful in treating diseases associated with unwanted cell proliferation, such as cancer, by blocking the cell cycle.

Inhibition of Angiogenesis

Inhibition of polyamine synthesis decreases the vascularization of solid tumors. One month of treatment with DFMO resulted in a 50% reduction in neoplastic vessel count in humans with cervical interepithelial neoplasia (Mitchell, M. F. et al., *Proceedings AACR* 39:Ab. 600, 1998). DFMO inhibited the neovascularization induced by tumor cells in vivo (Jasnis, M. A. et al., *Cancer Lett* 79:39–43, 1994). Squalene, a polyamine analogue, also inhibits angiogenesis in the rabbit cornea assay.

Other Mechanisms that Block Cell Growth or Induce Apoptosis

Transport, SSAT, and deoxyhypusine synthase are targets for developing therapies for cancer and other proliferative diseases. The potential polyamine related targets associated with cancer have not been exhausted. CHENSpm is polyamine analogue that induces apoptosis but does not function through any of the mechanisms described above (Ha, H. C. *Proc Nat.Acad.Sci USA* 94:11557–11562(1997) CHENSpm does not induce SSAT, but does reduce spermidine and spermine levels and produces a $G_2$ cell cycle arrest at subtoxic concentrations, suggesting an unusual mode of action. Polyamines are known to bind to tubulin and promote its bundling, though this is just one of several possible mechanisms by which polyamines can induce apoptosis or inhibit cell growth. For example, some microtubule associated proteins (MAPs) also bind polyamines.

Monitoring of Cancer-Related Molecules by Polyamine Analogues

Several polyamine binding anti-cancer targets could be monitored using various polyamine analogues. Acetylated polyamines, the products of the spermine/spermidine acetyltransferase (SSAT) enzymatic reaction, are substrates for the enzyme polyamine oxidase. Oxidation of acetylated polyamines produces a stoichiometric release of $H_2O_2$ which is believed to be responsible for the apoptotic response. This induction is cell type-specific and is believed to be due to the accumulation of the polyamine analogue in the cell and its possible binding to a polyamine-sensitive repressor or activator of transcription of SSAT. This repressor has not been identified, but a probe/assay for its detection would enable the synthesis of better drugs.

Membrane-Bound Proteins

Several cellular receptors have polyamine binding sites that influence receptor binding activity. Hypertension, osteoporosis, Alzheimer's disease and ischemia may all be targeted through polyamine binding receptors such as calcium receptor, N-methyl-D-aspartate (NMDA) receptors, glutamate receptors, $Ca^{2+}$ channels and several of the inwardly rectifying $K^+$ channels (Ventura, C. et al., *Am. J. Physiol.* 267H587–H592, 1994).

Polyamines in Other Diseases

Post-Angioplasty Injury

Because PAT inhibitors can contribute to inhibition of cell growth, they are viewed by the present inventors as being useful in the treatment of post-angioplasty injury. Endothelial denudation and vessel wall injury lead to neointimal hyperplasia and luminal stenosis. Inhibition of smooth muscle cell proliferation, for example, could inhibit neointimal formation. According to this invention, this initiation of cell proliferation after injury is amenable to treatment with PAT inhibitors preferably in combination with polyamine synthesis inhibitors (Takagi, M. M. et al., *Arterioscler. Thromb. Vasc. Biol.* 17:3611–3619, 1997; Nakaoka, T. et al., *J. Clin. Invest.* 100:2824–2832, 1997; Maillard, L. et al., *Cardiovasc. Res.* 35:536–546, 1997).

Hypertension $Ca^{2+}$ channels, which have high affinity binding sites for polyamines, are modulated by polyamine levels. Polyamines modulate the β-adrenergic-mediated changes in $Ca^{2+}$ levels and contractility (Ventura, C. et al., *Am. J. Physiol.* 267: H587–H592, 1994). $Ca^{2+}$ channels and binding can be measured as described for the NMDA receptor and the $K^+$-inward rectifying channels in Ventura, supra. Thus, an appropriate polyamine or analogue can be harnessed to modulate $Ca^{2+}$ in place of the channel blockers currently in use.

Osteoporosis

Blood and tissue (e.g., nerve) calcium levels are modulated by the external $Ca^{2+}$ sensing receptor (CaR) located in the parathyroid and kidney. The CaR has a specific polyamine binding site. Modulation of this receptor is believed to be a promising approach to the treatment of osteoporosis.

Alzheimer's Disease

The CaR plays a different role in the brain from that in the parathyroid. Aggregated β-amyloid protein in this disease can stimulate the CaR and eventually lead to its down-regulation. Polyamines, likewise, can bind to the CaR and inhibit CaR down-regulation stimulated by β-amyloid. Polyamines or polyamine analogues can therefore serve as protective molecules.

Immunosuppression

Low dose methotrexate is a common treatment for rheumatoid arthritis (RA). The reason for its efficacy is unknown, although it is not believed to inhibit proliferation of lymphoid cells. S-adenosylmethionine (AdoMet) metabolism has been proposed to play a direct role in its immunosuppressive activity.

The direct effect of AdoMet metabolism on the immune response is not known, though a role for polyamines has been suggested (Furumitsu, Y. et al., *J. Rheumatology,* 20:1661–1665, 1993; Nesher, G. et al., *Arthr. Rheumat.* 33:954957, 1990). Cytokines are believed to play a direct role in the pathogenesis of RA, and IL-2 is low in patients' synovial fluid, a condition which was reversed by inhibitors of polyamines (Flesher, E. et al., *J. Clin. Invest.* 83:1356–1362, 1987). The polyamine synthesis inhibitor DFMO prolongs the life of MRL-lpr/lpr mice, a model of systemic lupus erythematosus.

Polyamine levels are elevated in the urine, synovial fluid, synovial tissue, and peripheral blood mononuclear cells of RA patients. Culturing these cells in the presence of methotrexate inhibited the production of IgM-rheumatoid factor. Spermidine reversed this effect, indicating to the present inventors that a combination of polyamine synthesis inhibitors and PAT inhibitors are useful can treat autoimmune diseases. Other polyamine analogues, spergualin and deoxyspergualin, are immunosuppressive and may be beneficial for treating multiple sclerosis (Bergeron et al., *J. Org. Chem.* 52:1700, 1987; *Drug Fut.* 16:1165, 1991).

Psychiatric Disorders

A number of the compounds which the present inventors have found to inhibit PAT with high affinity, as disclosed herein, structurally resemble several known antipsychotic or antidepressant drugs.

DNA/RNA-Polyamine Hybrids for Stable Binding to Nucleic Acids

The spacing between ammonium polycations in naturally occurring polyamines (spermidine and spermine) is 3–4 carbons. This is the exact spatial separation for optimal binding to a DNA or RNA polyanionic phosphate backbone. It has been suggested that this interaction, together with the interaction with chromatin proteins, modulates gene transcription and expression. Recently, such ionic interactions have been exploited by combining polycationic 3', 5'-polyguanidine linkers bound with the base portion of the nucleosides to enhance double or triple helix formation. An oligomeric polyadenosyl RNA analogue in which the phosphodiester backbone units were replaced by cationic guanidine units was inactive, since triple strand formation was decreased (Dempcy, R. D. et al., *Proc. Natl. Acad. Sci. U.S.A.* 93:4326–4330, 1996; Goodnow, Jr., R. A. et al., *Tetrahedron Lett.* 38:3195–3198 and 3199–3202, 1997). These nucleic acid analogues melt like double helices consistent with Watson-Crick base pairing.

In this regard, this invention provides compositions and methods that incorporate complex structural substituents onto a polyamine chain to optimize the targeting of DNA or RNA for inhibiting replication, transcription or translation.

Other Polyamine-Binding Receptors as Targets

Of particular pharmacological interest are the ways in which polyamines modulate various receptor or channel functions. In particular, polyamines modulate the $Ca^{2+}$-permeable glutamate receptors assembled from subunits containing a glycine residue at the RNA editing site. The inward rectification of the $K^+$ inward rectifying channels is induced by blocking the outward current using cytoplasmic $Mg^{2+}$ (or intrinsic channel gating). This gating is due primarily to a block by cytoplasmic polyamines (Shyng-Si, et al. *Proc. Natl. Acad. Sci. USA.* 93:12014–12019, 1996). According to this invention, polyamine analogues are useful for modulating glutamate receptors that are important in ischemia, strokes, and cardiovascular disease. NMDA receptor antagonists act as anticonvulsants so that agents active at NMDA receptors are additional useful targets.

Anti-Infective Effects of Polyamine Modulation

Parasitic organisms such as *Trypanososma cruzi* are thought to obtain the polyamines necessary for their growth from their hosts rather than synthesize their own. DFMO (an ODC inhibitor), decreases the availability of putrescine, a precursor of spermidine and spermine synthesis. DFMO can cure *T. brucei* infection in mice and is active against African sleeping sickness in humans caused by *T. brucei* gambiense. DFMO also has clinical utility in *Pneumocystis carinii* pneumonia and in infection by the coccidian protozoan parasite, *Cryptosporidium*. In the laboratory, DFMO acts against *Acanthamoeba, Leishmania, Giardia, Plasmodia* and *Eimeria* (Marton, L. J. et al., *Annu. Rev. Pharmacol. Toxicol.* 35:55–91, 1995). Polyamines are also essential for the growth of *Hemophilus* and *Neisseria* organisms (Cohen, S. S., *A Guide to the Polyamines*, Oxford University Press, NY. pp 94–121, 1998). Thus, compounds and methods of the present invention can be used to treat diseases caused by *Trypanososma cruzi, T. brucei, Pneumocystis carinii, Cryptosporidium, Acanthamoeba, Leishmania, Giardia, Plasmodia, Eimeria, Hemophilus* and *Neisseria*.

Plant Pathogens

Lowering of polyamine levels may protect plants against a wide range of fungi, e.g., *Uremyces phaseoli* Linnaeus, race O. Unifoliolate (bean rust). DFMO is an effective fungicide in the following plants: tomato plants against *Verticillium* wilt fungus; wheat against stem rust fungus and powdery mild fungus; bean plants against powdery mildew fungus; Macintosh apple leaves against the powdery mildew fungus; Ogle oats against leaf rust fungus; and corn against the corn rust fungus (U.S. Pat. No. 4,818,770). The compositions of this invention that lower polyamine levels by PAT inhibition or that have other actions on systems that utilize, or are affected by, polyamines could be useful in protecting plants against a wide range of fungi.

Miscellaneous Targets

Polyamines may protect DNA from radiation damage (Newton, G. L. et al., *Radiat. Res.* 145:776–780, 1996). Therefore, an agent that raises polyamine levels, or that substitutes for an endogenous polyamine more effectively, may be a useful adjunct to radiotherapy. Polyamines may play an important role in controlling mammalian fertility (U.S. Pat. No. 4,309,442) and maintaining embryonic growth (U.S. Pat. No. 4,309,442). Other actions ascribed to polyamines include antidiarrheal, anti-peristaltic, gastrointestinal anti-spasmodic, anti-viral, antiretroviral, anti-psoriatic and insecticidal (U.S. Pat. No. 5,656,671).

The present invention also has use in: (a) cleanup of toxic or radioactive metal waste that requires specific ion-binding (this can be designed into a polyamine for use in vivo or environmentally); (b) image-enhancement in medical imaging systems such as X-ray, computer-assisted tomography or magnetic resonance technologies; (c) enzyme-like catalysis that is required in asymmetric organic synthesis or resolution; (d) xenobiotic detoxification; and (e) nucleosidase activities.

Combination Therapy

Certain agents inhibit growth of tumor cells in culture in a manner that is additive with cytotoxic drugs. The agent 8-chloro-cAMP (8-Cl-cAMP) (Tortora et al., *Cancer Res.* 57:5107–5111, 1997) is a cAMP analogue that selectively down-regulates PLA-1, a signaling protein that is directly involved in cell proliferation and neoplastic transformation and that mediates the mitogenic effects of certain oncogenes and growth factors. In nude mice bearing human GEO colon cancer xenografts, 8-Cl-cAMP inhibited tumor angiogenesis and secretion of growth factors of the EGF family and synergized with anti-EGF receptor antibodies in inhibiting tumor growth. 8-Cl-cAMP acts by different mechanisms than do the polyamine analogues of this invention.

The PAT inhibitors of the present invention can be used alone, in combination with 8-Cl-cAMP, or in combination with an ODC inhibitor and/or a SAM decarboxylation inhibitor (with or without 8-Cl-cAMP). Because polyamine modulation affects chromatin structure, other agents can be used in combination with the PAT inhibitors of this invention include topoisomerase inhibitors, DNA alkylating agents and DNA intercalating agents such as doxorubicin, adriamycin, chlorozotocin, etc.

Citation of the above documents is not intended as an admission that any of the foregoing is pertinent prior art. All statements as to the date or representation as to the contents of these documents is based on the information available to the applicant and does not constitute any admission as to the correctness of the dates or contents of these documents.

SUMMARY OF THE INVENTION

The present invention is directed to a series of polyamine analogues or derivatives and their use as drugs, as agricultural or as environmentally useful agents. The invention defines sites and structures within these compounds that are key to their binding (and polyamine binding) to membrane (and soluble proteins), particularly the PATr.

The compositions of the present invention include polyamine derivatives substituted at one or more positions. Disubstituted polyamines are preferably substituted at the two terminal nitrogens, but may be alternatively or additionally substituted at internal nitrogen and/or internal carbon atoms.

A preferred embodiment is a highly specific PAT inhibitor with pharmaceutical utility as an anti-cancer chemotherapeutic. Preferred compounds with such activity include $N^1$-dansylspermine (also termed monodansylspermine or MDS (1), $N^1$-dansylspermidine (also termed monodansylspermidine or MDSd, $N^1$-[($N^6$-dansyl)-6-aminocaproyl] spermine (termed DACS, 4), $N^1$-[($N^6$-dansyl)-6-aminocaproyl]spermidine (DACSd), $N^1$-[($N^6$–5-(4-chlorobenzamidomethyl)-thiophene-2-sulfonyl)-6-aminocaproyl]spermine 5 or $N^1$-[($N^6$-(2-dibenzofuransulfonyl)-6-aminocaproyl]spermine 6. The latter two compounds have surprisingly high binding and inhibitory activity compared to the corresponding compounds lacking the C6 caproyl spacer between the aryl group and the polyamine. For this reason, DACS 4 and DACSd, and compounds 5 and 6 are preferred pharmaceutical compositions. Use of alternate spacers (or linkers or couplers) and other aryl or heterocyclic "head" groups, all of which are disclosed herein, is expected to yield even more potent PAT inhibitors.

Preferred substituents are structures that increase binding affinity or otherwise enhance the irreversibility of binding of the compound to a polyamine binding molecule, such as the PATr, an enzyme or DNA. Such additional substituents include the aziridine group and various other aliphatic, aromatic, mixed aliphatic-aromatic, or heterocyclic multiring structures. Reactive moieties which, like aziridine, bind irreversibly to a PATr or another polyamine binding molecule, are also within the scope of this invention. Examples of reactive groups that react with nucleophiles to form covalent bonds include chloro-, bromo- and iodoacetamides, sulfonylfluorides, esters, nitrogen mustards, etc. Such reactive moieties are used for affinity labeling in a diagnostic or research context, and subserve pharmacological activity as sites within a drug that inhibit PAT or polyamine synthesis. The reactive group can be a reactive photoaffinity group such as an azido or benzophenone group. Chemical agents for photoaffinity labeling are well-known in the art (Flemming, S. A., *Tetrahedron* 51:12479–12520, 1995). Photoreactive compounds for cancer treatment are also known in the art.

Specifically, a composition which is a polyamine analogue or derivative that binds to a polyamine-binding site of a molecule and/or inhibits polyamine transport, which composition has the formula

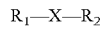

wherein
$R_1$ is H, or is a head group selected from the group consisting of a straight or branched $C_{1-10}$ aliphatic, alicyclic, single or multring aromatic, single or multiring aryl subsituted aliphatic, aliphatic-substituted single or multiring aromatic, a single or multiring heterocyclic, a single or multiring heterocyclic-substituted aliphatic and an aliphatic-substituted aromatic;
$R_2$ is a polyamine; and
X is CO, NHCO, NHCS, or $SO_2$ In another embodiment of the above composition, $R_2$ has the formula $NH(CH_2)_nNH(CH_2)_pNH(CH_2)_qNHR_3$ wherein
(a) n, p and q vary independently and n=p=q=1 to 12;
(b) $R_3$ is H; $C_{1-10}$ alkyl; $C_{1-10}$ alkenyl; $C_{-10}$ alkynyl; alicyclic; aryl; aryl-substituted alkyl, alkenyl or alkynyl; alkyl-, alkenyl-, or alkynyl-substituted aryl; gauanidino; heterocyclic; heterocyclic-substituted alkyl, alkenyl or alkynyl; and alkyl-, alkenyl-, or alkynyl-substituted heterocyclic.

The above composition may further comprise, linked between X and $R_2$, a linker L and an additional group y, such that said composition has the formula:

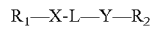

wherein,
L is a $C_{1-10}$ alkyl, $C_{1-10}$ alkenyl, $C_{1-10}$ alkynyl, alicyclic, or heterocyclic;
X is CO, $SO_2$, NHCO or NHCS; and
Y is CONH, $SO_2NH$, NHCO, NHCONH, NHCSNH, $NHSO_2$, $SO_2$, O, or S.

In the foregoing compositions $R_1$ can have the formula:

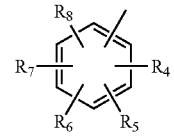

wherein
$R_4$, $R_5$, $R_6$, $R_7$ and $R_8$ are, independently, H, OH, halogen, $NO_2$, $NH_2$, $NH(CH)_nCH_3$, $N((CH)_nCH_3)_2$, CN, $(CH)_nCH_3$, $O(CH)_nCH_3$, $S(CH_2)_nCH_3$, $NCO(CH_2)_nCH_3$, $O(CF_2)_nCF_3$, or $CO—O(CH)_nCH_3$ where n=0 to 10;

Alternatively, $R_1$ has the formula:

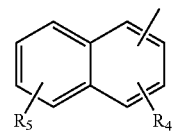

wherein
$R_4$ and $R_5$ are, independently, H, OH, halogen, $NO_2$, $NH_2$, $NH(CH)_nCH_3$, $N((CH)_nCH_3)_2$, CN, $(CH)_nCH_3$, $O(CH)_nCH_3$, $S(CH_2)_nCH_3$, $NCO(CH_2)_nCH_3$, $O(CF_2)_nCF_3$, or $CO—O(CH)_nCH_3$, where n=0 to 10;

In yet another embodiment, $R_1$ has the formula:

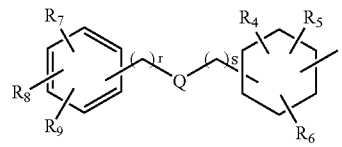

wherein
r and s vary independently and r=s=0 to 6;
$R_4$, $R_5$, $R_6$, $R_7$, $R_8$ and $R_9$ are, independently, H, OH, halogen, $NO_2$, $NH_2$, $NH(CH)_nCH_3$, $N((CH)_nCH_3)_2$, CN, $(CH)_nCH_3$, $O(CH)_nCH_3$, $S(CH_2)_nCH_3$, $NCO(CH_2)_nCH_3$, $O(CF_2),CF_3$, or $CO—O(CH)_nCH_3$ where n=0 to 10; and Q is CONH, SO$_2$NH, NHCO, NHCONH, NHCSNH, NHSO$_2$, SO$_2$, O, or S.

Furthermore, R$_1$ may have the formula:

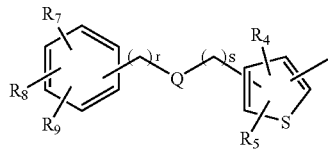

wherein
  r and s vary independently and are 0 to 6;
  R$_4$, R$_5$, R$_6$ and R$_7$ are, independently, H, OH, NO$_2$, NH$_2$, NH(CH)$_n$CH$_3$, N((CH)$_n$CH$_3$)$_2$, CN, (CH)$_n$CH$_3$, O(CH)$_n$CH$_3$, S(CH$_2$)$_n$CH$_3$, NCO(CH$_2$)$_n$CH$_3$, O(CF$_2$)$_n$CF$_3$, or CO—O(CH)$_n$CH$_3$ where n=0 to 10; and
  Q is CONH, SO$_2$NH, NHCO, NHCONH, NHCSNH, NHSO$_2$, SO$_2$, O, or S.

In the foregoing compositions, R$_1$ may be selected from the group consisting of naphthalene, phenanthrene, anthracene, pyrene, dibenzofuran, acridine, 2,1,3-benzothiodiazole, quinoline, isoquinoline, benzofuran, indole, carbazole, fluorene, 1,3-benzodiazine, phenazine, phenoxazine, phenothiazine, adamantane, camphor, pipiridine, alkylpiperazine, morpholine, cyclopropyl, cyclobutyl, cyclopentyl, cyclohexyl, cycloheptyl, cyclooctyl, thiophene, furan, pyrrole, alkyl-1,2-diazole, alkylimidazole, alkyl-1H-1,2,3-triazol, alkyl-1H1,2,3,4-tetrazole, thiazole, oxazole, 1,3,4-thiadiazole, pyridinyl, pyrimidine, 1,2-diazine, 1,4-diazine and 1,3,5-triazine, 4-dimethylaminoazobenzene, 3-phenyl-5-methylisooxazole, 3-(2-chlorophenyl)-5-methylisooxazole, 2-(4-chlorpheny)-6-methyl-7-chloroquinoline, 6-chloroimidazo[2,1-β]thiazole, α-methylcinnamic acid, and 2-[1,2-dihydro-2H-1,4-benzodioxepinyl]thiazole.

R$_1$ may also be a D- or L-amino acid.

Also provided is the above composition where R$_1$ has a formula selected from the group consisting of

 (A)

 (B)

(C)

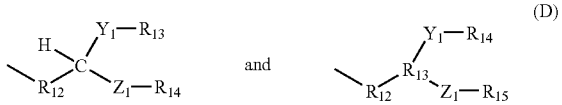 (D)

wherein
  R$_{12}$ and R$_{13}$, independently, are H, naphthalene, phenanthrene, anthracene, pyrene, dibenzofuran, acridine, 2,1,3-benzothiodiazole, quinoline, isoquinoline, benzofuran, indole, carbazole, fluorene, 1,3-benzodiazine, phenazine, phenoxazine, phenothiazine, adamantane, camphor, pipiridine, alkylpiperazine, morpholine, cyclopropyl, cyclobutyl, cyclopentyl, cyclohexyl, cycloheptyl, cyclooctyl, thiophene, furan, pyrrole, alkyl-1,2-diazole, alkylimidazole, alkyl-1H-1,2,3-triazol, alkyl-1H1,2,3,4-tetrazole, thiazole, oxazole, 1,3,4-thiadiazole, pyridinyl, pyrimidine, 1,2-diazine, 1,4-diazine and 1,3,5-triazine, 4-dimethylaminoazobenzene, 3-phenyl-5-methylisooxazole, 3-(2-chlorophenyl)-5-methylisooxazole, 2-(4-chloropheny)-6-methyl-7-chloroquinoline, 6-chloroimidazo[2,1-β]thiazole, α-methylcinnamic acid, or 2-[1,2-dihydro-2H-1,4-benzodioxepinyl]thiazole; and further,
  wherein a ring of R$_{12}$, R$_{13}$ or both in formulas (A), (B) and (D), is optionally substituted with one or more of OH, halogen, NO$_2$, NH$_2$, NH(CH)$_n$CH$_3$, N((CH)$_n$CH$_3$)$_2$, CN, (CH)$_n$CH$_3$, O(CH)$_n$CH$_3$, S(CH$_2$)$_n$CH$_3$, NCO(CH$_2$)$_n$CH$_3$, O(CF$_2$)$_n$CF$_3$, or COO(CH)$_n$CH$_3$, where n=0 to 10;
  R$_{14}$ and R$_{15}$, and, in formula (C), R$_{13}$, independently, are (CH$_2$)$_n$, (CH$_2$)$_n$CH=CH, (CH$_2$)$_n$(CH=CH)$_m$CO, or (CH$_2$)$_n$CO where n=0 to 5 and m=1 to 3;
  Y$_1$ and Z$_1$, independently, are CONH, SO$_2$NH, NHCO, NHCONH, NHCSNH, NHSO$_2$ NHSO$_2$, SO$_2$, NHSO$_2$, SO$_2$, O, S, COO or
  when R$_1$ is of formula (A) or (B), Y$_1$ represents a bond between a C or N atom of R$_{12}$ and a C or N atom of R$_{13}$ and Z$_1$ represents a bond between a C or N atom of R$_{13}$ and a C or N atom of R$_{14}$; or
  when R$_1$ is of formula (C) or Y$_1$ represents a bond between the C and a C or N atom of R$_{13}$ and Z$_1$ represents a bond between the C and a C or N atom of R$_{14}$; or
  when R$_1$ is of formula (D) Y$_1$ represents a bond between a C or N atom of R$_{12}$ and a C or N atom of R$_{14}$ and Z$_1$ represents a bond between a C or N atom of R$_{13}$ and a C or N atom of R$_{15}$ In the above compositions, R$_2$ preferably has the formula

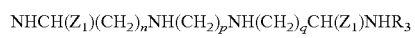

wherein
  (a) n, p and q vary independently and n=q=1 to 12;
  (b) R$_3$ is H; C$_{1-10}$ alkyl; C$_{1-10}$ alkenyl; C$_{1-10}$ alkynyl; alicyclic; aryl; aryl-substituted alkyl, alkenyl or alkynyl; alkyl-, alkenyl-, or alkynyl-substituted aryl; gauanidino or heterocyclic; and
  (c) Z$_1$ is CH$_3$, CH$_2$CH$_3$ or cyclopropyl.

In another embodiment, R$_2$ has the formula:

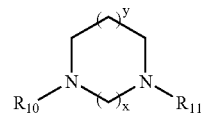

wherein
  x=1 to 4; y=1 to 3,
  R$_{10}$ and R$_{11}$, are, independently, H, (CH$_2$)$_n$NHR$_{12}$ or (CH$_2$)$_k$NH(CH$_2$)$_l$NHR$_{12}$
  where n=k=l=1 to 10, and R$_{12}$ is H or C(N=H)NH$_2$ In the above compositions, R$_2$ is preferably seleccted from the group consisting of N$^1$-acetylspermine, N$^1$-acetylspermidine, N$^8$-acetylspermidine, N$^1$-guanidinospermine, cadaverine, aminopropylcadaverine, homospermidine, caldine (horspermidine), 7-hydroxyspermidine, thermine (norspermine), thermospermine, canavalmine, aminopropylhomospermidine, N, N'-bis(3-aminoppropyl)cadaverine, aminopentylnorspermidine, N$^4$-aminopropylnorspermidine, N$^4$-aminopropylspermidine, caldopentamine, homocaldopentamine, N$^4$-bis(aminopropyl)norspermidine, thermopentamine, N$^4$-bis(aminopropyl)spermidine, caldohexamine, homothermohexamine, homocaldohexamine, N-(3-aminopropyl)-1,3-propanediamine, N,N'-bis(3-aminopropyl)ethylendiamine, N,N'-bis(3-aminopropyl)-1,4-piperazine, N,N'-bis(3-aminopropyl)-1,3-piperazine, N,N'-bis(3-aminopropyl)-1,3-propanediamine, N,N'-bis(2-aminoethyl)-1,3-propanediamine, tris(3-aminopropyl)amine, and tris(aminoethyl)amine Preferred compositions are polyamine analogues selected from the group consisting of compounds designated herein 3, 4, 5, 6, 13, 14, 29, 40, 43, 44, 45, 57, 58, 56, 66, 67, 72, 76, 84, 88, 89, 95 and 96, most preferably, compound 4, 5, 6, 43, 65, 66, 84, 89, 95 or 96.

$R_1$ or $R_3$ may be bonded at one or more sites to a reactive moiety that is capable of forming covalent bonds with a nucleophilic site on a target molecule, such as a protein or a nucleic acid, preferably a cellular receptor or other cell surface molecule. Such composition permit esssentially irreversible binding that is advantageous in both diagnostic and therapeutic uses.

The present invention is also directed to a pharmaceutical composition useful for treating a disease or condition in which the inhibition of polyamine transport is desirable, comprising a composition as described above and a pharmaceutically acceptable excipient. The pharmaceutical composition may further include a an inhibitor of polyamine synthesis; preferably DFMO. Other combinations include the above pharmaceutical composition and one or more additional agents known to be useful for treating said disease or condition This invention also provides a method for treating a disease or a condition in a subject associated with undesired cell proliferation and/or which is treatable by inhibition of polyamine transport, comprising adminstering to said subject an effective amount of a pharmaceutical compsition as described above. The undesired cell proliferation may be associated with proliferation of cells of the immune system, cell of the vascular neontima, tumor cells or with undesired angiogenesis. Preferred diseases to be treated as above include cancer or post-angioplasty injury.

The present invention is directed to a series of polyamine analogues useful in an improved assay of polyamine uptake into the cell or polyamine binding to specific ligands. The invention identifies elements that are key for polyamine binding to membrane proteins such as the PATr (PATr), and to soluble-proteins, and which can be monitored through this technique.

Disubstituted polyamines, preferably having a reactive group at one end, may also be employed as assay or biochemical probes.

A preferred assay method employs a monosubstituted polyamine probe having a moiety that serves as a detectable label (a "reporter"), preferably a fluorophore, most preferably the dansyl group, or another substituent that can be detected through a variety of means, including by ELISA. A preferred assay method employs a polyamine or analogue immobilized to a solid support.

Additional substituents which may be present on the polyamine core (with or without the reporter group), are structures which increase binding affinity, or otherwise enhance the irreversibility of binding of the compound to a polyamine binding molecule, such as a PATr, an enzyme or DNA. Such additional substituents include the aziridine group and various other aliphatic, aromatic or heterocyclic multi-ring structures. A reactive moiety, which, like aziridine, can bind irreversibly to a PATr or another polyamine binding molecule is also contemplated. Examples of groups which react with nucleophiles to form covalent bonds include chloro-, bromo- and iodoacetamides, sulfonylfluorides, esters, nitrogen mustards, etc. Such reactive moieties are used for affinity labeling in a diagnostic or research context, and subserve pharmacological activity as parts of drugs that inhibit PAT or polyamine synthesis. The reactive group can also be a reactive photoaffinity group such as an azido- and benzophenone group. Chemical reagents in photoaffinity labeling are well-known (Flemming, S. A., *Tetrahedron* 51:12479–12520, 1995). Moreover, photoreactive compounds for cancer treatment are known in the art.

The present invention includes a high throughput screening assay which allows processing of high numbers of potential target compounds that are being screened for activity as inhibitors, preferably competitive inhibitors, of PAT. The method is suited to the 96 well microplate format for use with robotic sample and plate handling systems known in the art. The means for detecting transport are a function of the detectable label used. Fluorescence and chemiluminescence are the methods of choice. The present invention also encompasses a unique pharmacophore for a polyamine binding site that can be used to isolate a polyamine binding target or to assay the conformational state of a selected target by its binding.

Also provided is an enzymatic assay which permits amplification of the signal, wherein biotin or some other "reporter" is conjugated to the polyamine as the "detectable label," and is detected by allowing the binding of streptavidin conjugated to an enzyme, followed by generation of a colored product of the enzyme from a chromogenic substrate. Also included is a composition in which both biotin and a "hapten" group recognized by an antibody are coupled to a polyamine. In another composition the hapten is coupled directly to the enzyme. This compound can be captured by an antibody specific for the hapten and detected by the biotin interacting with streptavidin-enzyme complex as above. Alternatively, streptavidin can be used for capture and the antibody for detection. In either case, signal amplification permits a significant increase in sensitivity.

Specifically, the diagnostic or assay composition is designed to be used in an assay of polyamine transport or polyamine binding, and comprises a polyamine analogue as set forth above, that is detectably labeled and/or includes at least one reporter group capable of detection. Preferably the analogue comprises a linker group L between the reporter group and said polyamine.

As indicated above, a preferred reporter group is a fluorophore, a chromophore or a luminescer, most preferably dansyl or biotinyl; the polyamine is preferably spermine, spermidine or putrescine. Most preferred for this utilityis monodansylspermine or DACS.

The diagnostic composition may also include as a single, or as one of several reporter groups, a hapten recognized by an antibody.

The above diagnostic compositions may have the polyamine analogue bound to an enzyme.

In preferred embodiment, the polyamine analogue is immoblized to a solid support.

An assay method provided herein for detecting polyamine transport comprises (a) incubating cells with a composition as above; and (b) detecting the presence of said reporter group in said cells. When applied in a screening assay to identify unknown compounds for their binding to a polyamine binding site or their entry into a cell via a polyamine transporter, the assay comprises (a) incubating molecules or cells having a polyamine binding site or cells having a polyamine transporter with (i) a polyamine analogue of any of claims 26–33, (ii) with and without said unknown compound; (b) measuring the quantity of said reporter bound to said cells or molecules or internalized in said cells; and (c) comparing the amount of reporter bound or internalized in the presence of said unknown compound to the amount of reporter bound or internalized in the absence of said unknown compound, wherein a reduction in the amount of said reporter detected is measure of the binding or transport of said unknown compound.

The methods of the present invention include high throughput solid phase synthesis of a polyamine library. This library includes the attributes of a solid phase support, a cleavable linker that attaches the molecule to the support, the addition of extenders that are a series of protected aldehydes, amino acids, etc., that can be coupled and subsequently reduced to amines through reductive amidation, and a variety of terminator molecules. This combination allows for the synthesis of a large variety of novel analogues that can be used for many of the targets and assays described herein.

BRIEF DESCRIPTION OF THE DRAWINGS

FIG. 2 (sheets 2/1 to 2/10) is a tabular representation of a large number of chemical structures 3–98 that were tested for their effects on cell growth. R, an index of growth inhibitory activity, is the ratio of the growth of cells in the presence of the test compound to the growth in the presence of the compound plus DFMO. The $K_i$, (inhibition constant) reflects a compound's inhibition of PAT in cell culture. These biological effects provide a basis for SAR analysis.

FIG. 10 shows four classes (111–114) of conformationally restricted polyamine analogues, and at the bottom, a stereochemically defined, internally cyclic polyamine analogues (116).

FIG. 15 shows examples of spacers or linkers for use with multiring head group (135–139).

FIG. 16 shows a series of compounds (140–147) containing multiple ring head groups.

FIG. 25 shows a group of chemical structures (161–165) including three known psychoactive compounds trifluoperazine 163, thorazine 164 and imipramine 165. Compounds 161, 162 and 165 inhibited polyamine transport.

FIG. 31 is a schematic illustration showing the possible sites for modifying a polyamine to create an "immobilization handle" and a "reporter handle" combination.

FIG. 40 shows various linkers used in a multipin method of dimensionally stable polypropylene polyethylene pins to which a graft polymer is covalently linked. The Rink amide linker is shown as structure 23a coupled to the FIG. 41 shows a compound that is synthesized using a solid support and the synthetic approach described for FIGS. 4 and 5. Compound 31 is synthesized using the blocked 3-aminopropanal 27a as the first extender, benzaldehyde 28a as the first terminator, the blocked methioninal 29a as the second extender and acetone as the final terminator.

DESCRIPTION OF THE PREFERRED EMBODIMENTS

Figure 1:
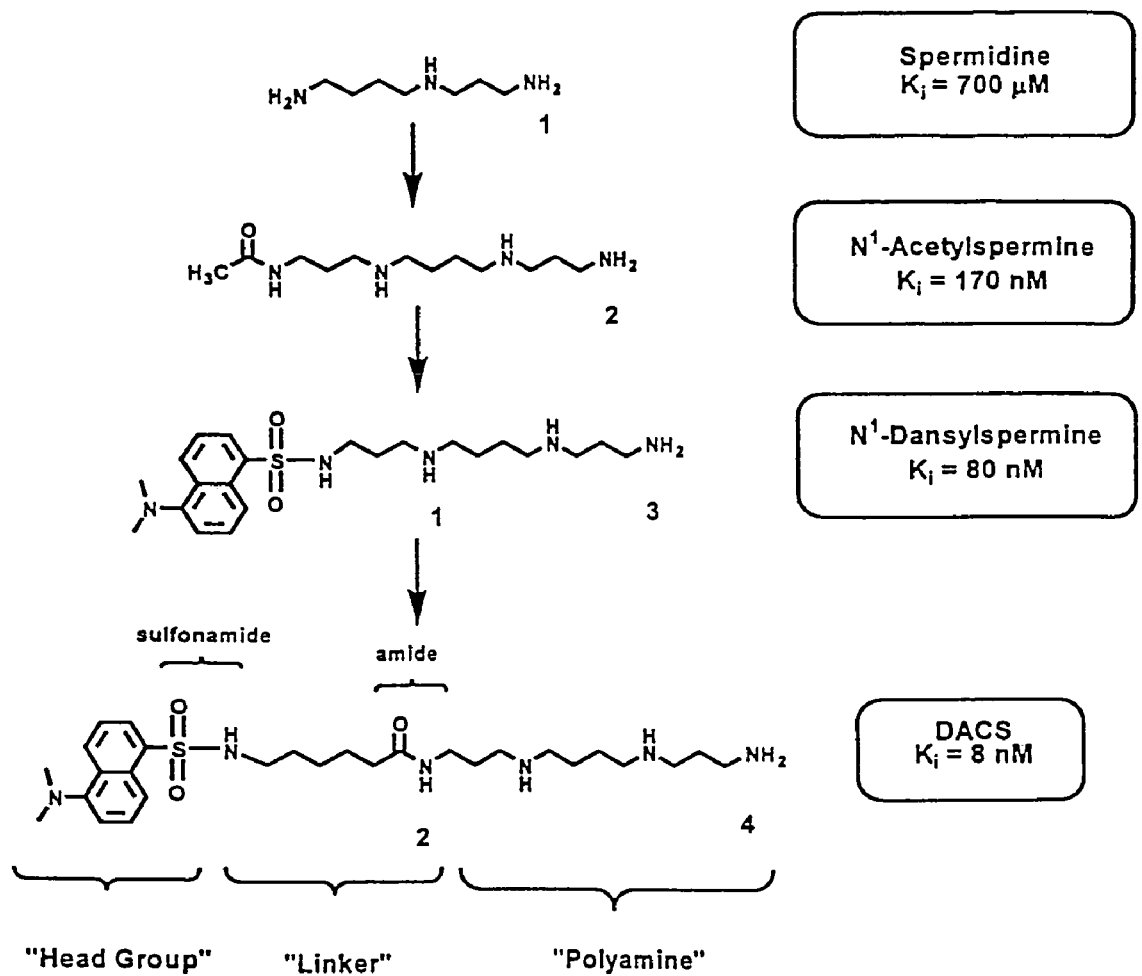
FIG. 1 shows the structure and activity relationships (SAR) between spermidine, MDS and DACS. $K_i$ values are the inhibitory constants obtained in a PAT inhibition assay.

The present inventors have designed novel compounds for therapeutic uses and have devised tests using such compounds as probes for measuring PAT and polyamine binding in an efficient, high throughput assay. Using the novel methods, they have screened for and discovered compounds with high affinity for the PATr that inhibit uptake, both competitively and non-competitively. Such compounds are useful as drugs in a number of diseases, particularly cancer. They can also be used as a component of novel drug combinations with, for example, a polyamine synthesis inhibitor such as DFMO (which inhibits ornithine decarboxylase) or with other agents. The compounds of the present invention are also useful in other diseases or conditions in which polyamines play a role as described above, and have agricultural and environmental uses.

The inventors found that various chemical groups can be attached to a polyamine to give it advantageous properties as an inhibitor of PAT or as a probe in an assay of PAT and for drug screening. Such chemical modification does not destroy the effective binding and, in fact, enhances the affinity of the derivatized polyamine for the PATr. Hence, these compounds are useful for discovery of inhibitors of polyamine uptake.

Definitions

As used herein, the term "polyamine" is intended to mean putrescine, spermine or spermidine, as well as longer linear polyamines, branched polyamines, and the like, which may have between 2 and about 10 nitrogens. Also included in this definition are polyamine derivatives or analogues comprising a basic polyamine chain with any of a number of functional groups bound to a C atom or a terminal or internal N atom. A polyamine derivative may include a terminal linker or spacer group between the polyamine core and a derivatizing function.

A "head group" is defined as a moiety bonded either directly to the polyamine or attached to a linker that is bonded to the polyamine. It is preferably an aromatic or heterocyclic group, although aliphatic groups or aroalkyl groups are included. Thus, a head group may be a fluorescent moiety, which also serves as a "reporter."

An "inhibitor" moiety or group is a chemical group derivatizing a polyamine that (1) causes the derivative to bind to the PATr with higher affinity than does a native polyamine and/or (2) by other means blocks the uptake of a polyamine (or a probe of this invention) into a cell or a subcellular PATr preparation. The inventors disclose herein compounds that efficiently inhibit PAT in MDA-MB-231 human breast carcinoma cell and other cells. A number of different types of such inhibitors have been synthesized; various of the synthetic schemes are disclosed herein.

A "reporter moiety" is a chemical moiety forming part of a probe which renders the probe detectable (either directly or, for example, through enzymatic enhancement) and hence permits the determination of the activity of the PATr to which the probe binds. A reporter is detectable either because it itself emits a detectable signal, or by virtue of its affinity for a reporter-specific partner which is detectable or becomes so by binding to, or otherwise reacting with, the reporter. In a preferred embodiment the polyamine analogue is immobilized to a solid support which enables removal of the analogue and any interacting/binding molecules from a complex mixture.

Overview of Structure-Activity Relationships (SARs)

The PAT inhibitors were developed by modification of the natural substrate of the transporter, spermidine. The present inventors discovered that introduction of a 3-amidopropyl group to the diaminobutyl part of spermidine produced a significantly better transport inhibitor as shown in FIG. 1. The optimal amido or sulfonamide substituent was found to be a medium sized aromatic group, leading to the invention of $N^1$-dansylspermine (MDS) as both a transport inhibitor and a transport assay reporter molecule. MDS has increased binding affinity to cells compared to spermidine and $N^1$-acetylspermine. Significantly enhanced inhibition of cell growth and PAT resulted from the introduction of a 6-carbon atom linker between the aromatic "head" group of MDS and the polyamine core. This new molecule, $N^1$-[($N^6$-dansyl)-6-aminocaproyl]spermine (or DACS) 4, is one of the most potent PAT inhibitors known. In its interaction with biological systems, DACS shows many of the desired properties set forth above. The present inventors have studied DACS and other related analogues extensively.

The SARs around DACS 4 as a lead compound have been explored extensively as shown in FIG. 2 (in particular, compounds 73–98). As discussed above, changes were made in each of several regions of DACS, and effects on transporter binding were measured. The impact of changing the aromatic "head" group was explored by synthesizing a number a different activated 4-nitrophenyl esters with different aromatic and non-aromatic N-sulfonamides at the distal amino end. Another series of "headless" analogues were synthesized to explore the importance of the hydrophobic aromatic grouping. In sum, the present inventors have designed and synthesized a large number of compounds that efficiently inhibit PAT. As described herein, all mono, di and multi-substituted polyamines with the various substituents are intended for use as drugs.

A. $N^1$-Substituted Polyamine Analogues

Figure 3:
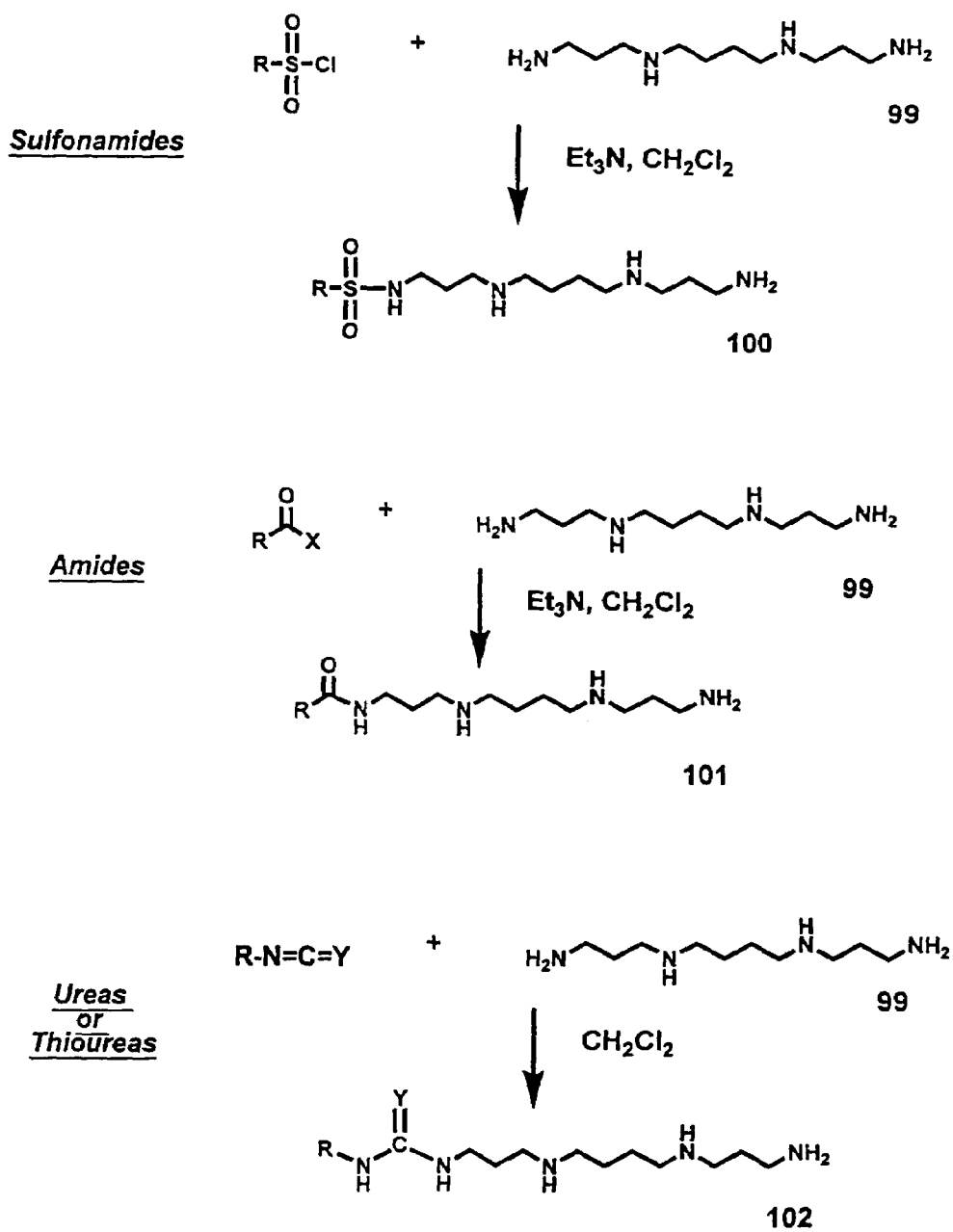
FIG. 3 shows synthetic routes to N'-substituted polyamine analogues 99–102.

A series of inhibitors was made by direct reaction of a polyamine with a sulfonyl chloride, acyl, isocyanate, isothiocyanate, alkyl chloride or an N-hydroxysuccinamide-activated carboxy ester as described in FIG. 3 and in Examples I–IV. Different head groups, linkages and polyamines were combined. Many of the Figures show spermine as a nonlimiting example of the polyamine core of the molecule.

The polyamine core can be varied as defined above. The synthesis of $N^1$-(1-pyrenylsulfonyl)spermine 15 from spermine and 1-pyrenesulfonyl chloride (FIG. 5) is described in detail in Example II.

The synthesis of $N^1$-((1-carbonyl)-4-(1-pyrenyl)butane) spermine 7, from spermine and pyrenebutyric acid (FIG. 6) illustrates the use of 1-(3-dimethylaminopropyl)-3-ethylcarbodiimide hydrochloride (or EDAC) to form, in situ, the activated N-hydroxysuccinimide ester of a carboxylic acid.

This one-step method produces the amide analogues of polyamines (see Example III). The synthesis of N-(1-anthracenyl)-N'-(N¹-spermidyl)urea 9 from 1-aminoanthracene and spermine (FIG. 4) is described in more detail in Example IV. This illustrates the synthesis of ureas by activated urethanes as intermediates. Urea derivatives can also be synthesized using substituted isocyanates. For example, 1-aminoanthracene is first activated with p-nitrophenyl chloroformate to form the urethane which is reacted with spermine to yield a substituted urea 9. The synthesis of N—(N1-spermidyl)-2-(naphthyl)acetamide 103, N—(N¹-spermidyl)-2-(naphthoxy)acetamide 104 and O-(fluorenylmethyl)-N-(N1-spermidyl)urethane 105 are described in Example V–VII, respectively.

Figure 4:
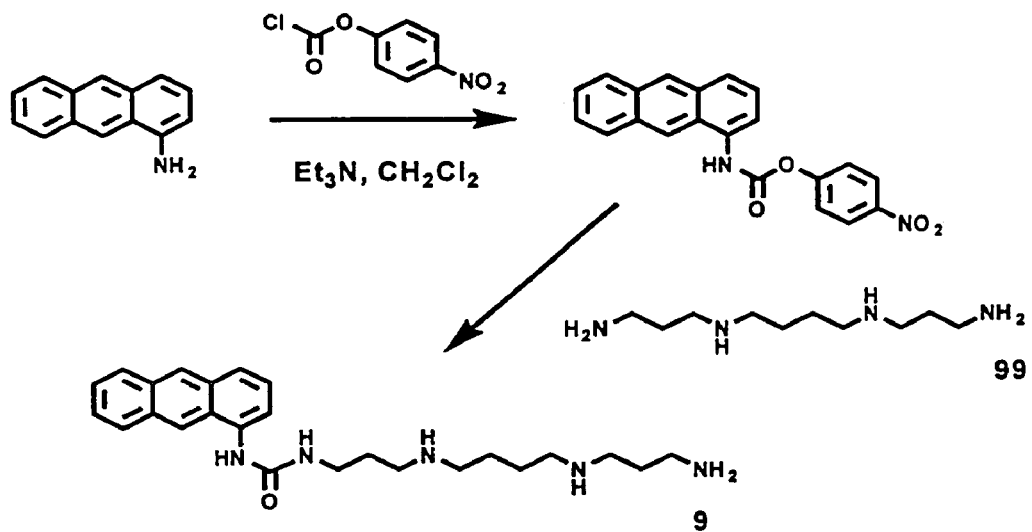
FIG. 4 is a scheme of the synthesis of N-(1-anthracenyl)-N'-(N¹-spermidyl)urea 9
Figure 5:
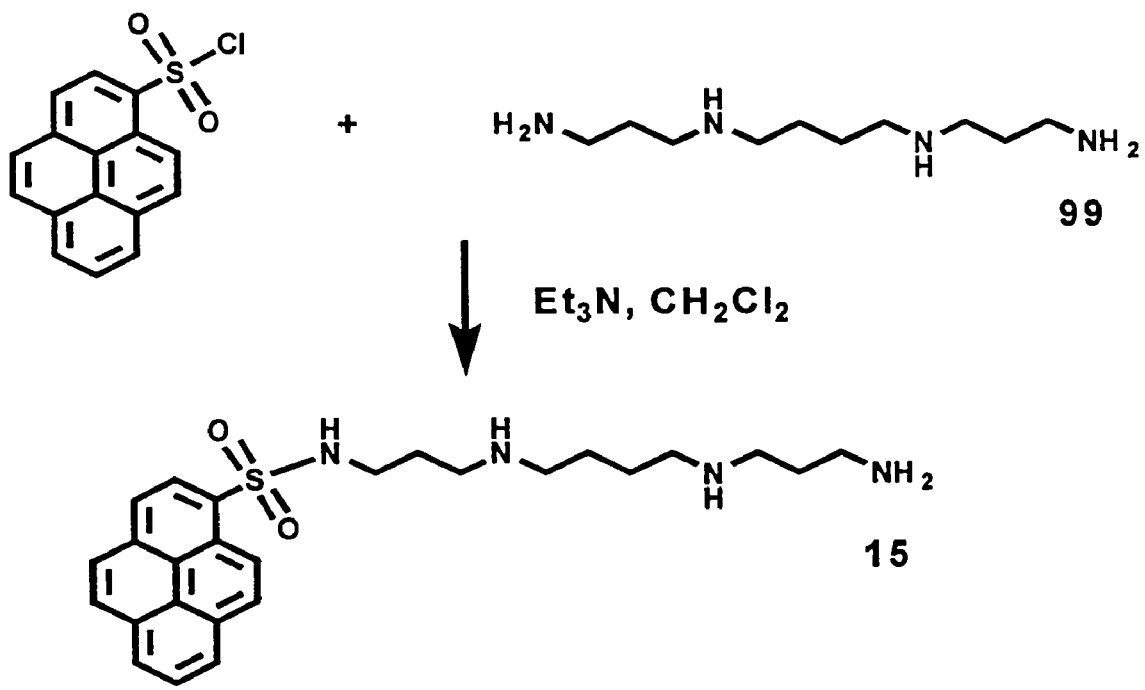
FIG. 5 is a scheme of the synthesis of $N^1$-(1-pyrenylsulfonyl)spermine 15

The best PAT inhibitors of this group have spermine as the polyamine core and include a head group such as pyrenyl (see FIG. 5; Example II (15)), 5-(4-chlorobenzamidomethyl) thiophenenyl (13) or dansyl (3) (FIG. 7; Example I). These three compounds inhibit the PATr with $K_i$'s of 91, 58 and 80 nM, respectively. A head group can also be attached to spermine via an amide bond as illustrated by compound 14, resulting in a $K_i$ of 37 nM. Inhibitors of this type typically have $K_i$ values of approximately 100 nM and R values in the MDA growth assay of >1. However, when spermine was substituted with N-(3-aminopropyl)-1,3-propanediamine, N,N'-bis-(3-aminopropyl)ethylenediamine, N,N'-bis(3-aminopropyl)piperazine, N,N'-bis(3-aminopropyl)-1,3-propanediamine, N,N'-bis(2-aminoethyl)-1,3-propanediamine, tris(3-aminopropyl)amine or tris(2-aminoethyl)amine, the $K_j$ values in the polyamine transport assay were above 200 nM. Such less inhibitory compounds are omitted from FIG. 2 (which lists compounds 3–98). The synthesis of these types of compounds is exemplified in FIGS. 4–7 (Examples I–IV).

The Examples illustrate a key point regarding the synthetic methods. In Example I, the polyamine in $CH_2Cl_2$ solvent was treated dropwise to a solution of the acid chloride in the same solvent. This gave a statistical mixture of the unsubstituted, monosubstituted and disubstituted polyamine derivatives, which is advantageous because purification by the methods described herein resulted in pure mono- and di-substituted derivatives. Each analogue was then tested in the biological assays (PAT inhibition and cell growth inhibition). It was sometimes an advantage to produce an individual mono-substituted derivative using a mono-protected polyamine intermediate. Large-scale (>5 grams) production of the analogues was accomplished in this fashion because removal of side products was greatly facilitated.

Figure 8:
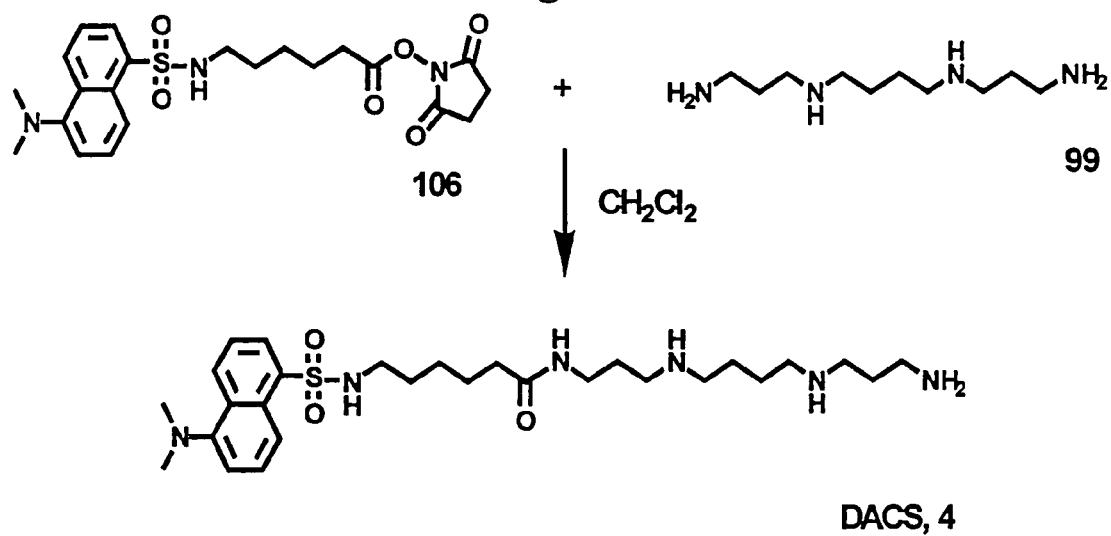
FIGS. 8 and 9 each show a different synthetic scheme for the synthesis of DACS.
Figure 9:
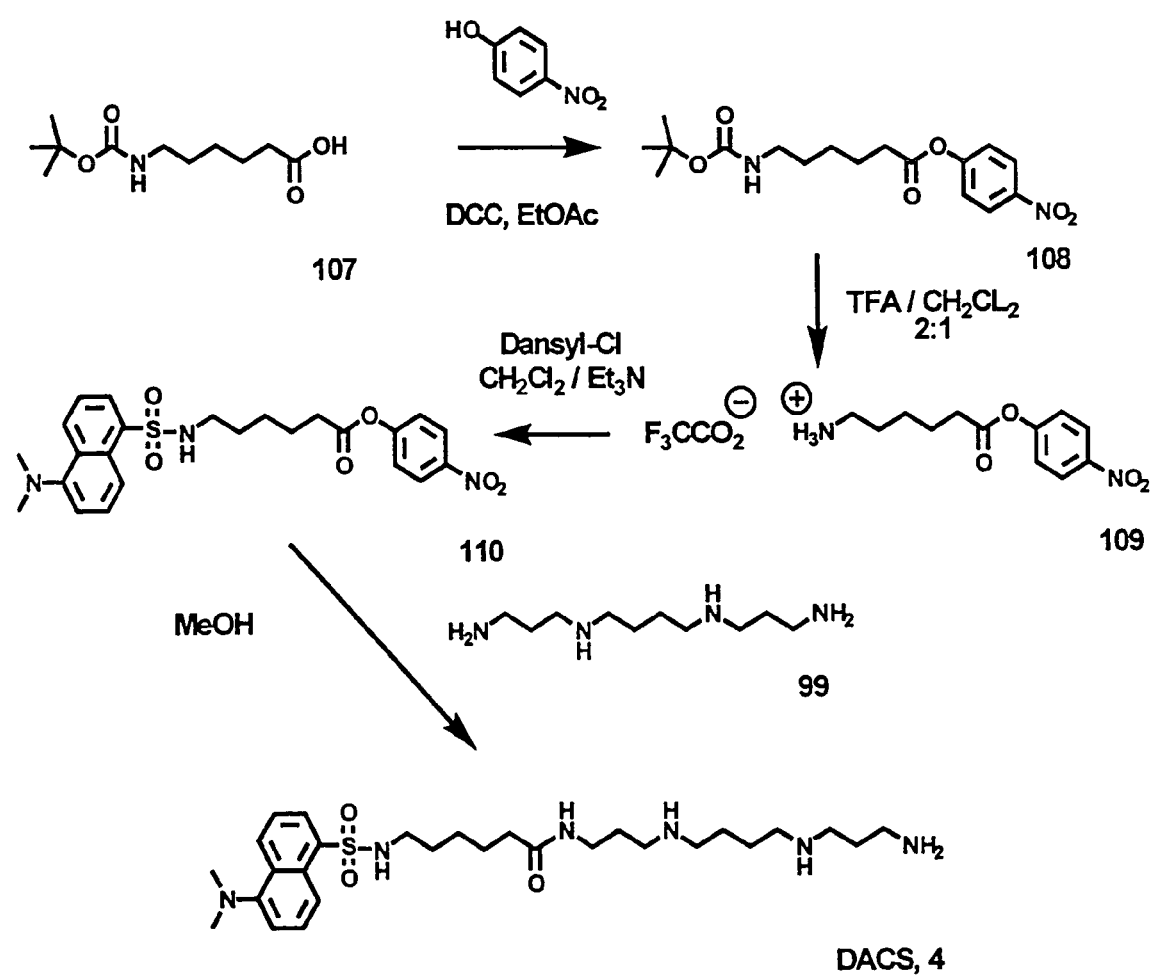

The preferred mono-protected polyamine intermediates were the N¹-tBoc derivatives produced according to Blagbrough et al., (*Tetrahedron Lett* 35:2057–2060, 1994), using di-tert-butyldicarbonate in tetrahydrofuran. Mono protected spermine was used to synthesize naphthyl-2,6-bis(N,N'-spermidylsulfonamide) as described in Example VIII B. Discovery of Lead Compound Following structural explorations around the amide, sulfonamide or urea substituent, it was determined that introduction of a six carbon, straight chain aliphatic linker between the polyamine core and the head group led to a 10-fold increase in binding to the PATr (see FIG. 1). Given the high affinity this compound, DACS 4, to its biological target, it was selected as a lead compound for further modification. Two methods for the synthesis of DACS 4 are presented. The first method uses two commercially available starting materials, appropriate for synthesizing small amounts of DACS 4. The synthesis DACS 4 from spermine and 6-((5-dimethylaminonaphthalene-1-sulfonyl)amino) hexanoic acid succinimidyl ester is shown in FIG. 8, (showing compounds 4, 99, 106) and described in more detail in Example IX The second, multistep method (FIG. 9; showing compounds 4, 99, 107–110), uses structurally flexible synthetic procedures for producing the modified analogues. The multistep production of DACS 4 in the second method (Examples X–XIII) illustrates the procedure used to synthesize many of the linker analogues in described herein. This method is based in part on R. Goodnow et al., (*Tetrahedron Lett.* 46:3267, 1990). The p-nitrophenyl ester of a N-tBoc blocked amino acid is synthesized using DCC in EtOAc and then deblocked by the trifluoroacetic/$CH_2Cl_2$ method. The p-nitrophenylalkylaminoester is then derivatized with an acyl chloride, sulfonyl chloride, or the equivalent, to introduce the head group. The N-substituted amino acid p-nitrophenyl ester reacts readily in methanol with excess polyamine to yield the desired product. The desired monosubstituted product is purified from the excess polyamine and a minor di-substituted side-product by low-pressure C18 reversed phase chromatography (RPLC) and $CH_3OH/0.5N$ HCl elution. Alternatively, the product can be separated on a weak cation exchanger such as BioRad 70, with a $NH_4OH$ gradient. A more detailed description is provided in Examples X–XIII. The two methods shown in FIGS. 8 and 9 compare the two purification methods used throughout this work (Examples IX, XIII)

Using the second procedure, different "head" groups can be easily coupled to the p-nitrophenyl activated ester (different "head groups outlined below). Following purification of this active ester, it can be readily coupled to the various polyamine derivatives. This method also gives great flexibility in the choice of linkers. Any compound possessing both an acid and an amino functionality can be incorporated into the molecule. See Examples IX–XIII.

Structural Modifications of DACS

The Polyamine Core

1. General Structural Issues

The structure below shows the general modifications that can be made to the polyamine core of the compound.

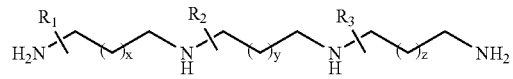

where x, y and z vary independently and may be 0 to 12, and $R_1$, $R_2$, and $R_3$ may be H, alkyl or aryl group. Stereoisomers can be separated A fruitful general approach to realize selectivity of binding to a target (e.g., protein) of interest has been to synthesize conformationally or stereochemically defined analogues of a binding molecule. By significantly reducing the number of possible rotomers or conformations a molecule can adopt, one can attain increased binding to the desired site. Since the molecule no longer has to search the entire "conformational space," its energy of interaction with the target increases many times.

Others have tried to solve the selectivity problem with polyamine analogues by synthesizing conformationally restricted analogues. Ganem replaced the butyl portion of spermine with 2-butene and 2-butyne diamino derivatives (Ganem, B., *J. Org. Chem.* 1987, 52, 5044–5046). Rajeev, K. G. et al., *J. Org. Chem.* 1997, 62, 5169–5173, incorporated a stereochemically defined, conformationally restrained pyrrolidine ring into the spermine backbone (FIG. 10; 115, x=1) Brand, G. et al., *Tetrahedron Lett.* 1994, 35, 8609–8612, synthesized cyclopolyamine analogues of spermidine and spermine. See, for example FIG. 10 (113, x=3, 4, and 5). The present inventors extended this work by producing the other analogues shown in FIG. 10. These analogues are synthesized using variations of known methods. The analogues where x=1 are produced by reacting spermine or N,N'-bis(3-aminopropyl)-1,3-propanediamine with formaldehyde as described by Ganem, B., *Acc. Chem. Res.*, 1982, 15, 290). The primary amines are protected as N-tBoc derivatives for the analogues 111 and 113. Acid deprotection then gives the desired products. The derivative 112, where x=1, was also synthesized Ganem.

Analogues 111 and 113 (FIG. 10), where x=2 to 4, were produced by reductive alkylation. $N^1$, $N^{14}$-Bis(tBoc)spermine was reacted with the dialdehyde, $OHC(CH_2)_{x-2}CHO$ and $NaBH_4$ in EtOH. Compounds 112 and 114 were made by the same procedure on a suitable $N^1,N^4$-bisprotected spermine derivative.

Stereochemically defined, internally cyclic structures (FIG. 10, 115) are synthesized using an intermediate aldehyde produced from alcohol 130 shown in FIG. 4. This protected alcohol 130 can be oxidized to the aldehyde using Swern conditions. Aldehyde extension by the Wittig reaction with formylmethylene triphenylphosphorane, followed by reduction (overreduced alcohol can be reoxidized to the aldehyde using pyridinium chlorochromate) and reductive amination/cyclization completed the sequence to make the analogues where x=2. By Wittig reaction with 3-bromopropyl triphenylphosphonium bromide, deprotection and intramolecular alkylative cyclization, the analogue where x=3 can be produced. Either stereoisomer can be produced by starting with L- or D-ornithine. Polyamines containing a guanidinium group are synthesized according to Iwanowicz, E. J. et al., *Synthetic Comm.* 23 1443–1445, 1993.

2. Natural Polyamines

The natural polyamines, including putrescine, spermidine and spermine, are incorporated into the compositions of this invention by coupling them to the various "head" and "linker" groups. Other naturally occurring polyamines that can be employed similarly include: $N^1$-acetylspermine, $N^1$-acetylspermidine, $N^8$-acetylspermidine, $N^1$-guanidinospermine, cadaverine, aminopropylcadaverine, homospermidine, caldine (norspermidine), 7-hydroxyspermidine, thermine (norspermine), thermospermine, canavalmine, aminopropylhomospermidine, N, N'-bis(3-aminopropyl)cadaverine, aminopentylnorspermidine, $N^4$-aminopropylnorspermidine, $N^4$-aminopropylspermidine, caldopentamine, homocaldopentamine, $N^4$-bis(aminopropyl)norspermidine, thermopentamine, $N^4$-bis(aminopropyl)spermidine, caldohexamine, homothermohexamine and homocaldohexamine.

3. $N^1$-Alkylated Polyamines

The metabolic stability in vivo of monosubstituted polyamine analogues is increased by modifying these compounds to resist enzymatic degradation. For example, substitution of the terminal primary amine group with an alkyl group would achieve this by preventing oxidative metabolism. This invention also includes compounds with alkylated secondary amino groups. N-alkylation of the amide nitrogens slows down proteolytic degradation.

The foregoing changes can be achieved by a number of synthetic routes. Substitution of carbon atoms a to secondary nitrogens and acylation of nitrogens can also slow degradation by polyamine oxidase. Such chemical modifications may minimize potential pharmacological side effects of these compounds.

Figure 11:
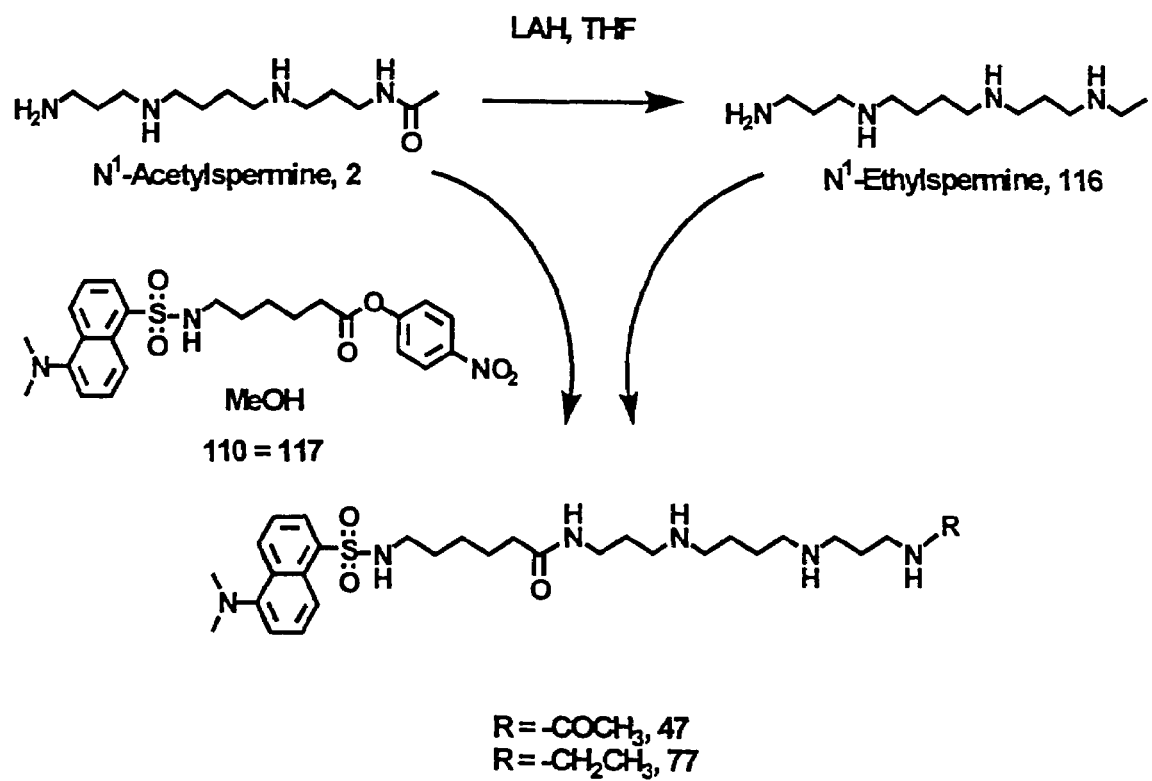
FIG. 11 is a synthetic scheme wherein free primary amino groups are blocked by N-acylation (44) and N-alkylation (77), thereby reducing potential metabolic degradation of the derivatized PAT inhibitors.

To reduce potential metabolic degradation of derivatized PAT transport inhibitors, the terminal free primary amino group can be blocked by N-alkylation (Bergeron, R. J. et al., *J. Med. Chem.* 37:3464–347, 1994) as illustrated in FIG. 11 (compounds 2, 47, 77, 116–117). Lithium aluminum hydride (LAH) reduction of $N^1$-acetylspermine 2 yields the desired $N^1$-ethylspermine 116. Reaction of $N^1$-ethylspermine 116 or $N^1$-acetylspermine 2 with a N-substituted p-nitrophenylester of an amino acid in methanol gives the desired compound modified with either an ethyl or an acetyl group at the primary $N^1$.

Figure 12:
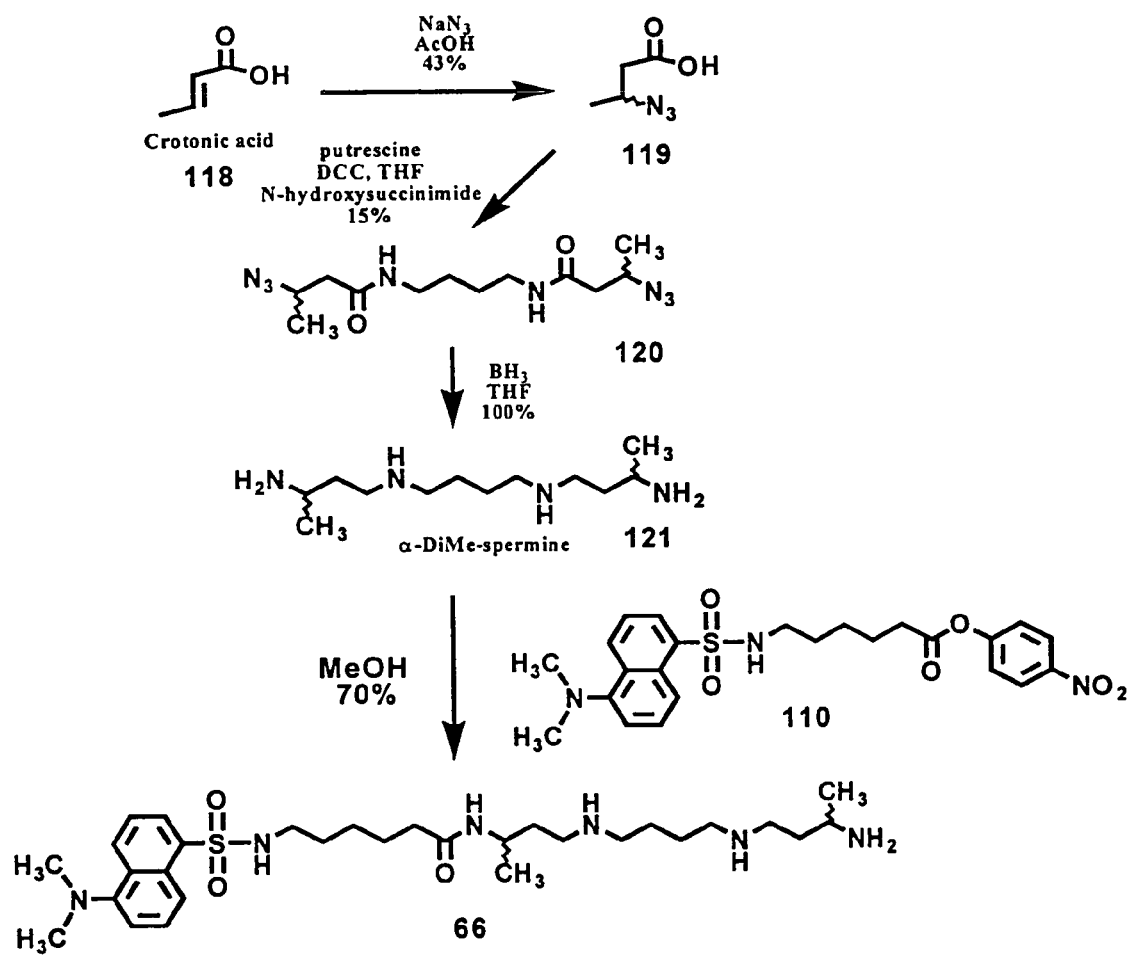
FIG. 12 is a synthetic scheme for bis α-gem-dimethylpolyamine analogues 121.
Figure 13:
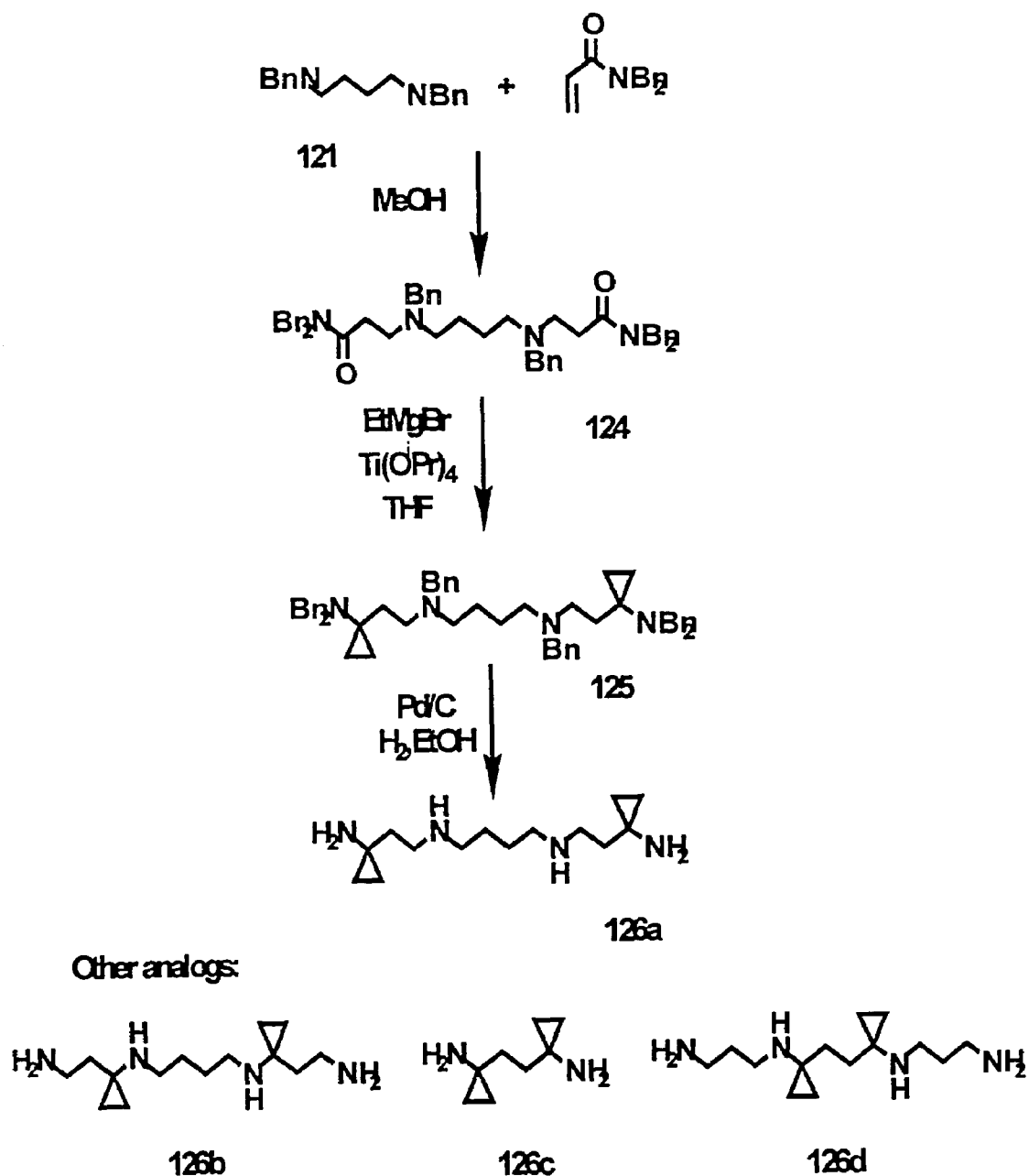
FIG. 13 is a synthetic scheme for internally substituted polyamine analogues containing cyclopropyl groups (122–126)

Alternatively, methyl groups can be introduced a to the terminal amino groups (121) of spermine (Lakanen, J. R. et al., *J. Med. Chem.* 35:724–734, 1992). The 1,12-dimethylspermine analogue 121 was very resistant to normal metabolic degradation. This compound is easily coupled to a linker and head group as shown in FIG. 12 (compounds 66, 18,121). Ganem, B., *J. Org. Chem.* 1986, 51, 4856–4861, synthesized bis α-gem-dimethylpolyamine analogues. The present inventors have extended upon these two reports and synthesized the bis-cyclopropylamine analogues by the route described below. See FIG. 13. Reaction of the perbenzylated diamide with EtMgBr and $Ti(O^iPr)_4$ according to Chaplinski, V., Angew. *Chem. Int. Ed. Engl.* 1996, 35, 413–414 or Lee, J. *J. Org. Chem.* 1997, 62, 1584–1585 produced the fully protected bis-cyclopropylamino analogue of spermine. Catalytic hydrogenation yields a fully deprotected polyamine. Other internally, cyclopropyl-substituted polyamine analogues can be produced in an analogous manner to that shown in FIG. 13. Other analogues produced are shown at the bottom of FIG. 13. These cyclopropyl polyamine analogues are activated by cellular enzymes to become alkylating agents.

Polyamine analogues of 4 with acetyl (47), N-ethyl (35) and α-dimethyl (66) substitution have been synthesized and shown to have $K_i$'s (for the MDA-MB-231 cell PATr) of 2100, 41, 18 nM, respectively.

Detectably labeled polyamine derivatives can be synthesized using radiolabeled $^{14}C$-spermine or other radiolabeled polyamine as starting material.

4. Internally Substituted Polyamine Analogues

Figure 14:
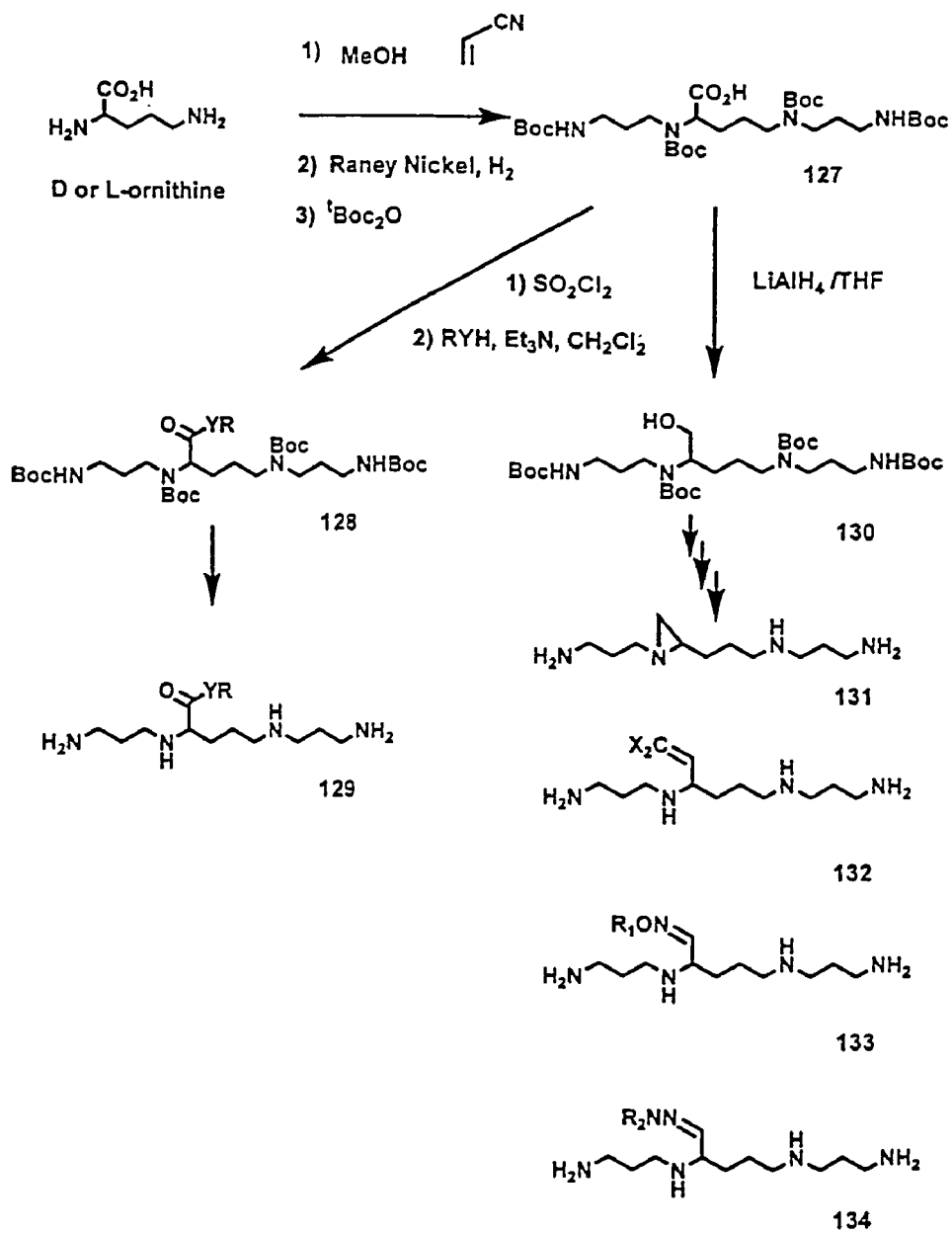
FIG. 14 is a synthetic scheme for internally substituted polyamine analogues containing a C—C branch (127–134)
Figure 17:
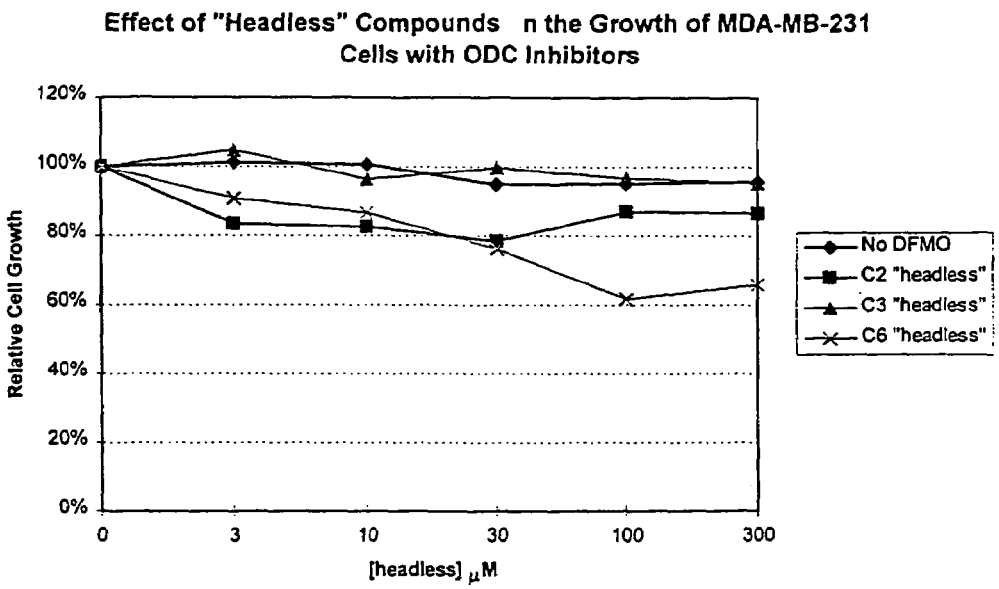
FIG. 17 is a graph showing the effects of DACS on growth of MDA breast cancer cells with and without DFMO.

Various polyamine analogues alkylated at internal carbons can also be synthesized. 5-carboxyspermine, tetra tBoc-5-carboxyspermine and its acid chloride are synthesized according Huber, H. et al., *J. Biol. Chem.* 271:27556–27563, 1994. The resulting acid chloride can then be reacted with various nucleophilic reagents to produce carboxy-substituted polyamine analogues following removal of the tBoc group. These analogues can then be coupled to the reagents that donate the linker and/or head group. Alternatively, the carboxy intermediate can be reduced to an intermediate that is used to synthesize numerous analogues. Such analogues are of interest in the present invention as alkylating agents (e.g., internal aziridine spermine derivatives) or as enzyme-activated irreversible inhibitors of enzymes involved in polyamine biosynthesis, utilization and degradation (e.g., spermine synthase, deoxyhypusine synthase, polyamine oxidase) as shown in FIG. 14 (compounds 130–134). Any enzyme that acts on the substituted carbon atom will generate a highly reactive intermediate that can alkylate the enzyme's active site residues.

5. Commercially Available Polyamine Analogues

Many polyamine derivatives are available commercially, and these can easily be derivatized further to make the polyamine analogues of the present invention.

Head Groups

1. General Description

The general construction of the lead compounds shown below indicates the connections between the head group, linker and polyamine:

where coupler$_1$ is —C(=O)NH—, —S(=O)$_2$NH—, —NHC(=O)—, —HNS(=O)$_2$—, —HNC(=O)NH—, —HNC(=S)NH—, O—C(=O)NH—, —O—, —S—, —CH$_2$— or —NH—; and coupler$_2$ is —C(=O)NH—, —S(=O)$_2$NH—, —HNC(=O)NH—, —HNC(=S)NH— or —NH—

A number of coupling chemistries can be used to combine the "head" group and the linker moiety. Types of "head" groups are disclosed below as are additional groups that can be substituted onto these head groups.

The coupling between the polyamine and linker will be described below before description of the linkers. What follows is the definition of the head groups.

The structural diversity of preferred head groups is very large, and most organic groups that can be covalently attached to an amine are potential candidates. The following table provides guidance regarding the intended head groups but is by no means is intended to be limiting. Mono and multi-substitutions on the ring structures of these head groups are also intended.

| LIST OF HEAD GROUP SUBSTITUENTS | | | |
| --- | --- | --- | --- |
| halogen | cyclohexyl | ethoxyl | propyl ester |
| methyl | cycloheptyl | propoxyl | isopropyl ester |
| ethyl | cyclooctyl | thio | cyano |
| propyl | cyclononyl | methylthio | isocyanato |
| isopropyl | cyclodecyl | ethylthio | trifluoromethyl |
| butyl | hexyl | propylthio | trichloromethyl |
| isobutyl | 2-hexyl | butylthio | tribromomethyl |
| tert-butyl | 3-hexyl | isopropylthio | azido |
| pentyl | allyl | nitro | Acetoxy |
| 2-pentyl | vinyl | amino | Carboxamide |
| 3 -pentyl | acetylenic | acetamide | N-methylcarboxamide |
| neopentyl | propargylic | formamide | N,N-dimethylcarbox- |
| cyclopentyl | homopropargylic | carboxylic | amide |
| cyclopropyl | hydroxyl | methyl ester | N-ethylcarboxamide |
| cyclobutyl | methoxyl | ethyl ester | N,N-diethylcarboxamide |

2. Aromatic Groups

Aromatic groups include phenyl naphthyl, 1-, 2-, or 3-biphenyl, indenyl, acenaphthylenyl, anthracenyl, phenanthrenyl, phenalenyl, triphenylenyl pyrenyl, diphenylmethylenyl, etc.

3. Heterocyclic Groups

Heterocyclic groups include pyrrolidinyl, piperidinyl, piperazinyl, morpholinyl, biphenyl, furanyl, pyrrolyl, 1,2-diazolyl, imidazolyl, 1H,1,2,3-triazolyl, 1H-1,2,3,4-tetrazolyl, thiazolyl, oxazolyl, 1,3,4-thiadiazolyl, pyridinyl, pyrimidyl, 1,2-diazinyl, 1,4-diazinyl, 1,3,5-trizinyl, dibenzofuranyl, acridinyl, 2,1,3-benzothiadiazole, isoquinolinyl, quinolinyl, benzufuranyl, isobenzofuranyl, 1,3-benzodiazinyl, phenazinyl, phenoxazinyl, phenothiazinyl, pyran, chromenyl, xanthenyl, indolizinyl, isoindolyl, indolyl, purinyl, phthalazinyl, naphthyridinyl, quinoxalinyl, quinazolinyl, cinnolinyl, ptericinyl, carbazolyl, β-carbolinyl, phenanthridinyl, acridinyl, perimidinyl, phenanthrolinyl, isothiazoly, furazanyl, indolinyl, isoindolinyl, quinuclidinyl, and biotinyl.

4. Aliphatic Groups

This class includes straight-chain, branched and cyclic hydrocarbons attached to the linker. The group includes C$_{2\text{-}10}$ alkanes; C$_{3\text{-}10}$ alkenes containing 1 to 3 unsaturations; C$_{3\text{-}10}$ alkynes containing 1 to 3 unsaturations; branched C$_{3\text{-}10}$ alkanes, alkenes and alkynes; polycyclic aliphatic hydrocarbons and steroid-like ring systems that include C$_{3\text{-}8}$ cycloalkyl, adamantyl, camphoryl, cholesteryl, etc.

5. Miscellaneous—

DNA Intercalators:

Coupling an intercalator to the polyamine will yield an agent with much higher affinity for nucleic acid targets. Examples of intercalating agents amenable to this use are acridine, 9-aminoacridine, proflavine, actinomycin D, daunorubicin, doxorubicin, nogalamycin, menogaril, ellipticine, BD-40, amsacrine, acodazole, 2-pheylquinoline carboxamide, crisnatol, nitracrine, pyrazoloacridine, mitonoafide, ametantrone, mitoxantrone, oxanthrazole, bisantrene, echinomycin. For a review of DNA intercalating agents see Baguley, B. C., *Anti-Cancer Drug Design* 1991, 6, 1–35.

b. Biochemical Conjugates

Drug selectivity is achieved by targeting specific cells or enzymes/receptors on cells. The following biochemicals are candidates for coupling to polyamines for producing a selective pharmaceutical agent: steroids, prostaglandins, phospholipids; enzyme cofactors including nucleotide containing molecules such as NADH, AcetylCoA, AdoMet, flavin, tryptophantryptophyl quinone (TTQ), etc.

An additional series of head groups comprises polyanines conjugated to polyethylene glycol (PEG) or O-methylated PEG (abbreviated MeOPEG) polymers of various sizes.

6. Multiple Ring Head Groups

Head groups can vary from simple alkyl substitutions to multi-ring and multi-single-ring substitutions. Some of the structural variations are schematically represented in FIG. 15.

Spacers X, Y and Z (for example FIG. 15, compounds 135–139) are defined as bonds or straight chain groups that attach different ring structures in a multiple ring head group. In some cases the spacers function as direct C—C or C—N attachments. Conventional spacers known in the art are similar to the linkers described herein. Known chemistries are used for covalent attachment of a ring structure in a head group with a spacer, for example, the formation of amide, sulfonamide, ether, thioether, ester, —C—C— and —C—N— and —N—N— bonds. R$_1$, R$_2$ and R$_3$ are typically alicyclic, aromatic, or heterocyclic rings when substituted in multi-ring head groups. These ring structures individually can also be substituted. Some of the multi-ring head group types described above are available from commercial sources, and examples are shown as structures 140 to 147 in FIG. 16. Alternatively, these or similar compounds are readily synthesized.

Linker Group

1. General Description

The linker portion of the compound can be represented by a general structure with an amino group at one end and an acid group on the other. One group of linkers contains diamino groups that are bonded via a urea linkage to the polyamine and via an amide, urea or sulfonamide linkage to the head group. The head group can also be bonded through other couplings such as ether, thioether and C—C bonds. The schematic structure shown above (in the section labeled "Head Groups, 1. General Description) shows the function of the linker moiety connecting the head group to the polyamine and possessing a desired length and combination of steric, conformational and hydrophobic properties. Also shown are the possible combination of coupling methods. Each coupling method can be used in combination with any of the three methods in FIG. 3 at the other position to result in a wide array of desired properties.

The linker group can have a range of properties that are reflected by the number of variations discussed below. Changes in the linker structure will be affect the properties of the whole polyamine analogue such as hydrophobicity, hydrophilicity, distance between head and polyamine portions, steric arrangement of head and polyamine portions, conformational properties, solubility and electronic properties.

2. Aliphatic Straight Chain Linkers

A series of linkers was been synthesized to test the effect of different distances between head group and polyamine. This series is most simply represented by the straight-chain aliphatic linkers having various carbon chain lengths shown below as compound 148).

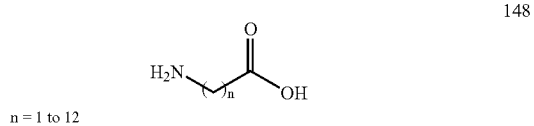

Figure 18:
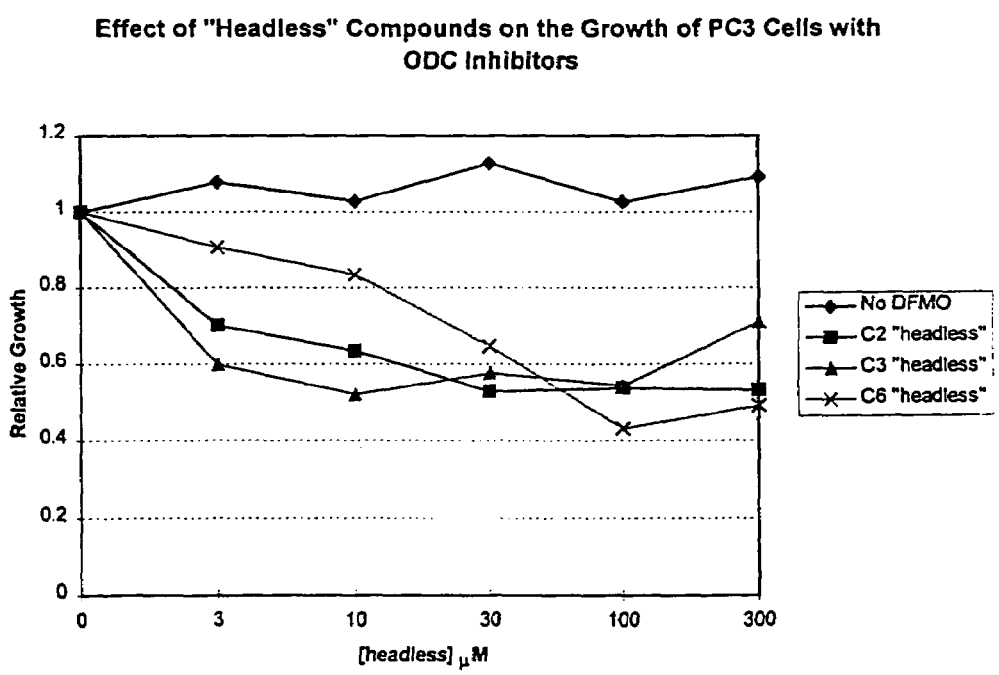
FIG. 18 is a graph showing the effects of headless polyamine analogues on growth of PC-3 prostate cancer cells with and without DFMO.

The present inventors discovered that linker length had dramatic effects on the PAT inhibitory activity and the cell growth inhibitory activity. A low $K_i$ is optimal for $C_6$ linkers in the presence of an aromatic head group. However, in the absence of a head group, differences in growth or transport inhibitory activities have not been dramatic. Thus, "headless" compounds have $K_i$'s in the order of about 25 nM but have more attenuated inhibitory effects cell growth (breast cancer cell line) most likely due to their ability to actually be transported. The prostate cancer cell line is more powerfully inhibited by these "headless" inhibitors as shown in FIG. 18 and Example XI. The C3-headless compound had dramatic effects on cell growth.

The synthetic route to this series of compounds, starting with various polyamines and head groups, is represented by the DACS 4 synthetic scheme depicted in FIG. 9 and discussed in more detail in Example IX to XIII). The amino group is protected by the N-tBoc group, and the carboxylic acid is then activated by forming the p-nitrophenyl ester. After acid deprotection of the N-tBoc group, the amino group can be reacted with an acid or sulfonamide chloride of the desired head group. After purification, direct reaction with the polyamine of choice in methanol gives the desired product. This can be purified by either (I) reverse-phase silica gel chromatography using 2:9 MeOH/0.5 N HCl or (2) cation-exchange chromatography over BioRex 70 resin ($NH_4$ form) using a linear gradient of from 0 to 2N $NH_4OH$.

3. Unsaturated Straight-Chain Aliphatic Linkers

Varying degrees of unsaturation (alkene and alkyne) together with the geometric isomers of the alkene derivatives can be introduced into the linker moiety as depicted below (149 and 150). These variations allow introduction of conformational restraint into the final product.

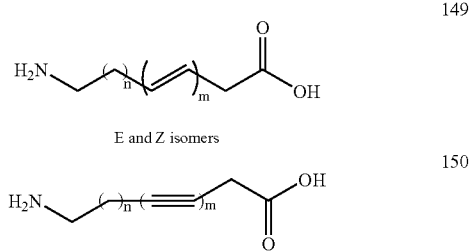

where n=0 to 7 and m=1 to 4

4. Carbon-Substituted and Cyclic Aliphatic Linkers

Branched chain and cyclic saturated aliphatic linker groups impose conformational restraint on the desired polyamine analogue. Compounds 151 and 152 below illustrates this class of structure.

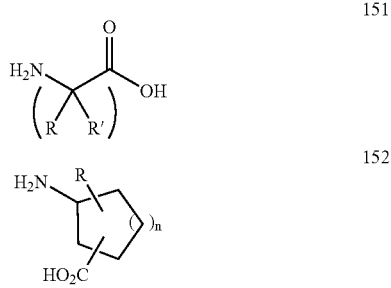

where n=1–10; R and R' vary independently and can be H or $CH_3(CH_2)_m$, and where m=1 to 10.

5. Chiral Carbon-Substituted Amino Acid Linkers

Figure 19:
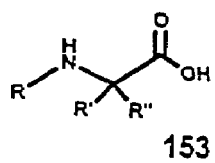
FIG. 19 lists chiral carbon-substituted amino acid linker groups.

Great structural diversity can be incorporated quickly into the polyamine analogues by using any of the large number of chiral amino acids that are available commercially. Many of the chiral amino acid intermediates to be used in the synthetic scheme shown in FIG. 9 are also available commercially, including some N-tBoc protected amino acids and some N-tBoc protected amino acid p-nitrophenyl esters. FIG. 19 (153) illustrates a variety of derivatives that have been produced by this method.

An additional thousand α-amino acid analogues known in the art can be used to form polyamine adducts. These are very easily incorporated into the present invention through the synthetic sequences described in FIGS. 8 and 9. Several key examples are; t-butylglycine, ornithine, α-aminoisobutyric acid, 2-aminobutyric acid, α-aminosuberic acid, 4-chlorophenylalanine, citrulline, β-cyclohexylalanine, 3,4-dehydroproline, 3,5-diiodotyrosine, homocitrulline, homoserine, hydroxyproline, β-hydroxyaline, 4-nitrophenylalanine, norleucine, norvaline, phenylglycine, pyroglutamine, β-(2-thienyl)alanine, etc. Several important β-amino acids are easily incorporated into the present invention through the chemistry discussed above. A key example is β-alanine, etc.

Both stereoisomers of the natural L-amino acids (L=S) or D-amino acids (D=R) can be used in this invention. Because each isomer can be used individually, the structural diversity of the analogues is markedly enhanced.

6. "Headless" Linkers

The desired biological properties do not always depend upon the presence of a head group. Hence, a large series of so-called "headless" derivatives, containing a polyamine and linker without a head group were synthesized and tested. These derivatives are made by reacting the active ester (p-nitrophenyl or N-hydroxylsuccinimide) of the N-tBoc amino acid with the polyamine of interest. The resulting N-tBoc protected derivatives are then purified by cation-exchange chromatography over BioRex 70 ($NH_4$ form) resin using a linear gradient from 0 to 2N $NH_4OH$. The tBoc group can then be cleaved by acid treatment. Both the tBoc and acid deprotected derivatives can be tested for biological activity. The full series of amino acids discussed above, together with other derivatives have been synthesized. A more detailed discussion of the synthesis of $N^1$-[6-aminocaproylspermine] appears in Example XIV.

Reactive, Irreversible Polyamine Transport Inhibitors

A. Alkylating Reagents—

Aziridines

Polyamines substituted with fluorophores and other bulky end group were found to have the intrinsic property of high avidity binding to the PATr. This suggested that, in addition to utility as a diagnostic or research tool, they are useful as therapeutic agents for treating diseases or conditions wherein it is desirable to inhibit PAT. Their intrinsic affinity for other polyamine targets such as DNA broadens even further the scope of their therapeutic utility.

In a preferred embodiment the polyamine core is substituted with the aziridinyl group. The embodiment shown in FIG. 20 has a second substituent (a fluorophore such as dansyl or another bulky group). Aziridinyl-substituted polyamines react with nucleophilic groups in target binding complexes (receptors, transporters, enzymes and nucleic acids). In addition they can be exploited to bind other reactive moieties to polyamines. These mono- and di-substituted polyamine analogues are useful as drugs because of their inhibition of (a) the PATr, (b) polyamine synthesis and (c) reactions that use nucleic acids as substrates.

In one embodiment, a reactive group other than aziridine is introduced into a polyamine already substituted with a head group and a linker. This reactive group allows the labeled polyamine to bind covalently to an appropriate nucleophilic site on a polyamine-binding target molecule such as the PATr. Compounds of this type are used to covalently label receptors, enzymes or nucleic acids; thus, the modified polyamine serves as an affinity label that is useful in diagnostic assays and as a tool to isolate a polyamine binding target. Again, such compounds used as drugs will treat diseases or conditions which are ameliorated by blocking PAT or DNA-polyamine interactions. By virtue of the relative irreversibility of their binding, such compounds can be used at lower doses or at decreased frequency compared to compounds known in the art.

Disubstituted polyamines are synthesized by using the appropriate amine protecting groups on the polyamines. Reagents for the stepwise fuctionalization of spermine are known (Bergeron, R. J. et al., *J. Org. Chem.* 53: 3108–3111 (1988); Byk, G. et al., *Tetrahedron Lett.* 38: 3219–3222 (1997)). Bergeron et al. (supra) described the use of four independent amine-protecting groups: benzyl, t-butoxycarbonyl, trifluoroacetyl, and 2,2,2-trichloro-t-butoxycarbonyl. Conditions that allow the selective removal of each protecting group were also described. These reaction conditions allow independent and selective derivatization of each nitrogen of spermine. Thus this invention includes derivatization of monofunctionalized spermine with a linker/head group on any one of the four nitrogens and the synthesis of polyamine analogues with more than one functionalized nitrogen.

Methods to introduce an aziridine group into spermine (Li et al, *J. Med. Chem.*, 39:339–341 (1996) and into derivatives of spermidine (Yuan et al, *Proc. Am. Assoc. Cancer Res.*, 34: 380 (1993) are available. A synthetic scheme for $N^1$-(aziridinyl)-$N^{12}$-[($N^6$-dansyl)-6-aminocaproyl]spermine is shown in FIG. 20 154–157).

Figure 20:
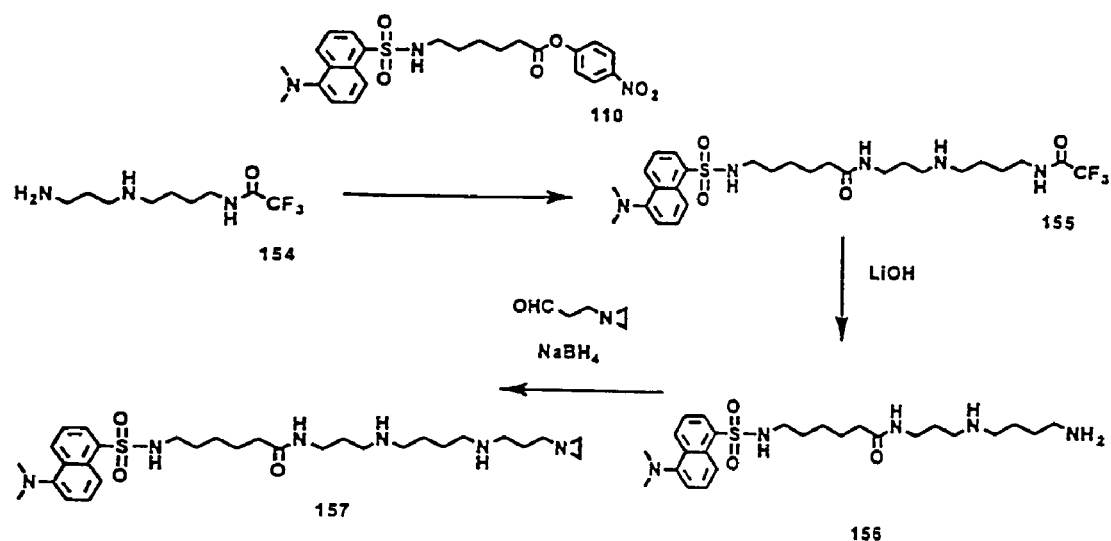
FIG. 20 is a scheme of the synthesis of N'-(aziridinyl)-$N^{12}$-[($N^6$-dansyl)-6-aminocaproyl]spermine 157.
Figure 21:
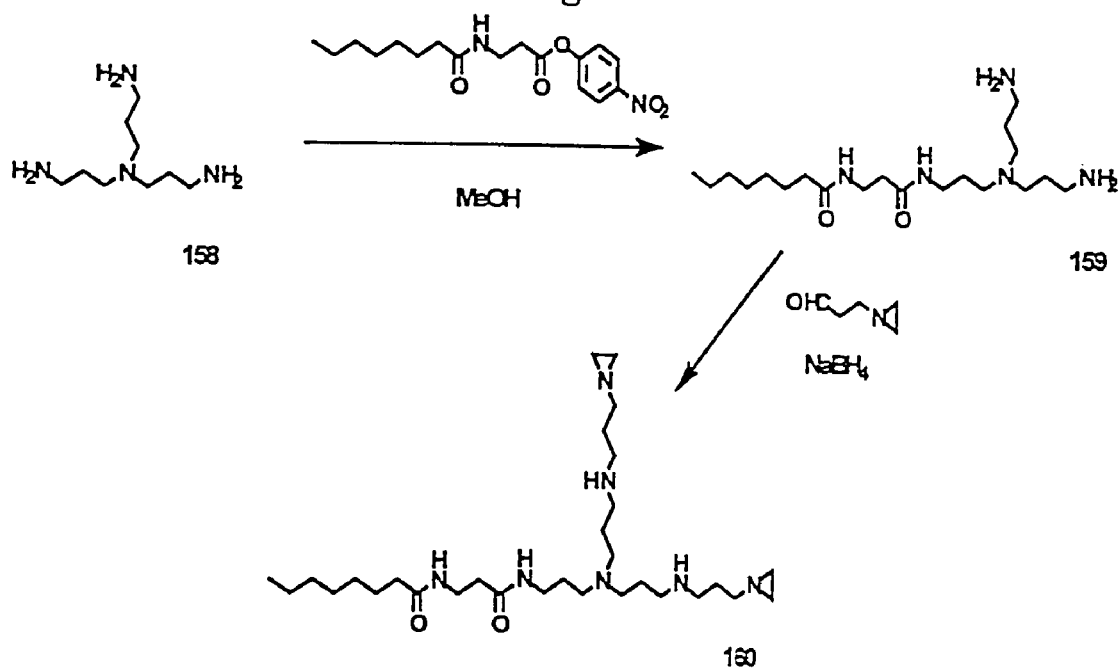
FIG. 21 is a scheme of the synthesis of a di-substituted aziridinyl polyamine analogue 160.

Whereas FIG. 20 shows the synthesis of the spermine derivative, any other polyamine derivative can be produced using an appropriately protected polyamine precursor, coupling to the linker/head group moiety and reductive amination with 3-aziridinepropanal. Removal of the protecting group(s) then gives the desired, reactive polyamine derivative. An additional example of this approach, illustrating the chemical flexibility it permits, is shown in the FIG. 21 (158–160).

3. Other Reactive Groups

Other useful moieties that can be added instead of the aziridine group and that react with nucleophiles to form covalent bonds include chloro-, bromo- and iodoacetamides, sulfonylfluorides, esters, nitrogen mustards, etc.

The chemically reactive 2-haloacetamide group can easily be introduced into any of the polyamine analogues by reaction with the appropriate 2-haloacetic acid halide. Other chemically reactive groups are described below.

B. Photochemically Activated Reagents

The use of photochemically activated functionalities on biologically active molecules is a well known (Fleming, S. A., *Tetrahedron* 51:12479–12520, 1995). In the polyamine field, Felschow et al. attached an azidobenzoic acid moiety to spermine and examined the interaction of the resulting adduct with cell surface proteins (Felschow, D M et al. *Biochem. J.* 328, 889–895, 1997; Felschow, D M et al., *J. Biol. Chem.* 270:28705–28711, 1995). Since their photoprobe had an apparent $K_i$ of 1 μM versus spermidine for the PATr, the photolabelled proteins described were a mixture of polyamine binding proteins. One of the most potent PAT inhibitors of the present invention, DACS, has a Ki of <10 nM, which indicates an affinity 100 times higher than the compound reported by Felschow et al. Therefore introduction of a photoactivatable group to this molecule holds great promise in the isolation of the PATr protein(s).

1. Azide

Substitution of the dimethylamino group in dansyl chloride by azide produces a photochemically reactive chemical group. The preparation of 1-azido-5-naphthalene sulfonyl chloride has been described (Muramoto, K., *Agric. Biol. Chem.*, 1984, 48 (11), 2695–2699), and it is also available commercially from Molecular Probes Inc. (Eugene, Oreg.). Introduction of this compound into the synthetic scheme for DACS is straightforward and merely requires substitution for dansyl chloride.

This azido derivative, would enable isolation and characterization of the PATr protein(s), and would also find use as an irreversible, photoactivatable drug molecule.

2. Diaziridines

Substitution of a diaziridine group on the head group would accomplish many of the same goals as noted above.

3. Diazo Groups

Polyamine analogues with photoactivatible head groups are made using p-nitrophenyl 3-diazopyruvate, a reagent for introduction of a photoactivatable 3-diazopyruvate group to an aliphatic amine. This agent is also available from Molecular Probes, Inc. The desired derivative is made by reacting this reagent with the free amino, p-nitrophenyl activated linker precursor, purifying the linker/head group intermediate, and reacting it with the polyamine.

Reporter Molecules (Probes) for PAT and other Polyamine-Binding Proteins

Various moieties can be attached to polyamines to produce novel inhibitors of PAT with utility as probes in a PAT assay and for drug screening. Such chemical modifications do not destroy effective binding and, in fact, enhance the affinity of the derivatized polyamine for the PATr. Such compounds are thus useful for measuring polyamine uptake and, more importantly, in high throughput screening assays to discover therapeutically useful inhibitors of this uptake.

In a preferred embodiment the polyamine analogue is immobilized to a solid support which enables removal of the analogue and any interacting/binding molecules from a complex mixture.

Because a number of polyamine binding protein are targets for therapeutic intervention, an improved assay for polyamine binding or uptake is desirable. Small changes in polyamine structure can have drastic effects on activity. Reporter molecules are polyamine analogues that are conveniently detectable while maintaining their binding activity to the PATr. For optimal binding to the PATr, the reporters are sufficiently specific so that binding other polyamine binding molecules does not interfere in the assay. $N^1$-substituted polyamines are competitive inhibitors for the PATr and for several other polyamine binding proteins such as the external sensing $Ca^{+2}$ receptor and the NMDA receptor. There is no report in the art of a molecule that binds to the transporter (or any other polyamine binding membrane receptors) with the high affinity of the present probes. The inventors have therefore focused on producing suitable reporterbound polyamines that maintain a reasonable range of detectability and that bind competitively with spermine. FIG. 1 illustrates a synthetic scheme for various $N^1$-linked polyamine analogues.

Reporter Head Groups

The Head/Reporter group structural diversity is very large and includes most organic groups that can be covalently bonded to an amine. The groups described below are but several examples of the head groups of the present invention and are not intended to be limiting.

A. Fluorescent/Chemiluminescent Head Groups

The dansyl fluorescent group can be substituted by any of a large number of fluorophores, for example, as disclosed in Haugland, *Handbook of Fluorescent Probes and Research Chemicals*, Sixth Edition, Molecular Probes, Eugene, Oreg., 1996. A number of dansyl-polyamine-like molecules are known and commercially available, including: didansylcadaverine, monodansylcadaverine, didansylputrescine, MDS and tridansylspemidine (Sigma Chemical Company, St. Louis, Mo.). The syntheses of monodansylputrescine (Raines, D. E. et al., *J Membrane Biol.* 82:241–247, 1984) and monodansylcadaverine (Nilsson, J. L. G. et al., *Acta Pharm. Suedica* 8:497–504, 1971) have been described.

In general, a fluorescent reagent is selected based on its ability to react readily with an amino function of a polyamine such as spermine. Examples of such fluorescent probes include the Bodipy™ (4,4-difluoro-4-bora-3a,4a-diaz-s-indacene) fluorophores which span the visible spectrum (U.S. Pat. No. 4,774,339; U.S. Pat. No. 5,187,288; U.S. Pat. No. 5,248,782; U.S. Pat. No. 5,274,113; U.S. Pat. No. 5,433,896; U.S. Pat. No. 5,451,663). The preferred member of this group is 4,4-difluoro-5,7dimethyl-4-bora-3a,4a-diaza-s-indacene-3-propionic acid. Preferred fluorophores for derivatizing polyamines according to this invention are those which are excited by ultraviolet light. Suitable fluorescent materials include Cascade Blue™, coumarin derivatives, naphthalenes (of which dansyl chloride as exemplified herein is a member), pyrenes and pyridyloxazole derivatives, Texas red™, Bodipy™, erythrosin, eosin, 7-nitrobenz-2-oxa-1,3-diazole (NBD), pyrenes, anthracenes, acridines, fluorescent phycobiliproteins and their conjugates and fluoresceinated microbeads. Use of certain fluors such as the phycobiliproteins and fluoresceinated microbeads will permit amplification of the fluorescent signal where cells have few PATr sites.

Fluorescein, fluorescein derivatives and fluorescein-like molecules such as Oregon Green™ and its derivatives, Rhodamine Green™ and Rhodol Green™, are coupled to amine groups using the isocyanate, succinimidyl ester or dichlorotriazinyl-reactive groups. The long wavelength rhodamines, which are basically Rhodamine Green derivatives with substituents on the nitrogens, are among the most photostable fluorescent labeling reagents known. Their spectra are not affected by changes in pH between 4 and 10, an important advantage over the fluoresceins for many biological applications. This group includes the tetramethylrhodamines, X-rhodamines and Texas Red derivatives.

In yet another approach, an amino group or groups in the polyamine are reacted with reagents that yield fluorescent products, for example, fluorescamine, dialdehydes such as o-phthaldialdehyde, naphthalene-2,3-dicarboxylate and anthracene-2,3-dicarboxylate. 7-nitroben-2-oxa-1,3-diazole (NBD) derivatives, both chloride and fluoride, are useful to modify amines to yield fluorescent products.

Those skilled in the art will recognize that known fluorescent reagents modify groups other than amines. See for example, Haugland, R. P., supra; Chapter 2, where modification of thiols is described at pages 47–62. Modification of alcohols, aldehydes, ketones, carboxylic acids and amides is described in Haugland, supra (at pages 63–81). Hence, fluorescent substrates for the PATr can readily be designed and synthesized using these other reactive groups. The most preferred reporter moiety is a fluorophore, either one which phosphoresces spontaneously or one which fluoresces in response to irradiation with light of a particular wavelength.

Chemiluminescent reporters are also acceptable. Examples of particularly useful chemiluminescent labeling compounds are luminol, isoluminol, theromatic acridinium ester, imidazole, acridinium salt and oxalate ester.

B. Radioactive Head Groups

In order to use a probe for detection, various radioactive groups can be added for localization of the probe. Radioactive groups can be any of the various sulfonyl chlorides, acyl halides, or other activated groups or non-activated groups that contain a radioactive element which can be incorporated into polyamine analogues. The polyamine itself can contain a radioactive element which may aid in detection.

Radioactive reporter moieties are detected by measurement of the emitted radiation. Examples of suitable radioactive reporter moieties are those labeled with gamma-emitters such as $^{125}I$, $^{123}I$ and $^{99m}Tc$. Some $\alpha$ and $\beta$ emitters may suffice for detection.

C. Immobilizable Head Groups

With the large supply of various antibodies that are commercially available and the variety of conjugating systems like avidin-biotin, it is possible to place various immobilizable head groups into the polyamine analogue. These include small molecules for which specific antibodies are commercially available, such as anti-dansyl, anti-fluorescein, anti-BODIPY, anti-Lucifer Yellow, anti-Cascade Blue and anti-DNP. Proteins or peptides can also be derivatized to polyamines for detection with available antibodies.

D. Solid Support

In various embodiments of the enzymatic assays, the immobilization may be to any "solid support" capable of binding a capture protein (e.g., streptavidin or antibodies). Well-known supports, or carriers, include glass, polystyrene, polypropylene, polyethylene, polyvinylidene difluoride, dextran, nylon, natural and modified celluloses, polyacrylamides, agaroses, and magnetite. The nature of the carrier can be either soluble to some extent or insoluble for the purposes of the present invention. The support material may have any structural configuration so long as the immobilized molecule is capable of binding to its ligand. Thus, the support configuration may be spherical, as in a bead, or cylindrical, as in the inside surface of a test tube or microwell, the external surface of a rod, or a chip. Alternatively, the surface may be flat such as a sheet, test strip, microwell bottom, etc. Also useful for certain embodiments are magnetizable groups such as gadolinium complexes or electron-opaque groups. Those skilled in the art will know many other suitable carriers for binding antibody or antigen, or will be able to ascertain such by use of routine experimentation.

Assay of Polyamine Transport

The preferred embodiment of the PAT assay for identifying PAT inhibitors is a high throughput assay using a fluorescent polyamine-like probe. Transport of the probe through the cell membrane via a PATr is tested in the presence of candidate transport inhibitors. This and all subsequent steps are preferably performed by a robotic system for increased efficiency.

Cells are plated in 96 well sterile microplates at an appropriate density for adherence and mid-log growth within 15–96 hours (the "test plate"). For an initial rate measurement, a pre-plate (96 well plate format) is prepared using, for example, a combinatorial library of potentially inhibitory compounds (such as those prepared by PanLabs Inc., Bothell, Wash.). See also description of plyamine combinatorial libraries, below.

In addition to 1 nmole of the test inhibitor in each well, 1 μmole of aminoguanidine and 1–100 nmoles of the fluorescent polyamine probe are added. The final volume can be from about 25 μl to about 200 μl. Aminoguanidine is included to prevent the oxidative breakdown of the polyamine compounds in the culture medium.

The assay is initiated by transferring the contents of the pre-plate to the test plate in a timed fashion. The cells are incubated with the test inhibitor and the fluorescent polyamine probe for 1–60 minutes. The incubation is terminated by removing the medium and washing the wells three times with ice cold medium containing 1 mM aminoguanidine and 1 μM spermidine. The cells are then lysed with detergent (e.g., 100 μl of 0.1% sodium dodecylsulfate) and transferred to a fluorescence plate reading system, preferably a top reading fluorescence spectrophotometer.

A well is scored as positive if the test inhibitor causes the fluorescence to drop below 50% of the negative (no inhibitor) control. The inhibitor compounds which score positive are then tested to determine their binding constants by repeating the above assay while varying the concentrations of both the fluorescent probe and the test inhibitor. A standard kinetic analysis is performed to quantify the type of inhibition (e.g., competitive vs. noncompetitive) and its effectiveness.

Using a conventional radiometric assay (described below), the present inventors were able to screen about 20 compounds per week for the ability to inhibit PAT in a cell line. With the high throughput fluorescent assay disclosed herein, one can screen 250 compounds or more per week. Although the radiometric assay might lead to identification of the same compounds, the time scale would be much longer.

As described, the preferred detection method is based on the fluorescence of the modified polyamine probe of the present invention. However, there are a number of other useful detection methods which include chemiluminescence, colorimetry as well as conventional radiometry. For chemiluminescence detection, a chemiluminescent group is substituted for the fluorescent group. For example, fluorescent fluorescamine adducts can be converted to chemiluminescent products with bis-trichlorophenyl oxalate (Walters, D L et al., *Biomed Chromatogr:* 8:207–211, 1994). In yet another embodiment, colorimetric detection is used with chromophores having high extinction coefficients.

High throughput screening (HTS) has become an essential part of the rapid drug discovery process. Using an HTS assay, many compounds can be assayed using candidate compounds from existing libraries or libraries synthesized by combinatorial approaches such as that described herein. Compounds numbering in the thousands to hundred thousands are now routinely screened in the pharmaceutical industry, using microtiter plate formats with either 96 or 384 wells and robotic devices which transfer reagents, wash, shake and then measure activity signals which are directly imported in computer compatible form. The robotic devices and optimization programs to aid rapid drug development are well-known art. The three requirements of HTS are speed, accuracy and economy.

A. Radiometric Assays

In a conventional radiometric assay, the cells are incubated under growth conditions with [5,8-$^{14}$C]spermine in serum-free medium for varying intervals. Cells are plated at a known density in 24 well plates in standard tissue culture medium and allowed to adhere and grow for 15–96 hours. Due to the low signal of the radiolabel in this assay, 96 or 386 well microplates cannot be used in this assay, creating a major bottleneck for throughput. Cell numbers are determined, and the plate is placed in a temperature controlled system at 37° C. Aminoguanidine is added to the medium to a final concentration of 1 mM. The inhibitor to be tested and the radioligand (preferably $^3$H-spermidine, $^{14}$C-spermidine or $^{14}$C-spermine) are prepared in separate plates. The assay is initiated by the mixing of the inhibitor and radioligand. The cells are incubated for an interval of about 1–60 minutes depending on cell type. The assay is terminated by removing the medium and cooling the plates to 4° C. The cells are then washed with cold medium three times, dissolved in 0.1% sodium dodecylsulfate, and the radioactivity in solution is determined by scintillation counting.

B. Development of Polyamine Analogues for Use with PAT Assay

As indicated above, reporter moiety can be bound to a terminal amine or to an internal site of a polyamine. Most preferred are single substituted fluorescent groups bonded to any of the nitrogens. Substitution of fluorescent groups on the different carbons of a polyamine is exemplified by N-(4-dansylaminobutyl) spermine-5-carboxamide. The number of reporter groups, e.g., fluorophores, per polyamine analogue may vary. The maximum number of fluorophores that allows competitive interaction with the PATr is preferred. In the case of monodansylspermine (MDS), the optimal number of fluorophores is one. If the reporter moiety is dansyl, the sensitivity of the assay can be improved by use of an anti-dansyl antibody (Molecular Probes, Eugene Oreg.) during fluorescence measurement (in accordance with the manufacturer's instructions).

Preferred polyamine probes for the PAT assay have the following characteristics: they bind to the PATr, compete with the natural substrate (FIGS. 27 and 28) and are internalized into the cell after such binding (Example XXV). A preferred probe comprises a fluorophore, a chromophore or a luminescer such as a chemiluminescer or a bioluminescer (*Clin. Chem.* 25:512, 1979) coupled to a polyamine core.

The amount of probe taken up in an assay, or the intracellular localization of the probe are determined by measuring and/or localizing the signal emitted by the reporter moiety after the probe has had the opportunity to bind to the PATr and be taken up. The probe may be a specifically binding ligand or one of a set of proximal interacting pairs.

C. Enzymatic Polyamine Transport Screening Assay

1. Enzymatic Enhancement ELISA

Another preferred approach to a sensitive screening assay uses the enzymatic amplification of the signal emitted by the detectable label on the polyamine probe. A more specific example is a cofactor-labeled probe which can be detected by adding the enzyme for which the label is a cofactor and a substrate for the enzyme. Such an enzyme is preferably one which acts on a substrate to generate a product with a measurable physical property such as color. Examples of such enzymes are listed below.

2. Polyamine Immobilization for Enhanced Detection

Figure 29:
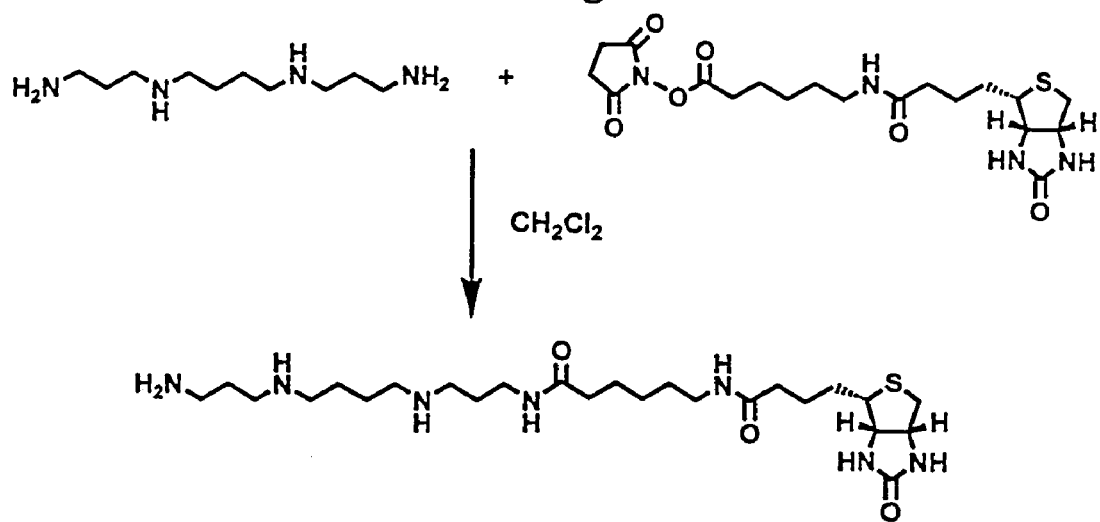
FIGS. 29 and 30 describe the synthesis of a biotin modified polyamines $N^{1-}$[($N^6$-(biotinyl)-6-aminocaproyl)]spermine and $N^1$-(biotinyl)spermine.
Figure 30:
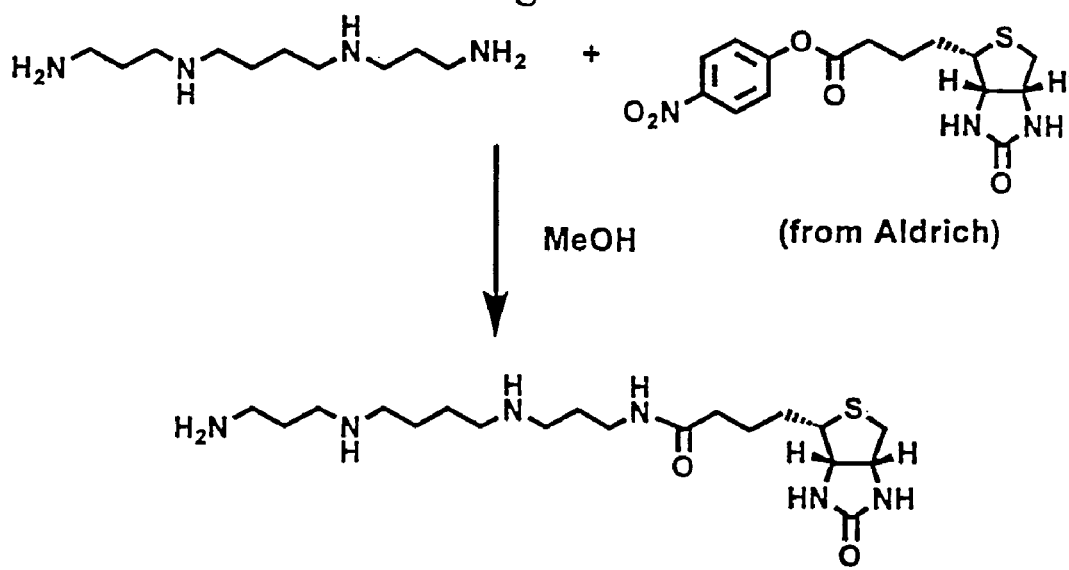

A preferred example of an enzymatically enhanced assay may be done by exploiting the biotin/streptavidin system (see FIG. 31). A biotinylated polyamine such as spermine is prepared, for example, as shown in FIGS. 29 and 30. The PAT assay is performed as described above except that the probe in the appropriately lysed cells is detected using one of the formats described below. For example, after allowing cells to transport a biotinylated polyamine (e.g. $N^1$-biotinyl-spermine), the cells are lysed and the lysate filtered through negatively charged microplate membranes which retain the positively charged polyamine. After washes and appropriate blocking of unreacted sites with a protein such as albumin, the membranes are incubated with a streptavidin-enzyme conjugate and washed. The membranes are treated with a chromogenic substrate of the enzyme and incubated for a set time after which the color signal is read in a spectrometer.

Figure 32:
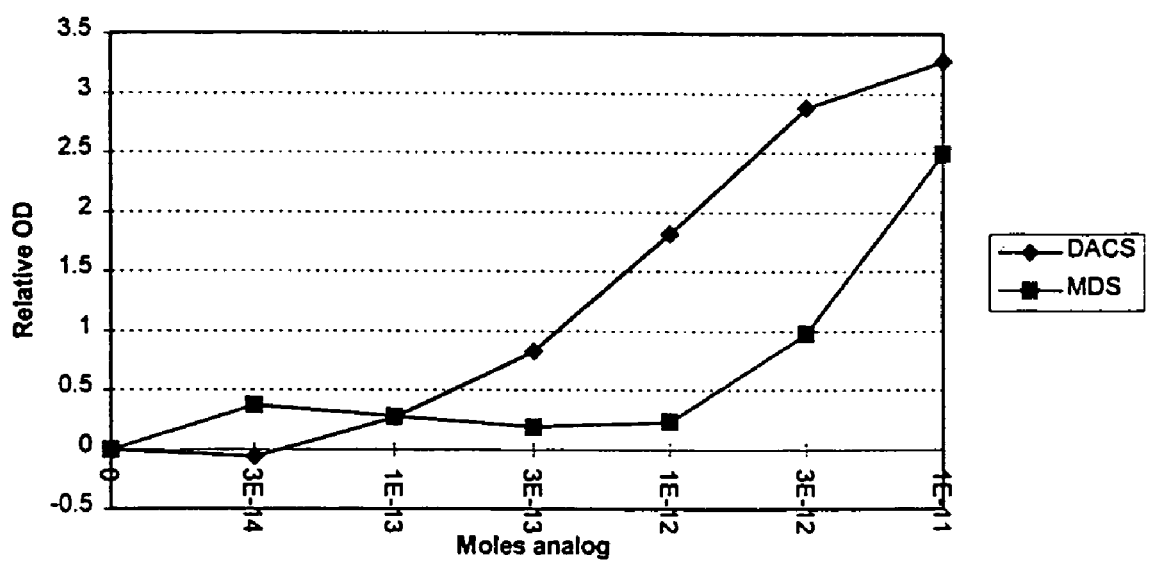
FIG. 32 is a graph showing the detection of N1-dansyl-spermine and DACS using the enzymatic detection system

Colorimetric, fluorescent and chemiluminescent substrates are compatible with this procedure. In another embodiment, the lysate is reacted with a polylysine-treated plate using glutaraldehyde to crosslink the polyamine analogue to the plate. The Schiff base is then reduced to produce an immobilized ligand or analogue such as DACS. The ligand can then be detected through the appropriate reporter system. In the case of DACS, the reporter is detected by anti-dansyl IgG antibody coupled to an anti-rabbit IgG conjugated to an HRP (horse radish peroxidase) detection system (FIG. 32; Example XXVI). In another embodiment, a fraction obtained from the lysate, for example using Sepharose S or Cibacrom Blue, is used.

The advantages of this procedure are (1) the immobilization of the biotinylated spermine to the membrane allows the removal of interfering compounds through washes, and (2) the amplification through enzyme- or antibody-coupled reporter systems increases sensitivity compared with single labeled substrates. The increased sensitivity requires fewer cells per assay. The microtiter plate format allows for rapid HTS.

An additional embodiment of the enzymatically enhanced assay is the use of an antibody to the reporter moiety such as the hapten 2,4-dinitrophenyl group (DNP), 2,4,6-trinitrophenyl (TNP), or, preferably, dansyl. Alternatively, the polyamine can be conjugated with different hapten groups (other than biotin). In the case of biotinylated spermine derivatized with dansyl, after transport into the cells and cell lysis, these molecules are immobilized to streptavidin-coated microplate wells and washed. An antibody specific for dansyl is allowed to bind to any dansyl groups which have become immobilized. The immobilized antibody is then allowed to react with a second antibody (an anti-immunoglobulin specific for the anti-dansyl antibody) conjugated to an enzyme. After the second antibody has been allowed to bind to the immobilized complexes, a chromogenic substrate for the enzyme is added for a set interval. The evaluation of the enzyme-generated signal (color reaction) is a measure of the amount of polyamine bound to the PATr.

The foregoing enzymatic assays are in principle, similar to well-known enzyme immunoassay or enzyme-linked immunosorbent assay (ELISA). See, for example, Butler, J. E. (ed.) *Immunochemistry of Solid Phase Immunoassay*, CRC Press, Boca Raton, 1991; Van Regenmortel, M. H. V. (ed) *Structure of Antigens*, Vol. 1 (CRC Press, Boca Raton 1992, pp. 209–259). Butler, J. E. et al., *J. Immunol. Meth.* 150:77–90, 1992; Maggio, E. (ed.), Enzyme Immunoassay, CRC Press, Boca Raton, Fla., 1980). Enzymes which can be conjugated to the streptavidin or antibody include, but are not limited to, horseradish peroxidase, alkaline phosphatase, glucose-6-phosphate dehydrogenase, malate dehydrogenase, staphylococcal nuclease, Δ-V-steroid isomerase, yeast alcohol dehydrogenase, α-glycerophosphate dehydrogenase, triose phosphate isomerase, asparaginase, glucose oxidase, β-galactosidase, ribonuclease, urease, catalase, glucoamylase and acetylcholinesterase.

Immobilization of a Second Head Group for Enhanced Detection

In another embodiment, the biotin-spermine-hapten (preferably dansyl) molecules are captured using an immobilized anti-dansyl antibody. In this instance, two reporter molecules must be coupled to the polyamine analogue as in FIG. 31. One reporter is used for immobilization such as to an antibody-containing bead (or other solid support) to enable the washing away of excess probe. The other reporter is used for sensitive detection. Streptavidin conjugated to an enzyme or streptavidin followed by enzyme-conjugated anti-streptavidin is preferred for signal amplification/detection.

The linker between biotin and the polyamine is important. It should be designed to maximize binding with steptavidin after the polyamine-biotin has been immobilized to the solid support (*Affinity Chromatography: Principles and Methods*, Pharmacia, 1993). A number of different linker molecules, generally commercially available, can be introduced between the polyamine and biotin, e.g., biocytin. Many different linkers of varying lengths are known in the art. The same considerations are important for ligands/labels other than biotin.

Assays of Other Pharmacological Targets Using Polyamine Probes

The present invention may also be used for histochemical or cytochemical localization of polyamines after uptake. The polyamine analogues described herein localize within the cell. Probes of this type can therefore be used in cytochemical analyses of cells or tissues to identify cells or sites within cells with abnormally high or low levels of polyamines. $N^1$-dansylspermine was shown to localize specifically to the nucleoli and the nuclear membrane (Example XXVI). The structure of the nucleus is a known indicator for the staging of progressing cancer. The present fluorescent probes can be incorporated into traditional cytological analysis with the use of a fluorescence microscope to enhance the accuracy of current diagnostic techniques.

In addition to the PAT activity assay, the reporter probe can be used to quantitate the binding of polyamines to known polyamine targets and binding sites. These sites include the NMDA receptor, $K^+$ inwardly rectifying channel (IRK), protein kinase CK2, and phospholipase C$\delta$1. Polyamines also bind specifically to RNA and DNA, and polyamine interactions play a role in hypusine synthesis. Due to the ease of developing modified polyamine analogues as described herein, specific analogues can be developed for each polyamine binding target.

Soluble Proteins that Bind Polyamines

Many proteins bind polyamines. Assays for such proteins are included in the scope of this invention and can identify drug candidates by competition assays using a bound fluorescent polyamine. In addition a tightly or irreversibly binding polyamine analogue can be used to extract and isolate any polyamine-binding protein or other polyamine-binding target of interest. Some proteins undergo conformational changes when a substrate or a polyamine is bound. The present screening assays are adapted so that the probe either binds or does not bind to a protein when the latter is in a given conformational state. One example is Protein Kinase A2, an isozyme that, upon bindin polyamine, undergoes a conformational change that modulates the enzyme's substrate binding site. An isozyme of methionine adenosyltransferase (MAT2) that comprises only the a subunit is much more sensitive to polyamine inhibition than the isozyme having the $\alpha$ and $\beta$ subunits.

Testing Inhibitors of Polyamine Transport

Through screening compounds made by the various synthetic routes described above, several compounds were found to effectively inhibit polyamine transport. DACS 4 is one such compound, with a $K_i$ 10 nM. To reinforce its effectiveness as a PAT inhibitor, DACS was tested as an inhibitor of cell growth (FIGS. 22–24; Example XIX) in the presence of polyamines or an ODC inhibitor, DFMO. R values were calculated as the ratio of the $IC_{50}$ in the absence of DFMO over the $IC_{50}$ in the presence of DFMO (Example XX). Using both a kinetic measure and a biological assay, the present inventors observed high correlation between the inhibition of PAT and growth. The three compounds 6, 4 and 5 in FIG. 2 (Example XX) had the best combination of $K_i$'s (5, 10 and 10 µM, respectively) and R values (220, 400 and 210, respectively) as summarized below:

| Inhibitor | Ki (µM) | R |
|---|---|---|
| 6 | 5 | 220 |
| 4 | 10 | 400 |
| 5 | 10 | 210 |

Several other compounds unrelated to polyamines were shown to inhibit PAT by a non-competitive mechanism. These compounds (FIG. 25) include several anti-psychotic drugs (trifluoperazine and thorazine). Compounds 161 and 162 had PAT inhibitory activity (see Example XXII). Compound 163, previously shown to be a PAT inhibitor, is also and antipsychotic drug.

Figure 26:
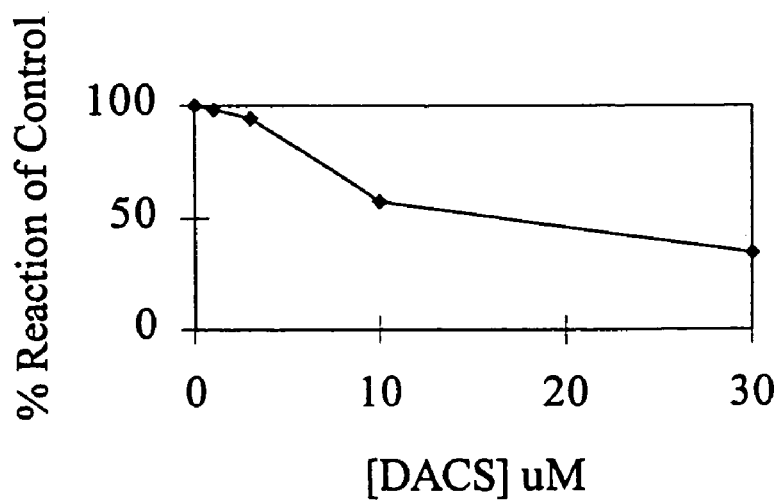
FIG. 26 is a graph showing the inhibition of spermidine/spermine acetyltransferase (SSAT) enzymatic activity by DACS.

Example XXI describes the inhibition of spermidine/spermine acetyltransferase enzymatic activity by DACS (FIG. 26). Based on this, some of these compounds, if internalized, may serve a dual purpose.

The effect of various "headless" polyamine analogues were also evaluated and are described in Example XXIII.

Pharmaceutical and Therapeutic Compositions

Preferred compounds for use in pharmaceutical compositions include all of those mono- and di-substituted polyamine compounds described above, most preferably DACS (4) and compounds 5, 171 and 6, primarily in the form of pharmaceutically acceptable salts of the compounds. Pharmaceutically acceptable acid addition salts of the compounds of the invention which contain basic groups are formed where appropriate with strong or moderately strong, non-toxic, organic or inorganic acids in the presence of the basic amine by methods known to the art. Exemplary of the acid addition salts that are included in this invention are maleate, fumarate, lactate, oxalate, methanesulfonate, ethanesulfonate, benzenesulfonate, tartrate, citrate, hydrochloride, hydrobromide, sulfate, phosphate and nitrate salts.

As stated above, the compounds of the invention possess the ability to inhibit PAT or polyamine synthesis, properties that are exploited in the treatment of any of a number of diseases or conditions, most notably cancer. A composition of this invention may be active per se, or may act as a "pro-drug" that is converted in vivo to active form.

The compounds of the invention, as well as the pharmaceutically acceptable salts thereof, may be incorporated into convenient dosage forms, such as capsules, impregnated wafers, tablets or injectable preparations. Solid or liquid pharmaceutically acceptable carriers may be employed.

Preferably, the compounds of the invention are administered systemically, e.g., by injection. When used, injection may be by any known route, preferably intravenous, subcutaneous, intramuscular, intracranial or intraperitoneal. Injectables can be prepared in conventional forms, either as solutions or suspensions, solid forms suitable for solution or suspension in liquid prior to injection, or as emulsions.

Solid carriers include starch, lactose, calcium sulfate dihydrate, terra alba, sucrose, talc, gelatin, agar, pectin, acacia, magnesium stearate and stearic acid. Liquid carriers include syrup, peanut oil, olive oil, saline, water, dextrose, glycerol and the like. Similarly, the carrier or diluent may include any prolonged release material, such as glyceryl monostearate or glyceryl distearate, alone or with a wax. When a liquid carrier is used, the preparation may be in the form of a syrup, elixir, emulsion, soft gelatin capsule, sterile injectable liquid (e.g., a solution), such as an ampoule, or an aqueous or nonaqueous liquid suspension. A summary of such pharmaceutical compositions may be found, for example, in *Remington's Pharmaceutical Sciences*, Mack Publishing Company, Easton Pa. (Gennaro 18th ed. 1990).

The pharmaceutical preparations are made following conventional techniques of pharmaceutical chemistry involving such steps as mixing, granulating and compressing, when necessary for tablet forms, or mixing, filling and dissolving the ingredients, as appropriate, to give the desired products for oral or parenteral, including, topical, transdermal, intravaginal, intranasal, intrabronchial, intracranial, intraocular, intraaural and rectal administration. The pharmaceutical compositions may also contain minor amounts of nontoxic auxiliary substances such as wetting or emulsifying agents, pH buffering agents and so forth.

Though the preferred routes of administration are systemic the pharmaceutical composition may be administered topically or transdermally, e.g., as an ointment, cream or gel; orally; rectally; e.g., as a suppository, parenterally, by injection or continuously by infusion; intravaginally; intranasally; intrabronchially; intracranially intra-aurally; or intraocularly.

For topical application, the compound may be incorporated into topically applied vehicles such as a salve or ointment. The carrier for the active ingredient may be either in sprayable or nonsprayable form. Non-sprayable forms can be semi-solid or solid forms comprising a carrier indigenous to topical application and having a dynamic viscosity preferably greater than that of water. Suitable formulations include, but are not limited to, solution, suspensions, emulsions, creams, ointments, powders, liniments, salves, and the like. If desired, these may be sterilized or mixed with auxiliary agents, e.g., preservatives, stabilizers, wetting agents, buffers, or salts for influencing osmotic pressure and the like. Preferred vehicles for non-sprayable topical preparations include ointment bases, e.g., polyethylene glycol-1000 (PEG-1000); conventional creams such as HEB cream; gels; as well as petroleum jelly and the like.

Also suitable for topic application are sprayable aerosol preparations wherein the peptide, preferably in combination with a solid or liquid inert carrier material, is packaged in a squeeze bottle or in admixture with a pressurized volatile, normally gaseous propellant. The aerosol preparations can contain solvents, buffers, surfactants, perfumes, and/or antioxidants in addition to the compounds of the invention.

For the preferred topical applications, especially for humans, it is preferred to administer an effective amount of the compound to an affected area, e.g., skin surface, mucous membrane, eyes, etc. This amount will generally range from about 0.001 mg to about 1 g per application, depending upon the area to be treated, the severity of the symptoms, and the nature of the topical vehicle employed.

The compositions of the invention be given in combination with one or more additional compounds that are used to treat the disease or condition. For treating cancer, the polyamine derivatives are given in combination with antitumor agents, such as mitotic inhibitors, e.g., vinblastine; alkylating agents, e.g., cyclophosphamide; folate inhibitors, e.g., methotrexate, pritrexim or trimetrexate; antimetabolites, e.g., 5-fluorouracil and cytosine arabinoside; intercalating antibiotics, e.g., adriamycin and bleomycin; enzymes or enzyme inhibitors, e.g., asparaginase; topoisomerase inhibitors, e.g., etoposide; or biological response modifiers, e.g., interferon. In fact, pharmaceutical compositions comprising any known cancer therapeutic in combination with the substituted polyamines disclosed herein are within the scope of this invention. Most preferably, the present compounds are administered in combination with a polyamine synthesis inhibitor such as DFMO.

The pharmaceutical compositions of the invention may also comprise one or more other medicaments such as anti-infectives including antibacterial, antifungal, anti-parasitic, anti-viral, and anti-coccidial agents.

Typical single dosages of the compounds of this invention are between about 1 ng and about 10 g/kg body weight. The dose is preferably is between about 0.01 mg and about 100 g/kg body wt. and, most preferably, between about 0.1 mg and about 100 mg/kg body wt. For topical administration, dosages in the range of about 0.01–20% concentration of the compound, preferably 1–5%, are suggested. A total daily dosage in the range of about 1–500 mg is preferred for oral administration. The foregoing ranges are, however, suggestive, as the number of variables in regard to an individual treatment regime is large, and considerable excursions from these recommended values are expected.

Effective amounts or doses of the compound for treating a disease or condition can be determined using recognized in vitro systems or in vivo animal models for the particular disease or condition. In the case of cancer, many art-recognized models are known and are representative of a broad spectrum of human tumors. The compounds may be tested for inhibition of tumor cell growth in culture using standard assays with any of a multitude of tumor cell lines of human or nonhuman animal origin. Many of these approaches, including animal models, are described in detail in Geran, R. I. et al., "Protocols for Screening Chemical Agents and Natural Products Against Animal Tumors and Other Biological Systems (Third Edition)", *Canc. Chemother. Reports, Part 3*, 3:1–112, which is hereby incorporated by reference in its entirety.

Parallel Library Synthesis

Combinatorial Approaches to Polyamines and Analogues

Combinatorial chemistry, a rapidly changing field of molecular exploration, is still in its infancy. For reviews, see Lam, K. S., *Anticancer Drug Des.* 12:145–167, 1997; Salemme, F. R. et al.; *Structure* 5:319–324, 1997; Gordon, E. M. et al., *J. Med. Chem.* 37:1385–1401, 1994; Gallop, M. A. et al., J. Med. Chem. 37:1233–1251, 1994). The pharmaceutical industry, is now realizing that the original approach of the combined synthesis of hundreds to thousands of compounds in one "flask" followed by testing and deconvoluting the results is a tedious process with many pitfalls. The more traditional approach of medicinal chemistry, that is, the synthesis and testing of one compound at a time, yields more reliable and informative results about the SAR around a target. The trend in combinatorial chemistry is therefore toward synthesis of multiple compounds at once, with each in a separate container. Therefore, many have adopted this one-compound/one-well parallel synthetic approach. While many lead compounds have been generated this way, the chemistries do not necessarily lead to a molecule with the necessary drug-like characteristics.

The additional steps of lead optimization followed by incorporation of drug-like characteristics (molecular weight, hydrophilicity/hydrophobicity, transport, metabolism and stability) reduce drug development costs. Therefore it is preferred to pursue novel chemistries whereby the desired characteristics are incorporated into the initial libraries. By decreasing the number of steps between lead identification and production of a new drug candidate, costs can be significantly reduced.

Using parallel synthesis starting with an array of sulfonyl chlorides and polyamines, a library of substituted polyamines can be synthesized. The parallel synthesis of 6 substituted polyamines starting from two different amines and three different acid chlorides is described in detail in Example XV.

Using the appropriate available equipment as many as 24 compounds can be synthesized at the same time on one instrument. Commercially available instruments support high throughput parallel synthesis. Microtiter plate formats for synthesis of 96 compounds at a time are now routine, the 96 multipin technology developed by Chiron Mimotopes PTY LTD (San Diego) being a typical example. This format is especially useful to synthesize polyamine analogues with different length carbon linkers. A combinatorial library synthesized with different polyamines and sulfonyl chlorides is described in Example XVI.

Similarly, commercially available acid chlorides are used in parallel combinatorial synthesis with different polyamines to yield a library of monosubstituted polyamine amides, as described in Example XVII. Substituted ureas are synthesized in parallel by activation of the appropriate (commercially available) amines with p-nitrophenyl chloroformate. The product is then reacted with the commercially available amine to yield the desired substituted ureas as described in Example XVIII. Thousands of substituted carboxylic acids, sulfonic acids, sulfonyl chlorides, acid chlorides and amines are commercially available for coupling (directly or through a linker) to a variety of commercially available amines. Conventional methods can be used for derivatives that are not commercially available. Compounds comprising these libraries are evaluated in high-through-put screening assays for their potency in different disease contexts.

The chemistries described herein are readily applied in combinatorial syntheses using the "one-compound/one-well approach." Examples XVII and XVIII exemplify how this would be done. With this approach, many new analogues are made in a short time so that the desired drug-like characteristics are quickly fashioned.

The present inventors have designed a method to synthesize novel compounds for therapeutic uses and as probes for various assays. Such compounds are useful as drugs in a number of diseases, particularly against cancer. They are also useful as a component in combination drug therapy with, for example, a polyamine synthesis inhibitor such as DFMO (which inhibits ornithine decarboxylase, ODC) or with other agents, thereby providing novel combination chemotherapy regimens. The compounds of the present invention are also useful for treating other diseases or conditions in which polyamines play a role as described above.

Combinatorial Synthesis of Polyamine Analogues

This invention extends the repertoire of chemistries available to explore SARs around drug targets for PAT inhibition and other relevant pharmacological and industrial targets. By combining the versatile and efficient NaBH$_3$CN reductive amination reagent with a soluble (MeO-PEG-OH) or insoluble polymeric support, a powerful combinatorial methodology is provided. Additional important technical innovations include the use of a Boc-like linker that provides the desired polyamines as salts without the problem of additional residue remaining from the linker.

The direction of extension of the polyamine chain also ensures that over-alkylation does not occur while at the same time ensuring high yields. Overalkylation results in di-alkyl side-products (MeO-PEGO-linker-CHO plus excess R—NH$_2$ instead of MeO-PEGO-linker-NH$_2$ plus R—CHO).

Given the particularly mild nature of the chemistry involved, many important and novel structural features can be readily incorporated into the resulting polyamine products, including chiral substituents on the carbon chain (using amino acid derived synthons), heterocyclic substituents, carbohydrates, nucleosides, conformational restraints and, finally, known drugs.

Synthetic Methods

Figure 33:
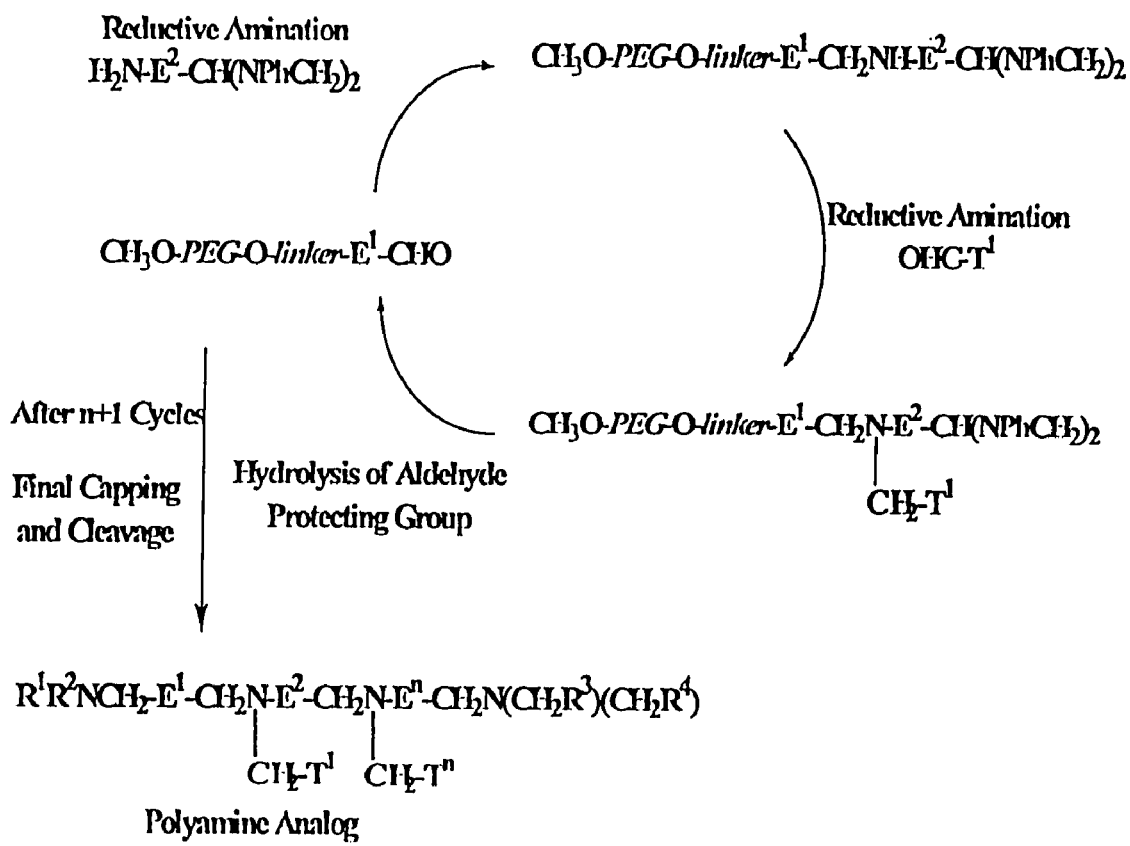
FIG. 33 is a general scheme that brings together the three major components of the present compositions in a synthetic cycle for generating polyamine derivatives.

The synthetic methods bring together the three major components of this novel technology in the synthetic cycle shown in FIG. 33. This includes (1) the use of soluble polymer to anchor the growing chain, (2) extenders and (3) terminators which block the chain extension.

Figure 34:
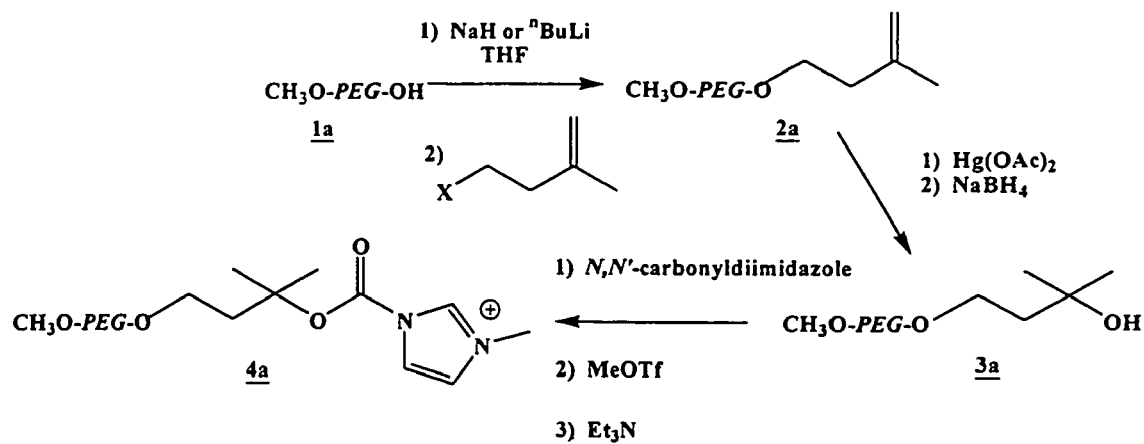
FIG. 34 outlines synthesis of an activated tert-alkoxycarbonyl MeO-PEG polymer which is reacted with a free amino/protected aldehyde extender synthon.
Figure 35:
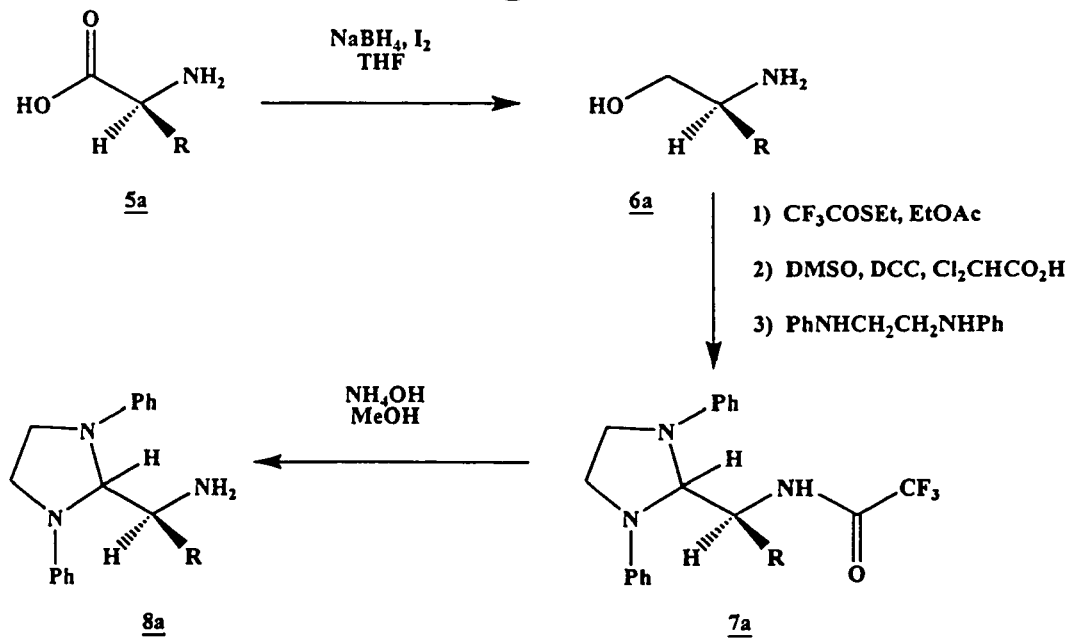
FIG. 35 shows the production of these extenders from either commercially available amino alcohols or the chiral amino acid precursor pool.
Figure 36:
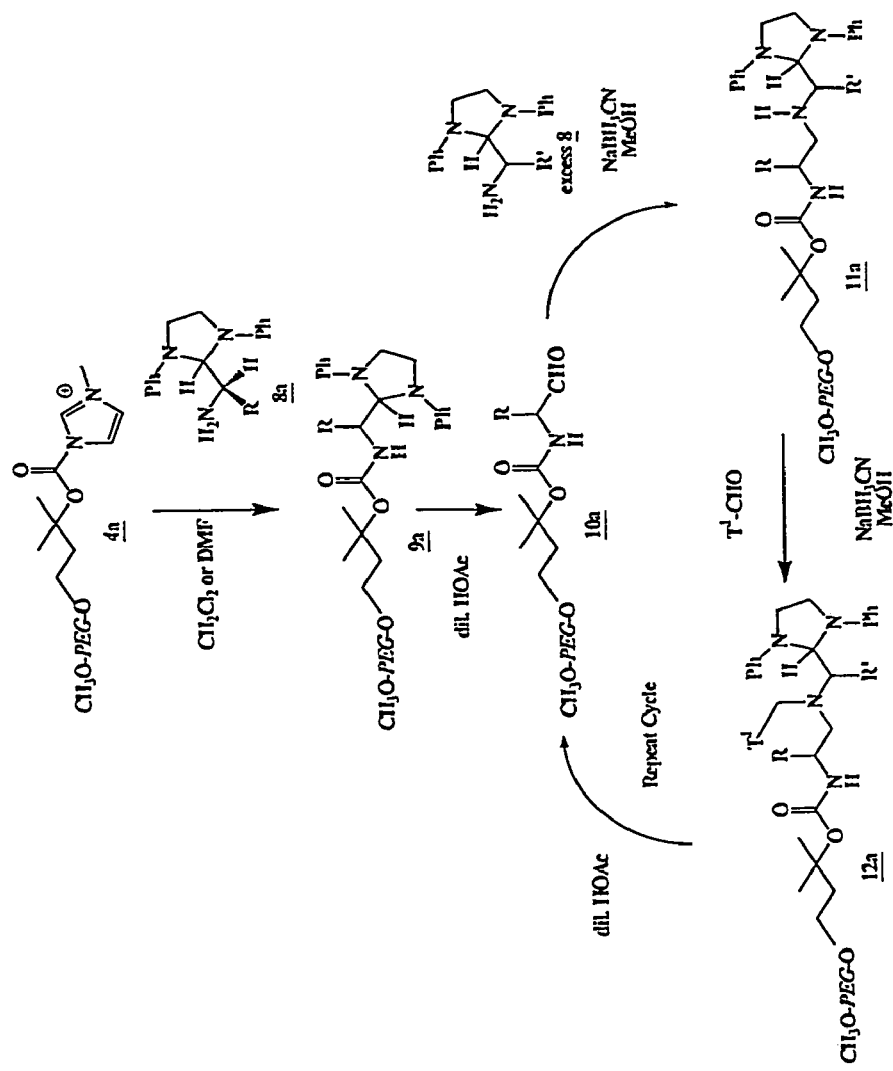
FIG. 36 shows the next step in the synthetic cycle: reductive amination with NaBH$_3$CN is used to initially extend the backbone followed by an additional reductive amination step with an aldehyde to terminate the secondary amine produced.
Figure 37:
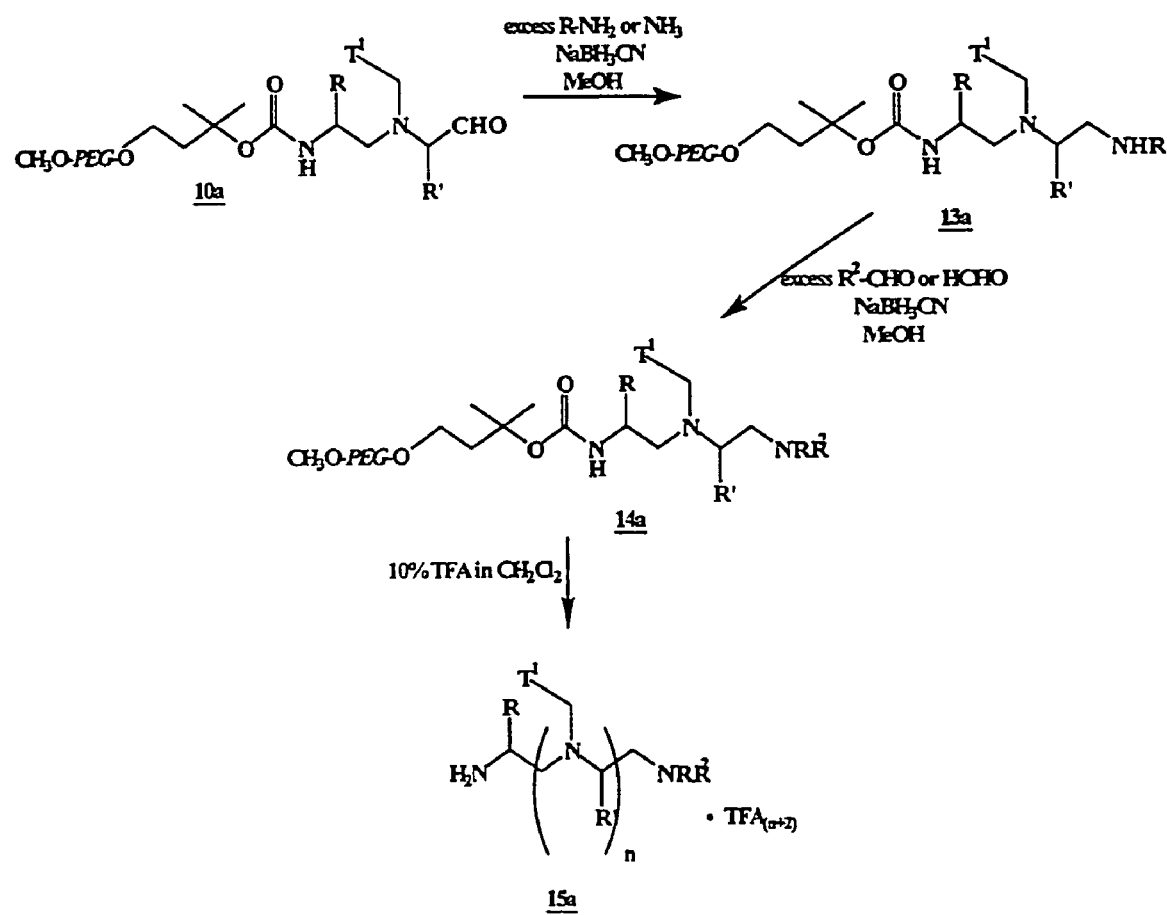
FIG. 37 shows the final steps, including the final capping and the acidmediated cleavage of the product from the polymeric support as the trifluoroacetate salt of the desired analogue.

First, an activated tert-alkoxycarbonyl MeO-PEG polymer is synthesized as indicated in FIG. 34. Second, this polymer is reacted with a free amino-protected aldehyde extender synthon. FIG. 35 depicts the production of these extenders from either commercially available amino alcohols or the chiral amino acid precursor pool. Third, the synthetic cycle is followed using the reductive amination reaction with NaBH$_3$CN initially to extend the backbone followed by an additional reductive amination step with an aldehyde to terminate the secondary amine produced above (FIG. 36). The final steps are the capping and acid cleavage from the polymeric support to provide the desired polyamine analogue as an acid salt (FIG. 37).

1. Activated Polymer

The choice of MeO-PEG-OH (Catalog, Polyethylene Glycol Derivatives. Shearwater Polymers, Inc., 2307 Spring Branch Road, Huntsville, Ala. 35801) as the polymeric support, is one of the key technical innovations of this invention. This material has the unique properties of (a) solubility in most commonly used organic solvents (see Table 1; Bayer, E. et al., *In Proc. Eur. Pept. Symp,* 13th, 129, 1975), and (b) precipitability by the addition of diethyl ether. These properties overcome many of the problems of solid-phase synthesis. For example, it is well known that complete contact between reaction partners, without a solid-liquid phase barrier, greatly increases reaction rates and yields (Lloyd-Williams, P.; *Tetrahedron,* 49:11065–11133, 1993). As seen in Table 1 below, after completion of the reaction, the soluble polymeric product can be precipitated from the reaction medium simply by pouring into diethyl ether. In addition, other solid supports or chips can be substituted.

TABLE 1

Solubility of MeO-PEG-OH 5000 at Room Temperature in Weight Percent

| Solvent | Solubility (%) |
| --- | --- |
| Water | 55 |
| CH$_2$Cl$_2$ | 53 |
| CHCl$_3$ | 47 |
| DMF | 40 |
| Pyridine | 40 |
| CH$_3$OH | 20 |
| Benzene | 10 |
| Ethanol | |
| 60% | 50 |
| 100% | 0.1 |
| 100% at 34° C. | 20 |
| Ethyl ether | 0.01 |

Following filtration, the polymer can be further purified from excess reagents and side-products by recrystallization in absolute ethanol. These unique properties have been exploited by others for other types of libraries. Janda et al. used this resin to produce pentapeptide and arylsulfonamide libraries (Han, M. et al., *Proc. Natl. Acad Sci USA,* 92:6419–6423, 1995; Janda, K. D. et al., *Meth. Enzymol.* 267:234–247, 1996). Krepinsky and coworkers used the same selectively soluble polymeric support to produce structurally complex oligosaccharides (Douglas, S. P. et al., *J. Am. Chem. Soc.* 117:2116–2117, 1995; Krepinsky, J. J, U.S. Pat. No. 5,616,698, 1997). These reports clearly show the feasibility of this support in complicated and lengthy synthetic procedures.

Hodges reported a novel procedure whereby an amine can be linked to Merrifield's polystyrene resin though a tert-alkoxycarbonyl functionality (Hernandez, A. S. et al.; *J. Org. Chem.* 62:3153–3157, 1997). This Boc-like linker has the distinct advantage of allowing complete removal of the linker moiety from the resin by acid treatment in the final cleavage step. Therefore, application of this method in the present invention provides the final polyamine products as acid salts free from the linker residue.

Incorporation of this linker methodology with MeO-PEG-OH is depicted in FIG. 34. Formation of the lithium or sodium salt of MeO-PEG-OH 1a in THF, followed by alkylation with 2-methyl-4-halo (or tosyl)-1-butene, will give the desired alkene ether 2a of the polymer. See (Douglas et al., supra; and U.S. Pat. No. 5,252,714) for examples. Oxymercuration with Hg(OAc)$_2$, followed by reductive demetallation, gives the desired tertiary alcohol 3 (Brown, H. C. et al., *J. Org. Chem.* 35:1844–1850, 1970). The "one-pot" method of Hodges (supra) is then used to activate this resin for reaction with the first amine subunit. Reaction with N,N'-carbonyldiimidazole and 4-N,N-dimethylaminopyridine gives the intermediate (tert-alkoxycarbonyl)imidazole that is activated by methylation with methyl trifluoromethanesulfonate (MeOTf). The excess MeOTf is removed by treatment with Et$_3$N which itself does not react with the activated imidazolide 4.

2. Extender Units

Great flexibility in this technology lies in the choice of starting materials for extender synthesis. As shown in FIG. 35, by selection from the chiral amino acid pool, free amino/protected aldehydes are produced in high yield and purity in several easy steps. Unprotected amino acids 5a can be directly reduced to their amino alcohols by treatment with NaBH$_4$ and I$_2$ (Bhaskarkanth, J. V. et al., *J. Org. Chem.* 56: 5964–5965, 1991). It is anticipated that protection of the amino acid may nevertheless be necessary for the first, carboxylate reduction step, especially with the more complex amino acids. Selective protection of the more nucleophilic amino functionality with a trifluoroacetyl group (using S-ethyl trifluorothioacetate) yields the desired protected amino alcohol 6a (Schallenberg, E. E., Calvin, M., *J. Am. Chem. Soc.* 77:2779–2783, 1955). This protecting group is selected mainly because of the ease of introducing it and cleaving it with mild base. Pfitzner/Moffatt oxidation using dicyclocarbodiimide and dichloroacetic acid in DMSO followed by in situ aldehyde protection as a 1,3-diphenylimidazolidine yields the crystalline fully protected intermediate 7 (Pfitzner, K. E. et al., *J. Am. Chem. Soc.* 87:5661, 1965; Ranganathan, R. S. et al., *J. Org. Chem.* 39, 290, 1974).

Use of this aldehydic protecting group overcomes several problems at once, for example, the often problematic purification of free aldehydes. Many of these 1,3-diphenylimidazolidine 7 compounds are very crystalline and easy to purify (Wanzlick, H. W. et al., *Chem. Ber.* 86:1463, 1953). Simple hydrolysis with aqueous ammonium hydroxide produces the chiral free amine/protected aldehyde extender unit 8.

Commercially available amino alcohols 6a are being used in the sequence of steps in FIG. 35. The amino protection, alcohol oxidation, aldehyde protection and amide hydrolysis steps have been successful using 3, 4 and 5-carbon chain amino alcohols 6a. These synthons 8a enable production of polyamine scaffolds mimicking the naturally occurring putrescine, spermidine and spermine.

3. Synthetic Cycle

With both the activated polymer 4a (FIG. 34) and the extender units 8a (FIG. 35) in hand, the coupling method is ready to be tested and used. The first extender unit 8a is reacted with the activated polymer to give the protected aldehyde linked through a carbamate, 9a (FIG. 36). Selective deprotection of the 1,3-diphenylimidazolidine group from the terminal aldehyde of 9a produces the required starting substrate for the coupling reaction. This hydrolysis, using a weak acid such as acetic acid, poses no difficulties since the Boc-like linker moiety is expected to be cleaved under more strenuous acid conditions such as 10% TFA in CH$_2$CH$_2$. (Moffatt cleaved the 1,3-diphenylimidazolidine of 5'-aldehydic adenosine with Dowex 50 cation exchange resin (H$^+$ form) in the presence of a isopropylidene ketal (a more acid-sensitive group than is a Boc group); (Ranganathan et al., supra).

To optimize yields, other aldehydic protecting groups including acyclic acetals, cyclic acetals or the acid stable dithio acetals may be incorporated into the scheme. The polymeric aldehyde 10a is then reacted with an excess of the next free amine/protected aldehyde subunit 8a (FIG. 35) under the Borch reductive amination conditions in a suitable solvent such as THF or methanol (Borch, R. F. et al., *J. Am. Chem. Soc.* 93:2897–2904, 1971). Reductive amination reactions on solid supports are well-known (Sasaki, Y. et al. *J. Med. Chem.* 30:1162–1166, 1987; Gordon, D. W. et al., *Bioorg. Med. Chem. Lett.* 5:47–50, 1995; Devraj, R. et al., *J. Org. Chem.* 61; 9368–9373, 1996).

Initial imine formation, catalyzed by trace AcOH, followed by addition of NaBH$_3$CN yields the methylene secondary amino product 11a (FIG. 36). The secondary amino function in 11a cannot react further with the excess amine used in the initial imine formation. By using an excess of the free amino extender unit 8a, complete reaction is ensured. Complete reaction is important in any multi-step solid phase synthetic method since lower reaction yields can potentially give complex product mixtures full of undesired species.

By performing the coupling in this synthetic direction with an excess of the amino extender, greater than 98% coupling yields are achieved An excess of the amine greatly increased the yield of the desired secondary amine, based on the aldehyde component. It is expected that different amino/aldehyde reaction partners will react at differing rates. However, by addition of excess amine and by allowing the reaction to proceed for longer times, complete reaction is expected in all cases.

A second reductive amination reaction can now be performed on the resulting, free, secondary amino function of 11a. A wide assortment of commercially available aldehydes are suitable for this reaction, which can "dress" the resulting polyamine scaffold in interesting and novel ways.

A large series of simple straight chain or branched alkyl aldehydes is available. These modified polyamines would have greater lipophilic properties, thus increasing their ability to cross biological membranes and the blood-brain barrier. Any of a large number of unsaturated alkene aldehydes could also be used. A particularly interesting example is acrolein, that can serve as a protecting group thereby allowing return to the secondary amine by deprotection of the resulting allyl amine with Rh(Ph$_3$P)$_3$Cl catalyst (Laguzza, B. C. et al., *Tetrahed Lett.* 22:1483–1486, 1981). An alternative method for secondary amine production is the use of the tBoc group which is cleaved along with the linker in the final reaction.

A wide variety of aromatic aldehydes is also available. Any of a series of substituted benzaldehyde derivatives together with a variety of heterocyclic aromatic aldehydes could be used.

This potential can also be extended to more water soluble derivatives by using carbohydrates and carbohydrate phosphates. With the versatility and mild nature of the coupling chemistry, very complex molecules such as nucleoside aldehydes could also be used to modify these new analogues. The well-known highly avid binding of polyamines to the polyphosphate backbone of DNA and RNA polymers creates the potential for specific, tightly bound polycationic DNA "triple helix" analogues(Dempcy, R. D. et al., *Proc. Natl. Acad. Sci. U.S.A,* 93:4326–4330, 1996; Goodnow, Jr., R. A.

et al., *Tetrahedron Lett.* 38:3195–3198, and 3199–3202, 1997). Such a series would allow analysis of the molecular space surrounding the polyamine targets (described below). With great synthetic flexibility not only in the polyamine scaffold (obtained through choice of the extender units), but also in the range of terminators available to dress the resulting scaffold, it is possible to create great molecular diversity around polyamine analogues.

With the fully terminated and "modified" polyamine in hand, the final capping and cleavage from the polymeric support are performed (FIG. 37). The chemistry of the final capping is again very versatile. By mild deprotection of the 1,3-diphenylimidazolidine 12a (FIG. 36) to produce 10a (FIGS. 36 and 37), and reaction with ammonia under reductive amination conditions, the cleaved polyamine analogue 15a contains primary amino functions at both ends. To create a structure with a secondary amino function at one end, a reaction of the free terminal aldehyde with a primary amine is performed. Reaction with a secondary amine would yield a tertiary amine at the terminal position. Another way of gaining a bifunctional terminal, tertiary amine is by reaction with a primary amine followed by reaction with an aldehydic terminator as above.

Finally, selective modification of either end of the polyamine is achieved by capping the terminus, cleaving from the polymeric support and reacting with an aldehyde. Because this will result in polyamines that are selectively protected at all amino functions from further reaction under reductive amination conditions, the synthetic variability of this approach is virtually unlimited.

4. Analytical and Purification Procedures

Several powerful analytical techniques may be used to follow each of the types of reactions described above. Throughout the synthesis, any intermediate can be analyzed by $^1$H— and $^{13}$C-NMR techniques (Han et al., supra; Janda et al, supra; Douglas et al., supra; Krepinsky et al., supra). The degree of functionalization of the MeO-PEG-OH resin can be analyzed by reaction with phenylisocyanate and UV analysis of the resulting carbamate groups that form on the unreacted polymeric hydroxyl groups. (Analysis of unreacted MeO-PEG-OH (M.W.=5000 daltons) gives an $\epsilon_{236}$ value of 17,500 $M^{-1}$ $cm^{-1}$). Free aldehyde groups are quantified by reaction with 2,4-dinitrophenylhydrazine followed by UV quantification. Free amino groups are quantified by reaction with ninhydrin followed by UV analysis (Kaiser, E. et al., *Anal. Biochem.* 34:595, 1979). Infrared spectroscopy is used for functional group identification. Using the information from these techniques together with weights of the final products after cleavage from the polymer, correlations between the individual analytical methods are made. The final, cleaved products are thoroughly analyzed by standard techniques including: $^1$H— and $^{13}$C-NMR, UV analysis where applicable, IR spectra, melting points, HPLC and TLC retention times and elemental analysis. If these techniques show that further purification is warranted before biological testing, chromatographic techniques such as cation exchange or reverse-phase chromatography are effectively employed for that purpose (Siegel, M. G. et al., *Tetrahedron Lett.* 38:3557–3360, 1997). Examples of compounds synthesized by this approach are shown in FIG. 35.

Solid-Phase Synthesis

The approach outlined above for the liquid-phase synthesis can also be performed using as solid-phase supports polystyrene resins, chip-based systems, multi-pin systems and microwells containing hydroxyl groups. Many solid supports with a hydroxyl linker are available, e.g., the Wang resin (Wang, S.-W., *J. Am. Chem. Soc.*, 95:1128–1333, 1973). Many linkers have been described, and major efforts are under way to design "linker-less" resins that, after cleavage, eliminate the linker to yield the compound of choice.

In contrast to the liquid-based approach, reaction conditions in the solid-phase approach are designed to give optimal yields and minimize side-reactions or incomplete reactions. Therefore, excess reagents are used and are washed away; unwanted reagents are also removable with scavenger resins (Booth R. J. et al., *J. Am. Chem. Soc.* 119: 4882, 1997). Catalytic resins can be used to speed up reactions.

Figure 39:
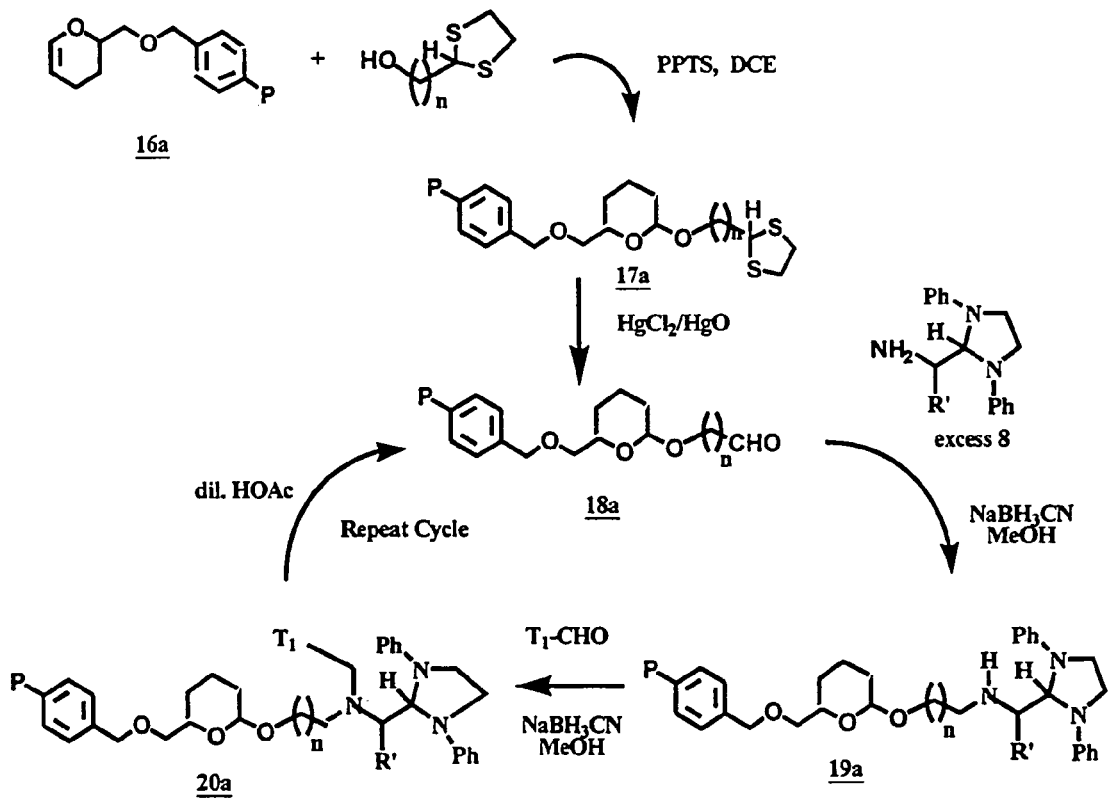
FIG. 39 shows an example of a solid support with alternative linking groups used for solid phase synthesis of polyamine libraries. 3,4-dihydro-2H-pyran-2-yl-methoxymethyl polystyrene is shown.

An example of a solid support with alternative linking group, to synthesize a polyamine analogue is shown in FIG. 39, illustrating 3,4-dihydro-2H-pyran-2yl-methoxymethyl polystyrene 16a (Calbiochem/Novabiochem, La Jolla, Calif.) (Thompson, L. A. et al., *Tetrahed. Lett.,* 35: 9333, 1994). Reaction of 12 with the blocked aminoaldehyde yields 17a which is deblocked with HgCl2/HgO to aldehyde 18a. Reaction of aldehyde 18a with a blocked aminoaldehyde in the presence of NaBH$_3$CN yield 19a with an extended chain containing a secondary amine which blocked with a terminator aldehyde to yield 19a. Compound 19a can either be deblocked and cleaved from the resin to yield a product or can be reacted in a next cycle. The desired product containing a hydroxy-tail is released from the resin by treatment with 95% TFA/5% H$_{20}$.

The multipin-method is based on a modular 8×12 matrix of dimensionally stable polypropylene/polyethylene pins to which a graft polymer is covalently linked. Synthesis is performed upon the graft polymer, which can be varied to suit the application. Examples of multipin systems (Chiron Mimotopes, San Diego, Calif.) containing different linker groups are shown in FIG. 40. The Rink amide linker is shown as structure 23a coupled to the pin P (Rink H., *Tetrahed Lett.,* 28:1787–1790, 1987). This linker requires the removal of the Fmoc protecting group prior to use. The desired product is then synthesized by building it out from the free amino group. After completion of the synthesis the product can be cleaved using 5% TFA/CH$_2$Cl$_2$ to give primary amides. This group is stable to weak acid and base. Pins with structures 23a and 25a are used primarily for coupling carboxylic acids. The stability of 23a s good, and it is only labile to strong base and is cleaved with 95% TFA/H$_2$O. In contrast 25a is stable to strong base and is cleaved with 95% TFA/H$_2$O (Valerio, R. M. et al., *Int. J. Peptide Protein Res.* 44:158–165, 1994). Structure 24a, is used to couple acids which can be cleaved with either NaOH or NH$_2$R to give amides. This pin type can be used in the presence of HF, TFA and weak base. Structure 27a performs similarly to 25a, but is more suitable for milder acids and is generally more labile (Bray, A. M. et al., *J. Org. Chem.* 59:2197–2203, 1994). Structure 26a is used to couple carboxylic acid, is cleaved following alkylation with CH$_2$N$_2$ with NaOH or NH$_2$R (to give amides) and is stable to strong acid and strong bases prior to alkylation. It will be evident to those skilled in the art that these solid supports can be incorporated in the approaches described above. In addition, other solid supports known in the art can be combined with known chemistries to generate polyamine analogues containing different functional groups determined by the particular cleavable linker used.

Having now generally described the invention, the same will be more readily understood through reference to the following examples which are provided by way of illustration, and are not intended to be limiting of the present invention, unless specified.

EXAMPLE I

Synthesis of $N^1$-dansylspermine 3

Figure 7:
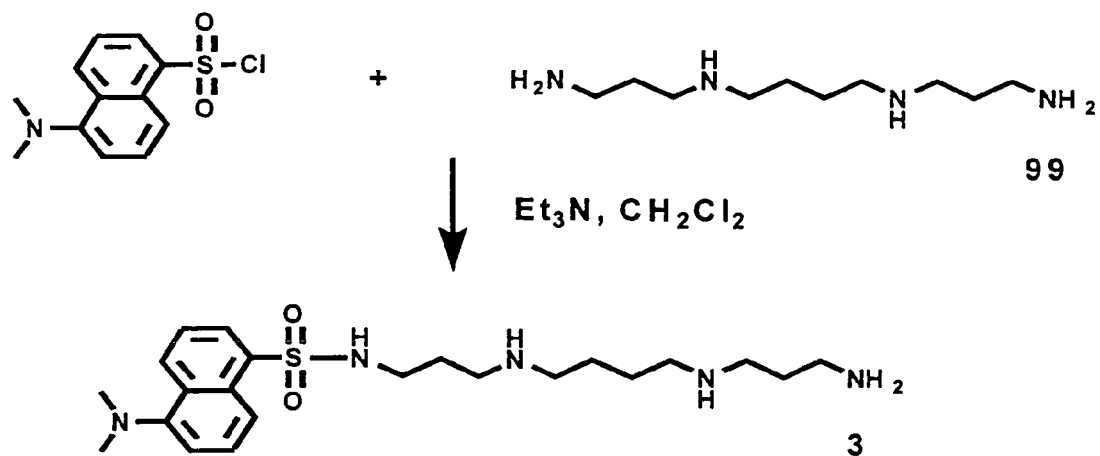
FIG. 7 shows a scheme of the synthesis of the synthesis of $N^1$-dansyl-spermine 3 (MDS).

Synthesis of $N^1$-dansylspermine is illustrated in FIG. 7. To 0.81 g (4 mmole) of spermine and 0.1 g (mmole) of triethylamine in 30 ml dry $CH_2Cl_2$ cooled down to 4C, was added dropwise 0.27 g (1 mmole) dansyl chloride dissolved in 20 ml dry $CH_2Cl_2$ over 90 minutes. The temperature was allowed to rise to ambient temperature and was stirred for 16 hours when it was filtered to remove triethylamine hydrochloride. The precipitate was washed with 25 ml $CH_2Cl_2$ and the combined $CH_2Cl_2$ extracts was extracted with 2×25 ml 5% $Na_2CO_3$ and 1×25 ml water. The $CH_2Cl_2$ was filtered through Whatman no 1 filter paper and evaporated to dryness to yield 0.45 g. Thin layer chromatography on silica gel in isopropanol:pyridine:acetic acid:water (4:1:1:2) showed no starting spermine and mainly two spots, when sprayed with 0.2% ninhydrin/ethanol. The material was dissolved in 8 ml 1.0 M ammonium acetate pH 7.4 and was chromatographed on a Biorad 70 weak cation exchanger (1.5×48 cm) using a pH gradient between 1.0 M ammonium acetate and 1.25 M hydrochloric acid over 500 ml with a flow rate of 0.5 ml per minute, collecting 8 ml fractions. Fractions containing a single spot were collected, adjusted to pH 10.5 and extracted with 2×25 ml $CH_2Cl_2$. This $CH_2Cl_2$ fraction was filtered through Whatman filter paper and evaporated to dryness. The solid product was dissolved in ethanol acidified with hydrochloric acid and recrystallized from ethanol to yield 0.14 g of $N^1$-dansylspermine (also termed monodansylspermine or "MDS"). The NMR spectrum confirmed the structure. The products can be purified by recrystallization with out any ion exchange chromatography.

EXAMPLE II

Synthesis of $N^1$-(1-pyrenylsulfonyl)spermine 15

Synthesis of $N^1$-(1-pyrenylsulfonyl)spermine) is illustrated in FIG. 5. To 0.56 g (2.8 mmole) of spermine and 0.069 g (0.69 mmole) of triethylamine in 25 ml dry $CH_2Cl_2$ cooled down to 4° C., was added drop-wise 0.20 g (0.69 mmole) dansyl chloride 1-pyrenesulfonyl chloride dissolved in 20 ml dry $CH_2Cl_2$ over 30 minutes. The temperature was allowed to rise to ambient temperature and was stirred for 16 hours when it was filtered to remove triethylamine hydrochloride.

The precipitate was washed with 25 ml $CH_2Cl_2$ and the combined $CH_2Cl_2$ extracts were evaporated to dryness and dissolved in ethyl acetate which was extracted with twice with 25 ml 5% $Na_2CO_3$ and once with 25 ml water. The ethyl acetate was filtered through Whatman no 1 filter paper and evaporated to dryness to yield 0.26 g.

Thin layer chromatography on silica gel in isopropanol: pyridine: acetic-acid:water (4:1:1:2) showed no starting spermine and mainly two spots, when sprayed with 0.2% ninhydrin/ethanol.

The material was dissolved in 8 ml 1.0 M ammonium acetate pH 7.4/MeOH 1:1 and was chromatographed on a Biorad 70 weak cation exchanger (1.5×48 cm) using a pH gradient between 1.0 M ammonium acetate pH 7.4 and 1.25 M hydrochloric acid/methanol (1:1) over 500 ml with a flow rate of 0.5 ml per minute, collecting 8 ml fractions. Fractions containing a single spot were collected, adjusted to pH 10.5 and extracted with 2×25 ml ethyl acetate. This ethyl acetate fraction was filtered through Whatman filter paper and evaporated to dryness. The solid product was dissolved in ethanol acidified with hydrochloric acid and recrystallized from ethanol to yield 0.10 g of $N^1$-(1-pyrenylsulfonyl) spermine.3HCl. TLC indicated a single component and NMR spectrum confirmed the structure.

EXAMPLE III

Synthesis of $N^1$-((1-carbonyl)-4-(1-pyrenyl)butane) spermine 37

Figure 6:
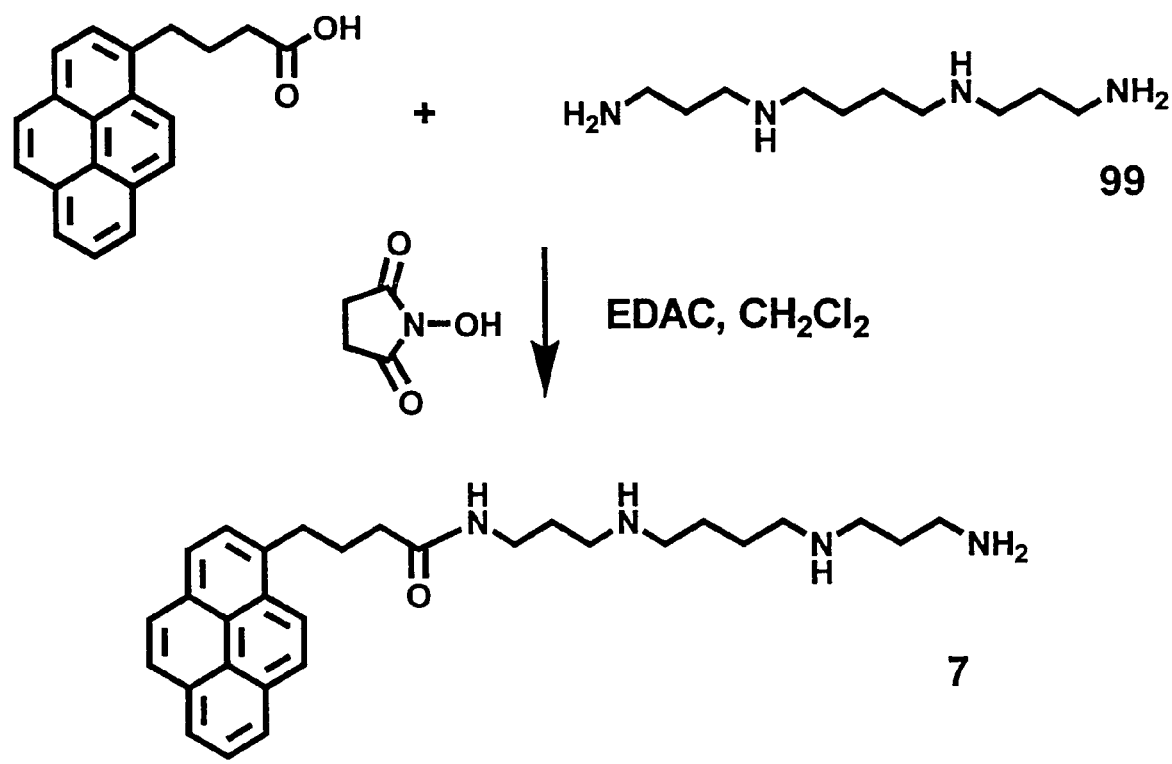
FIG. 6 shows a scheme of the synthesis of $N^1$-((1-carbonyl)-4-(1-pyrenyl)butane)spermine 7

Synthesis of $N^1$-((1-carbonyl)-4-(1-pyrenyl)butane)spermine is illustrated in FIG. 6. To 0.29 g (1 mmole) of 1-pyrenebutyric acid dissolved in $CHCl_3$ with heating were added 0.19 g (1 mmole) of EDC 0.12 g (1 mmole) of N-hydroxysuccinamide and was stirred at room temperature for 30 minutes when this solution was added drop-wise to 0.82 g (4 mmole) spennine dissolved in 20 ml $CHCl_3$. The reaction was allowed to proceed for another 4 hours when it was diluted with an equal volume of ethylacetate. This solution was extracted with 25 ml 5% $Na_2CO_3$ and once with 25 ml water. The organic solution was filtered through Whatman no 1 filter paper and evaporated to dryness to yield 0.25 g.

Thin layer chromatography on silica gel in isopropanol: pyridine:acetic acid:water (4:1:1:2) showed no starting spermine and mainly two spots, when sprayed with 0.2% ninhydrin/ethanol.

The material was dissolved in 8 ml 1.0 M ammonium acetate pH 7.4/methanol 1:1 and was chromatographed on a Biorad 70 weak cation exchanger (1.5×48 cm) using a pH gradient between 1.0 M ammonium acetate and 1.25 M hydrochloric acid/methanol (1:1) over 500 ml with a flow rate of 0.5 ml per minute, collecting 8 ml fractions. Fractions containing a single spot were collected, adjusted to pH 10.5 and extracted with 2×25 ml ethyl acetate. This ethyl acetate fraction was filtered through Whatman filter paper and evaporated to dryness. The solid product was dissolved in ethanol acidified with hydrochloric acid and recrystallized from ethanol to yield 0.13 g of $N^1$-((1-carbonyl)-4-(1-pyrenyl)butane)spermine. TLC indicated a single component and NMR spectrum confirmed the structure.

EXAMPLE IV

N-(1-anthracenyl)-N'-(N1-spermidyl)urea (9)

Synthesis of N-(1-anthracenyl)-N'-(N1-spermidyl)urea is illustrated in FIG. 4. A solution of 1 g of 1-aminoanthracene (5.2 mmole) and 1.04 g p-nitrophenyl chloroformate (5.2 mmole) in 100 ml benzene was refluxed using an air condenser until no more HCl gas escaped as measured with pH paper (3 hours). The desired product, N-(1-anthracenyl)-O-(p-nitrophenyl)urea (1.6 g; 86% yield) was filtered from the cooled reaction and washed with benzene. This product was used without further purification.

To 0.5 g (2.5 mmole) spermine in 30 ml dichloromethane was added drop-wise 0.18 g (0.5 mmole) of the urethane in 20 ml dichloromethane. The reaction was allowed to proceed for 16 hours when it was extracted 2×50 ml 5% $Na_2CO_3$ solution followed by 1×50 ml water. The filtered solution was evaporated to dryness on a high vacuum. The residue was dissolved in MeOH and acidified with 4 equivalents of 6N HCl acid solution. This solution was evaporated to dryness and was then recrystallized from EtOH/MeOH to yield 27.5 mg of compound that showed mainly one spot on silica gel TLC (isopropanol:pyridine:acetic acid:water; 4:1:1:2).

-continued

103

Using known chemistries the chain length can be increased as desired. A preferred length is n=1 to 10.

EXAMPLE VI

N—($N^1$-spermidyl)-2-(naphthoxy)acetamide (104)

The same synthetic is carried out using as starting material (2-naphthoxy)-acetic acid, N-hydroxysuccinimide ester, so that the product is N—($N^1$-spermidyl)-2-(naphthoxy)acetamide as shown below:

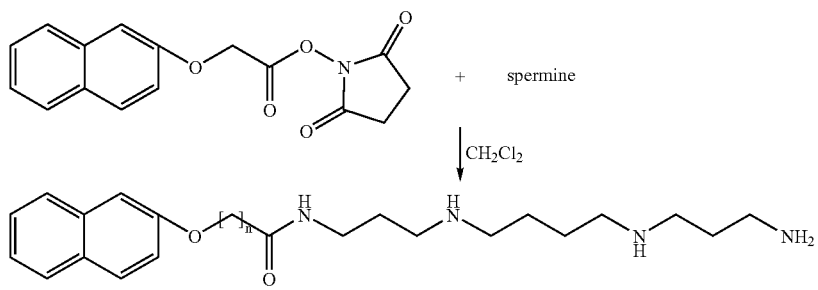

104

Using known chemistries the chain length can be increased as desired. A preferred length is n=1 to 10.

EXAMPLE VII

Synthesis of O-(Fluorenylmethyl)-N—(N1-spermidyl)urethane

A synthetic scheme as described in Example II is carried out using starting compound 9, fluorenylmethyl chloroformate instead of 1-pyrenylsulfonyl chloride as shown below.

EXAMPLE V

Synthesis of N—($N^1$-spermidyl)-2-(naphthyl)acetamide (103)

A synthetic scheme as described in Example IX ??? is carried out, with the difference that the starting compound is 1-naphthylacetic anhydride (instead of N6-(dansyl)-6-aminocaproyl-N-hydroxysuccinimide ester). This yields the product N—($N^1$-spermidyl)-2-(naphthyl)acetamide as shown below:

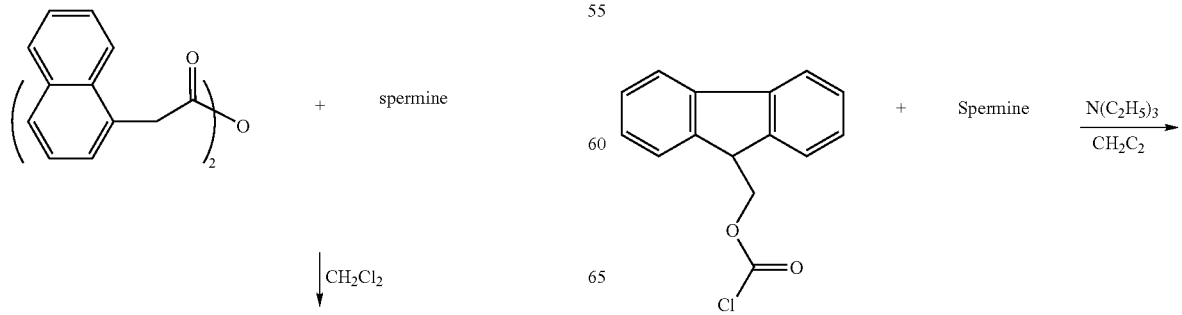

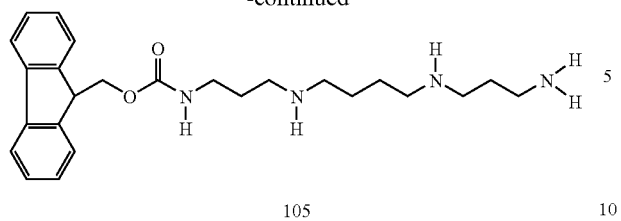

105

EXAMPLE VIII

Disubstituted functionalizable compounds are well known in the art, for example sulfonyl chlorides, benzoyl chlorides, cyanates, thiocyanates, etc. The reaction of 2,6-naphthalene disulfonyl chloride with spermine is shown below.

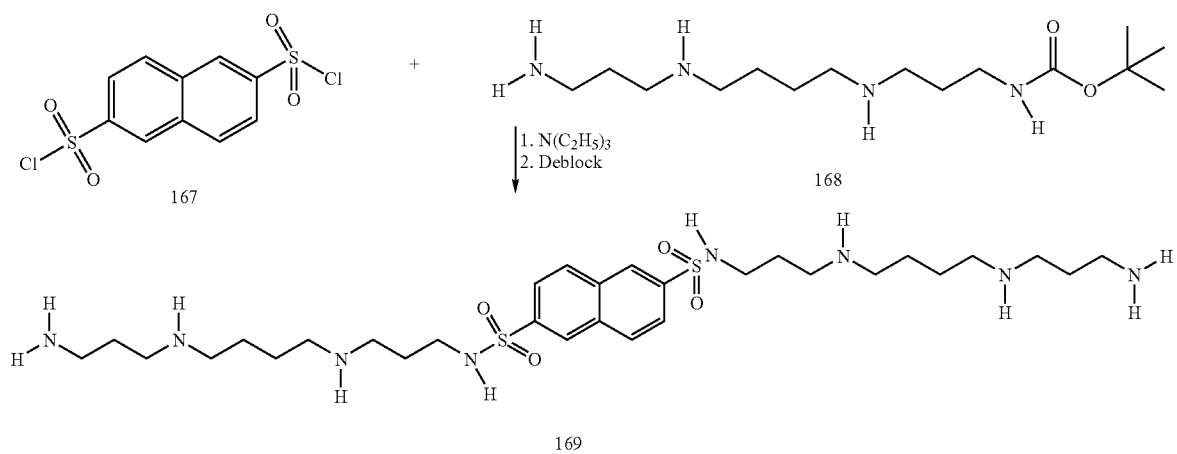

EXAMPLE IX

N$^1$-[(N$^6$-dansyl)-6-aminocaproyl]spermine (DACS 4) by Method 1

Synthesis of DACS by method 1 is illustrated in FIG. 8. The reactants and product are shown below. To 0.55 g spermine (2.7 mmole) in 20 ml dichloromethane cooled in an ice bath was added drop-wise 0.125 g of N6-(dansyl)-6-aminocaproyl-N-hydroxysuccinimide ester (0.27 mmole) dissolved in 10 ml dichloromethane over 30 minutes. The reaction was stirred for 16 hours at ambient temperature when it was filtered to remove precipitate. The filtrate was diluted with 30 ml CHCl$_3$ and was extracted 2×50 ml 5% Na$_2$CO$_3$ solution followed by 1×50 ml distilled water. The organic phase was filtered and evaporated to dryness. The residue (0.20 g) was dissolved in 7 ml methanol and acidified with 5 equivalents of 6N HCl. The solvent was evaporated and the solid was recrystallized from ethanol/methanol gave 0.073 g (39% yield) of the desired product. Silica gel TLC in isopropanol:pyridine:acetic acid:water (4:1:1:2) showed a single fluorescent spot which also gave a ninhydrin positive spot. Nominal mass spectrometry, ion pair reversed phase chromatography and NMR confirmed the identity and purity of the compound.

EXAMPLE X

4-Nitrophenyl 6-(N-(t-butoxycarbonyl)amino)hexonate 108

This compound, illustrated as an intermediate to DACS is shown in FIG. 9. To a dry round-bottom flask was added 11.55 g (50 mmol) of 6-(N-(t-butoxycarbonyl)amino)hexanoic acid 1 (available from NovoCalbiochem), 12.4 g (60 mmol) of dicyclclohexylcarbodiimide and 8.35 g (60 mmol) of 4-nitrophenol. To these solids was added 150 mL of dry EtOAc under argon at r.t. to produce an offwhite heterogeneous suspension. After 3 h at r.t. the solid DCU was filtered off through a pad of Celite and this pad was washed 3× with 50 mL of EtOAc. The combined filtrates were evaporated to give 27 g yellow solid. This was crystallized from 200 mL of abs. EtOH to give 13.54 g (77%) white solid as first crop. TLC (silica gel, CHCl$_3$) Rf0.7. NMR confirmed the identity of the compound.

EXAMPLE XI

4-Nitrophenyl 6-aminohexonate trifluoroacetate salt 109

This compound, illustrated as an intermediate to DACS is shown in FIG. 9. To a solution of 5.0 g (14.2 mmol) of 108 in 30 mL of CH$_2$Cl$_2$ was added 15 mL of trifluoroacetic acid at r.t. Many bubbles formed in the clear reaction solution. After 1 h the solvents were removed under reduced pressure to give a clear oil. This oil was triturated with diethyl ether to form a white waxy solid which was dried under high vacuum. TLC (Rf0.05 in 10% MeOH in CHCl$_3$) showed the product was pure enough for the next step. Yield 5.25 g white solid (100%).

EXAMPLE XII

4-Nitrophenyl 6-(N-(dansyl)amino)hexonate 110

This compound, illustrated as an intermediate to DACS is shown in FIG. 9. To the suspension of 4.2 g (11.5 mmol) of 109 in 50 mL of dry CH$_2$Cl$_2$ was added 3.71 g (13.8 mmol) of dansyl chloride as a solid, followed by 4.8 mL (34.5 mmol) of dry Et3N dropwise through a syringe under argon at r.t. The resulting yellow solution was stirred at r.t. for 18 hr. when the solvents were evaporated to give a green oily solid. This material was dissolved in 250 mL of CHCl$_3$ and washed with 100 mL of 0.1 N HCl, H$_2$O then brine. The organic layer was dried and evaporated to give 5.85 g green oily solid. This was crystallized from 100 mL of abs. EtOH to give 2.136 g (38%) yellow solid from the first crop. The mother liquor can be crystallized for a second crop or purified by column chromatography on silica gel using CHCl$_3$ then 10% EtOAc in CHCl$_3$ for additional pure product. M.p. 84–86 C. NMR confirmed the identity of the compound.

EXAMPLE XIII

N$^1$-[(N$^6$-dansyl)-6-aminocaproyl]spermine (DACS 4) by Method 2

This synthetic method is illustrated in FIG. 9. To a clear solution of 72.8 mg (0.36 mmole) of spermine in 2 mL of MeOH is added 2.0 mL of 0.15 M MeOH solution (0.30 mmol) of 110 dropwise at r.t. After 1 drop was added a very bright yellow color appeared. This yellow solution was stirred for 15 min. when the solvent was evaporated to give 220 mg of a yellow, oily solid. The crude product was dissolved in 1.0 mL of 0.5 M HCl and applied to a 1×36 cm column of C-18 RP silica gel (Bakerbond #7025–01) in 20/80 MeOH:0.5 M HCl. Elution with the same solvent gave 79 mg (38%) pure hydrochloride salt as a white solid. TLC using 4/1/1/2 isopropanol:acetic acid:pyridine:H$_2$O gives an Rf of 0.70 for DACS, 0.90 for diacyl side product and 0.18 for spermine. NMR confirmed the identity of the compound.

EXAMPLE XIV

N$^1$-[6-aminocaproylspermine] 171

This reaction scheme is carried out as described in detail below.

To a clear solution of 125 mg (0.62 mmol) of spermine in 5.0 mL of MeOH was added a suspension of 181 mg (0.52 mmol) of 3 in 5.0 mL of MeOH. The resulting bright yellow solution was stirred at r.t. for 15 min. when the solvents were evaporated. The resulting yellow solid was dissolved in 10 mL of H$_2$O and applied to 1×30 cm column of BioRex 70 (NH$_4^+$ form) resin. Elution was performed by a linear gradient of 0 to 1 N NH4OH. The product containing fractions were evaporated to give 181 mg of N-t-Boc intermediate that was contaminated with 4-nitrophenol. This material was dissolved in 3.0 mL of H$_2$O and 3.0 mL of 6 N HCl was added at r.t. After 2 h at r.t. the clear solution was extracted 3× with 5 mL of CHCl$_3$, 1× with EtOAc then 1× with CHCl$_3$ again. The aqueous layer was then evaporated to give 220 mg (92%) white solid. NMR confirmed the identity of the compound.

EXAMPLE XV

Parallel Combinatorial Library Synthesis

The general reaction involved in the parallel synthesis is shown in the reaction below:

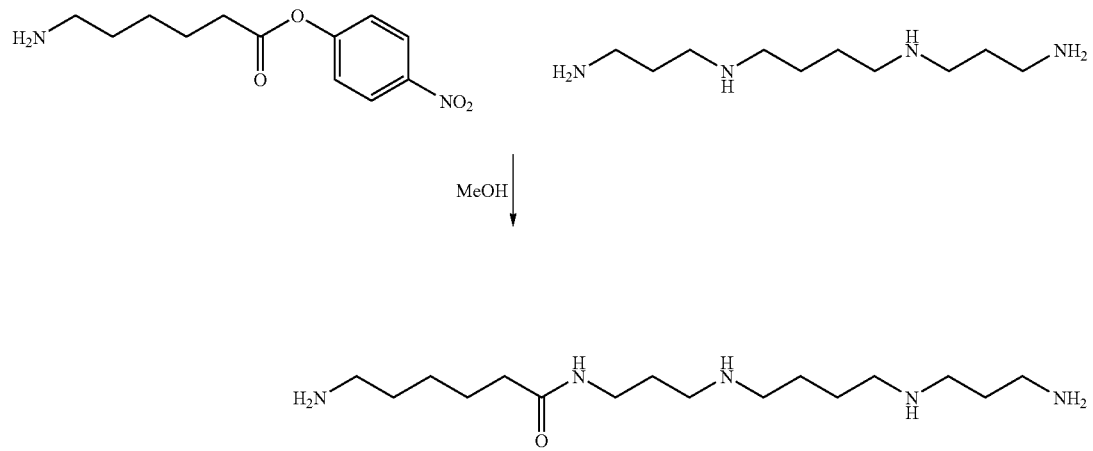

171

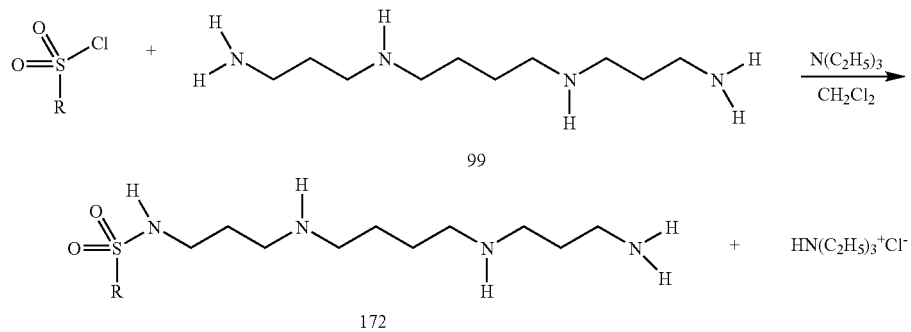

In each of three 10 ml reaction vials (React-Vial™ Pierce, Rockford, Ill.) were placed 0.74 mmol of spermine and 0.5 mmol of triethylamine. Similarly in three additional reaction vials were placed 0.74 mmol of spermine and 0.15 mmol of triethylamine. Similarly in three additional reaction vials were also placed 0.74 mmol of putrescine and 0.15 mmol triethylamine. To each of these flask were added 2.5 ml dry CH$_2$Cl$_2$ and the flasks were closed with a septum and cooled down to −20° C. in a React-block™ aluminum block for 45 minutes, when it was placed in a Reacti-Them™ Heating/Stirring Module, with heating switched off. Three acid chlorides (1-naphthylsulfonyl chloride, 2-naphthylsulfonyl chloride and 10-camphorsulfonyl chloride) in 2.5 ml CH$_2$Cl$_2$ were added dropwise over 15 minutes via a 2.5 ml syringe (All-PP/PE, Aldrich, Milwaukee, Wis.) through the septum to each of spermine and putrescine. Each vial contained also an exhaust consisting of a 2.5 ml syringe filled with anhydrous CaCl$_2$ with out the plunger. The reactions were allowed to proceed for 16 hours at ambient temperature when it was extracted 2×2.5 ml 5% sodium carbonate solution followed by 2×2.5 ml water. To the organic solvents were added 2.5 ml methanol and 5 equivalents of a 6N HCl solution. The solvent was evaporated with argon and dried on a high vacuum. Silica gel TLC with isopropanol:acetic acid:pyridine:water 4:1:1:2 showed mainly one component with either UV/fluorescence or 0.2% ninhydrin in ethanol staining. Purity was estimated as to be greater than 80%. The structures, yield and inhibition of the polyamine transporter is shown in Table 1, below.

EXAMPLE XVI

Parallel Library Synthesis (a)

Using the Reacti-Therm™ Heating/Stirring Module triple module, twenty four 10 ml vials are used at the same time, thereby increasing substantially the number of compounds that can be synthesized in parallel. In addition more than one of these modules can be used at the same time. Using this approach with the commercially available amines listed below and other amines synthesized as described above, libraries of compounds are synthesized with commercially available sulfonyl chlorides (from Aldrich Chemical Company, Maybridge Chemical Company, Ryan Scientific Inc., to name a few) in a manner as described in Example I.

List of Polyamines:

| | |
|---|---|
| N-(3-aminopropyl)-1,3-propanediamine, | N,N'-bis-(3-aminopropyl)ethylenediamine |
| N,N'-bis(3-aminopropyl)piperazine | N,N'-bis(3-aminopropyl)-1,3-propanediamine |
| N,N'-bis(2-aminoethyl)-1,3-propanediamine | Tris(3-aminopropyl)amine |
| Tris(2-aminoethyl)amine | |

TABLE 1

Structures, Yield and Inhibition of the Polyamine Transporter in MDA-MB-231 Cell Line

| Compound | % Yield | Ki μM |
|---|---|---|
|  | 94.6 | 0.19 |

TABLE 1-continued

Structures, Yield and Inhibition of the Polyamine Transporter in MDA-MB-231 Cell Line

| Compound | % Yield | Ki µM |
|---|---|---|
| (naphthalene-1-sulfonyl-NH-(CH$_2$)$_4$-NH$_2$) | 84.8 | >30 |
| (naphthalene-2-sulfonyl-NH-(CH$_2$)$_3$-NH-(CH$_2$)$_4$-NH-(CH$_2$)$_3$-NH$_2$) | 82.6 | 0.15 |
| (naphthalene-2-sulfonyl-NH-(CH$_2$)$_4$-NH$_2$) | 88.8 | 5 |
| (camphor-sulfonyl-NH-(CH$_2$)$_3$-NH-(CH$_2$)$_4$-NH-(CH$_2$)$_3$-NH$_2$) | 59.6 | >10 |
| (camphor-sulfonyl-NH-(CH$_2$)$_4$-NH$_2$) | 79.9 | >30 |

EXAMPLE XVII

Parallel Library Synthesis (b)

A library is synthesized as in Example I, with carboxylic halides in the place of the sulfonyl chlorides, as indicated below. Useful carboxylic halides are commercially available from varies source.

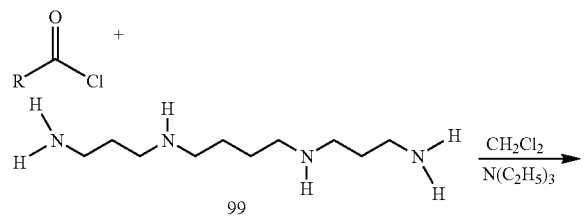

EXAMPLE XVIII

Synthesis of Library of N'-"head group"-N"-(N1-spermidyl)urea

A synthesis of the type shown in Example IV is carried out, with the difference that the starting urethanes are first synthesized in parallel using different aromatic amines as processors.

EXAMPLE XIX

Cell Growth and its Inhibition by Polyamine Analogues

The present investors have developed a growth assay to use in screening for transport inhibitors that are synergistic with ODC inhibitors. The estrogen insensitive human breast carcinoma MDA-MB-231 cell line as the primary cell line in the screen. This cell line, as with many breast cancers, has a high rate of polyamine transport (*Anticancer Res.* (1991) 11:1807–1814). In order to optimize the screen for polyamine transport inhibition, 1.0 µM spermidine was added to media to reverse the effects of ODC inhibitors. The assay was also performed over seven days because this allows for the greatest dynamic range in cell growth due to the mechanism of ODC inhibitors. Cells need to divide several times before the intracellular level of polyamines begin to decrease to growth inhibitory levels. Therefore, growth does not significantly cease until the third to fourth day.

When used to screen for polyamine transport inhibitors, the growth assay alone does not verify a reduction of polyamine uptake. Therefore, the growth assay and a kinetic transport assay have been used to validate transport inhibition.

Figure 22:
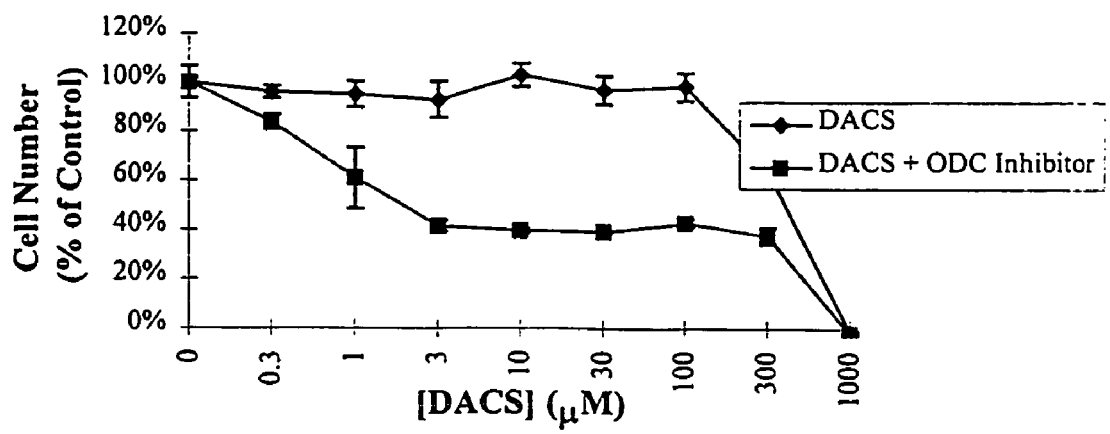
FIG. 22 is a graph showing inhibition of the growth of MDA-MB-231 cells, by DACS in the presence (■) or absence (♦) of the polyamine synthesis inhibitor DFMO. See also, FIG. 2/1–2/10 for the effects of a large number of polyamine analogues on PAT and tumor cell growth. Cells were plated in the presence of varying concentration of DACS with and without 1 mM DFMO. Cells numbers (expressed as % of controls) were determined after 6 days as above.
Figure 23:
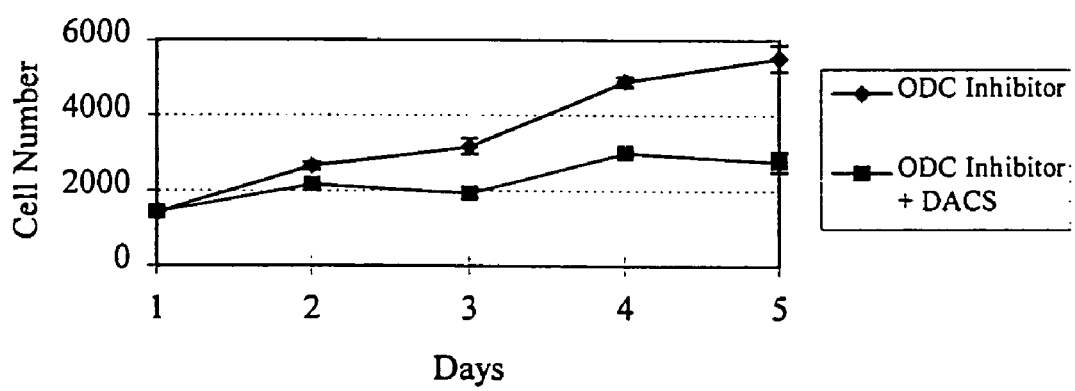
FIG. 23 is graph showing inhibition of cell growth in the presence of 1 µM spermidine.

A. DACS Inhibits Polyamine Transport and Acts Synergistically with ODC Inhibitors Screening of thousands of compounds has permitted the present inventors and their colleagues to identify a transport inhibitor that inhibits spermidine uptake with a $K_i$ of 8 nM, putrescine uptake with a $K_i$ of 5.4 nM and has an $IC_{50}$ of 0.6 µM for growth in combination with an ODC inhibitor (FIG. 22). Over 100 analogues of this compound have been synthesized and SAR data has been accumulating around the structural features necessary to inhibit polyamine uptake. Additional compounds have been discovered with even greater potency than DACS, but not as exhaustively studied as described below. Under the assay conditions described above, with 1.0 λM supplemented polyamines, there is no growth reduction due to ODC inhibition alone. In addition, DACS is not growth inhibitory alone until very high concentrations (300 µM) are reached. DACS makes the previously ineffective ODC inhibitors very effective as growth inhibitors in the presence of polyamines.

Growth inhibition by the combination of DACS and an ODC inhibitor in the presence of polyamines (FIG. 23) mimics the effects of the ODC inhibitor in the absence of significant extracellular polyamines. Growth inhibition began to appear at day 2 and cell growth was reduced 69% by day 3. Growth eventually reached a plateau with the ODC inhibitor combined with DACS but continued in the absence of DACS. This effect appears to be cytostatic in this cell line but, for prolonged periods of time, may be cytotoxic.

B. DACS is Effective in the Presence of Natural Polyamines

Extracellular spermidine, spermine and putrescine can reverse the effects of ODC inhibitors through increased uptake into the cell. The major excreted forms of polyamines ($N^1$-acetylspermine and $N^1$-acetylspermidine) can also reverse the effect of ODC inhibitors. DACS prevents the natural polyamines, putrescine, spermidine, $N^1$-acetylspermine and $N^1$-acetylspermidine, from rescuing the cells from ODC inhibition. This is significant for several reasons. Reports in the literature suggest that there are more than one transporter. If this is true, DACS is effective at blocking the uptake of all of the polyamines at low concentrations.

C. DACS is Effective Against Several Types of Cancers

Figure 24:
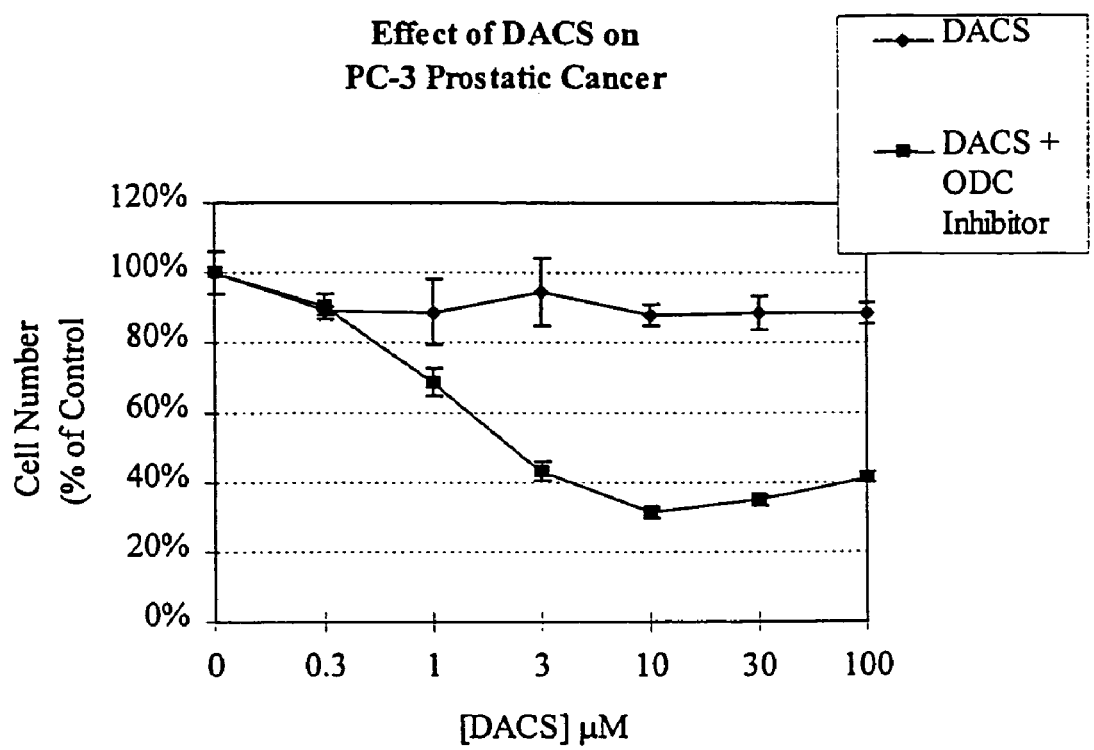
FIG. 24 is a graph showing the inhibition of growth of PC-3 prostate cancer cells by the combination of DACS and DFMO. See description of FIG. 22 for conditions and details.

DACS was tested in vitro in combination with ODC inhibitors against several human cancer cell lines. These include T-cell acute lymphoblastic leukemias (ALL), glioblastomas, prostate, and colon cell lines. DACS is effective against all these tumor cell lines in vitro. FIG. 24 shows the effects of DACS on PC-3 prostate cancer cells.

EXAMPLE XX

Screening of Polyamine Analogues in Transport and Growth Assays

The effect of a number of potential PAT transport inhibitors on PAT and growth of MDA cells is summarized in FIG. 2 (3–98). The ratio, R is the $IC_{50}$ for polyamine alone relative to the $IC_{50}$ for the polyamine analogue combined with an ODC inhibitor. This value of R, indicates the relative level of "synergism" between the polyamine analogue and ODC inhibitor. Under the growth assay conditions, the ODC inhibitor alone shows no inhibition.

EXAMPLE XXI

Transport Inhibitors Inhibit Polyamine-Utilizing Enzymes

A study was conducted to determine whether the compositions of the present invention, designed as PAT inhibitors, had other activities on the PA system. Specifically, the ability of DACS to inhibit an enzyme involved in PA recycling was evaluated. The method used was as described in Casero, R. A. et al., *Biochem. J* 270:615–620 (1990) hereby incorporated by reference in its entirety. This assay measures the incorporation of $^{14}C$-labeled acetyl CoA into spermidine to form acetylspermidine. Varying concentrations of DACS were added to a reaction mixture containing HEPES buffer, pH 7.8, 1 mM spermidine, and 1 mM $^{14}C$-Acetyl CoA. The product is isolated by binding to phosphocellulose filter paper and the extent of reaction is determined by scintillation counting.

As shown in FIG. 26, DACS inhibited spermidine/spermine acetyltransferase (SSAT) in a dose-related manner.

EXAMPLE XXII

Tricyclic and other Heterocyclic Compounds Can Inhibit Polyamine Transport

Employing the polyamine transport assay described in Example XX, several heterocyclic ring compounds were tested for their activity as inhibitors of transport. The unexpected discovery was made that that several compounds strongly resembling tricyclic antidepressants and antipsychotic agents inhibited polyamine transport. Of the compounds shown in FIG. 25 compounds 161, 162 and 165 inhibited the PAT assay in both A172 and MDA cell lines. Compound 165 acted as a non-competitive inhibitor of PAT with a $K_i$ of 41 nM (for A172 cells) and 500 nM (for MDA cells).

These compounds resembled compounds 163–164 in FIG. 25 which are known antipsychotic and antidepressant drugs. These observations indicate that that compounds of this type modulate polyamine uptake.

EXAMPLE XXIII

Effect of Linker Length or "Headless" Status on Growth Inhibition by Polyamine Analogues Compounds were tested for their ability to inhibit cell growth in the presence of 1 μM spermidine and 230 μM ODC inhibitor for the MDA-MB-231 cells or 1 mM ODC inhibitor for the PC3 cells. Cells were plated and drugs were added as described in Example XIX. "Headless" linkers with carbons of 2 or 3 chain length were ineffective on the MDA-MB-231 breast carcinoma but inhibited growth in the PC3 prostatic carcinoma cells as shown in FIGS. 19 and 20

EXAMPLE XXIV

Evaluation of MDS as a Fluorescent Probe in a PAT Assay

The goal of this experiment was to show that MDS competes with $^3$H-spermidine in a transport assay.

Figure 27:
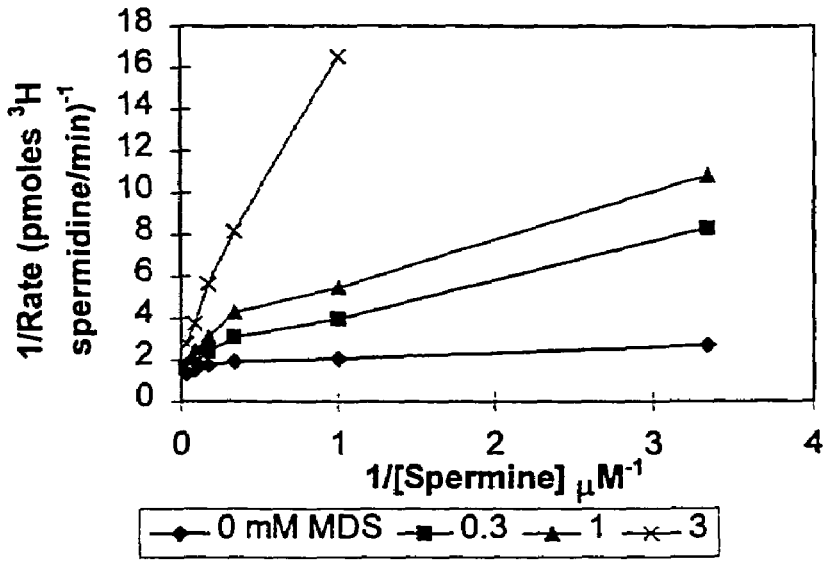
FIG. 27 is a graph showing a comparison of the kinetics of uptake of $N^1$-monodansyl spermine (MDS) with the uptake of radiolabeled spermidine. MDS concentrations were as follows: ♦0 ▲1 µM ■0.3 µM ✱3 µM
Figure 28:
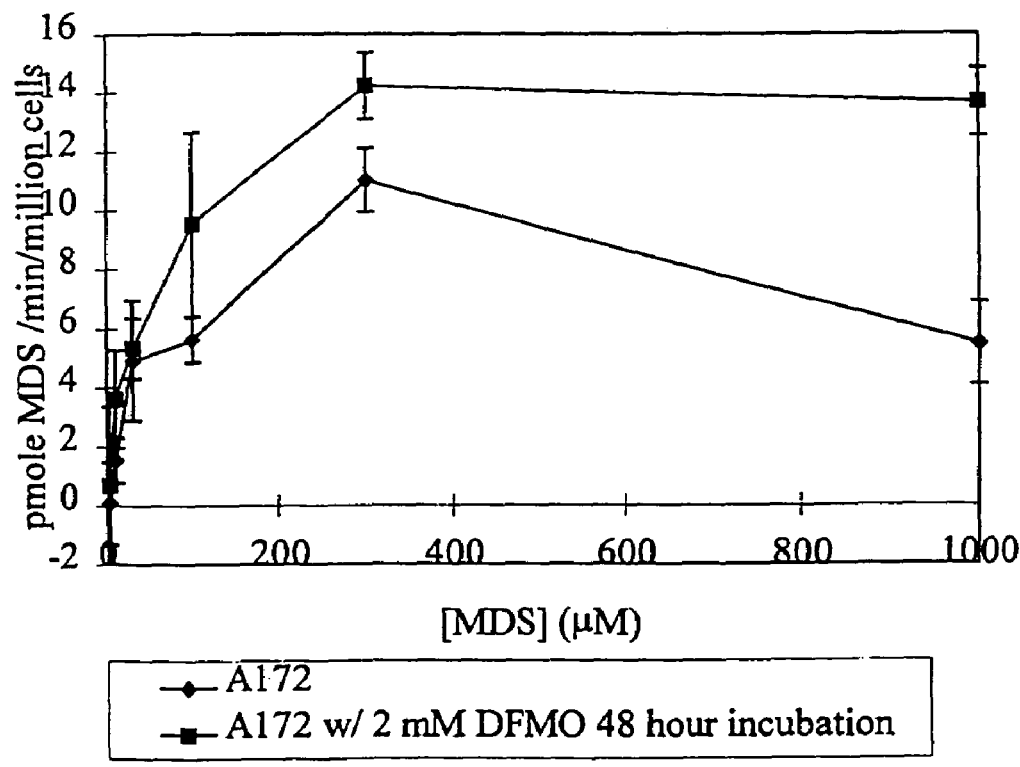
FIG. 28 is a graph showing detection of MDS in the absence of DFMO by fluorescence in A1172 glioblastoma cells.

Using the general radiometric PAT assay and A172 cells as described above, MDS was found to competitively displace $^3$H-spermidine in the transport assay (FIGS. 27 and 28).

EXAMPLE XXV

Fluorescent Microscopic Analysis of Monodansylspermine Uptake

Cells were plated in a sterile chambered slide and grown for 15–48 hours to assure adherence of cells to the slide. The medium was removed and replaced with fresh medium containing 1 μM MDS for a 10 minute incubation period at 37° C. The medium was then removed and the cells washed 3 times with phosphate buffered saline. Glycerol (50% v/v) in a volume of 50 μ was added to the chamber, and the slide was removed and covered with a cover slip.

Using a fluorescence microscope with filters set for excitation at 340 nm and emission at 530 nm, the slide was observed under normal light and with fluorescence. Uptake of the dansylated spermine was observed microscopically and recorded on photograph.

Although a photomicrograph is not included here, cultured cells incubated with MDS took up the labeled material as indicated by the fluorescence which was visualized microscopically. Nucleoli, which contain large amounts of RNA to which the probe could bind, showed particularly strong staining. As expected, the probe was seen lining the membranous structures.

EXAMPLE XXVI

Enzymatic Detection of $N^1$-dansylspermine

Polylysine plates were prepared by addition of 200 μl of polylysine (5 μg/ml) in 10 mM Tris-HCl buffer, pH 8.5, containing 10 mM NaCl and 10 mM NaN$_3$ The plates were incubated for 20 min at 37° C. when the wells were washed 3× with 200 μl water. The plates were then treated with μl of 2.5% glutaraldehyde in 50 mM borate buffer pH 10.0 for 1 hr at 25° C., when the wells were washed with 200 μl of 50 mM borate buffer pH 10.0 twice and once with water. Various concentrations of either N1-dansylspermine or DACS were added to the wells ranging between 0.1 and 10 pmoles/well and incubated for 1 hr at room temperature. The plates were then washed with twice with 200 μl or PBS. The wells were then treated with 200 μl of a 0.3% NH$_4$OH in PBS and was incubated for 1 hr at room temperature when it was washed twice with 200 μl of PBS-0.5% Tween (PBST). The wells were then treated with 200 μl of 0.5% NaBH$_4$ in PBS for 10 minutes when they were washed twice with 200 μl PBST. The wells were then blocked with 200 μl 1% BSA for 1 hour when they were washed once with PBST. Dansyl anti-body (Molecular Probes, Eugene, Oreg.) was added at a 1/200 dilution to each well in 100 μl PBST and incubated overnight at 4° C. when it was washed four times with PBST. To each well was now added 100 μl of anti-HRP antibody at a 1/5000 dilution and incubated for 2 hours at 4° C. when each well was washed four times with PBST. Enzyme activity was determined using either 100 μl of NBT or OPD (5 mg OPD/10 ml of 0.1 M citrate buffer, pH 5.0) and an incubation period of 10 minutes at room temperature. The color was measured at 630 nm in a plate reader.

This method is an alternate embodiment of the of the PAT assay using indirect detection to enhance the signal and lower the detection limits. This method allows for the detection of extremely low concentrations of probe. The results, shown in FIG. 32, indicated that DACS levels as low as 0.1 pmoles could be detected.

EXAMPLE XXVII

Modifications of Polyamine Analogues

Figure 38:
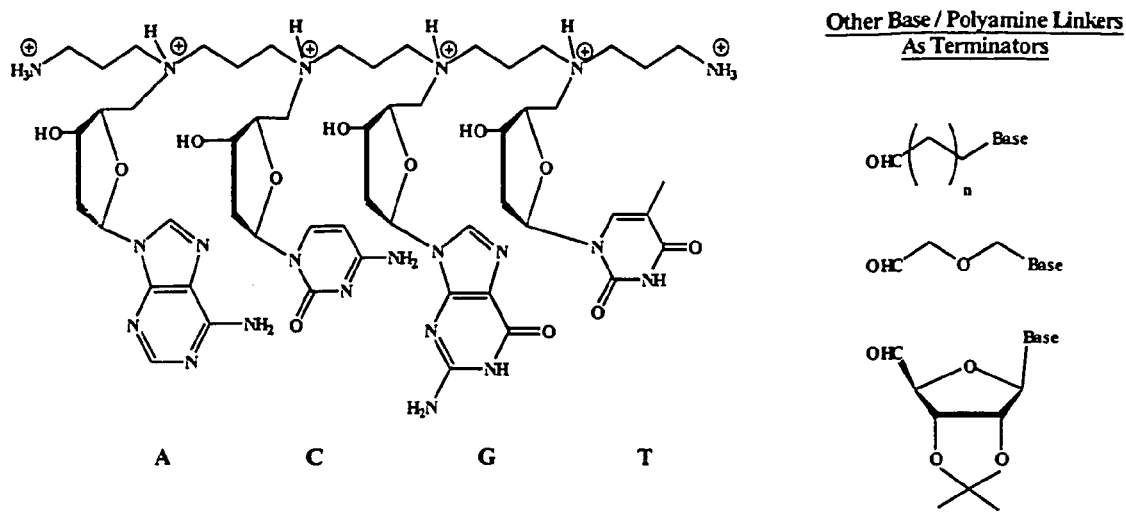
FIG. 38 shows "modifications" of polyamine analogues as they are extended with aldehydic nucleoside terminators. Each amino group can be dressed individually and specifically with any of the four ribonucleosides or 2'-deoxyribonucleosides.

By "modifying" the extending polyamine analogues with aldehydic nucleoside terminators, it is possible to produce sequence specific hybrid oligomers. Each amino group is "modified" individually and specifically with any of the four ribonucleosides (or 2'-deoxyribonucleosides) as shown in FIG. 38.

This technology provides an approach for solving the problem of triple-helix forming antisense oligonucleotides (Chan, P. P. et al., *J. Mol. Med* 75: 267–282 (1997) by combining the transportability of polyamines into cells with structural features of nucleotide sequence specificity. The transport overcomes the limitations of bioavailability while also enhancing the bio-stability of such an oligomer.

EXAMPLE XXVIII

Using the approach outlined in FIGS. 36 and 37, compound 31a (FIG. 39) is synthesized using the blocked 3-aminopropanal 27a, benzaldehyde 28a as the first terminator, the blocked methioninal 29a as an extender and acetone as the final terminator.

EXAMPLE XXIX

A library of compounds is synthesized by using the appropriate blocked aminoaldehydes, aldehydes or ketones. The general structures are shown below.

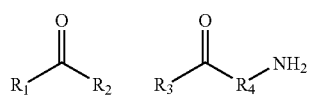

In the case of aldehydes and aminoaldehydes, R1 and R3 are both hydrogen. In the case of ketones and aminoketones $R_1=R_3=H$ or $-(CH_2)_nCH_3$ where n=0 to 6. The ketofunction can also be a part of a ring structure. $R_2$ and $R_4$ can be aliphatic, alicyclic, aromatic and heterocyclic. Examples of compounds that could be contain aldehyde, ketone, amino-aldehyde or amino-ketone functions are dibenzofuran, acridine, 2,1,3-benzothiodiazole, quinoline, isoquinoline, benzofuran, indole, carbazole, fluorene, 1,3-benzodiazine, phenazine, phenoxazine, phenothiazine, adamantane, camphor, piperidine, alkylpiperazine, morpholine, cyclopropyl, cyclobutyl, cyclopentyl, cyclohexyl, cycloheptyl, cyclooctyl, thiophene, furan, pyrrole, alkyl-1,2-diazole, alkylimidazole, alkyl-1H-1,2,3-triazol, alkyl-1H1,2,3,4-tetrazole, thiazole, oxazole, 1,3,4-thiadiazole, pyridinyl, pyrimidine, 1,2-diazine, 1,4-diazine and 1,3,5-triazine, 4-dimethylaminoazobenzene, 2-[1,2-dihydro-2H-1,4-benzodioxepinyl]thiazole, benzene, naphthalene, phenanthrene, anthracene, pyrene, alkanes containing 2 to 10 carbons, alkenes containing 1 to 3 unsaturations and 3 to 10 carbons, alkynes containing 1 to 3 unsaturations and 3 to 10 carbons, branched alkanes, alkenes, alkynes containing 3 to 10 carbon atoms. Many aldehydes, ketones, aminoaldehydes and aminoketones containing one or more of the functional groups listed above, are commercially available. A number of aminoalcohols, precursors for aminoaldehydes are listed in Table 2, below.

TABLE 2

Aminoalcohol Extenders

| | |
|---|---|
| Alinol | 2-amino-2-methyl-1-propanol |
| L-methioninol | D-glucosamine |
| R,S-2-amino-1-butanol | 4-aminobutanol |
| 3-amino-1-propanol | trans--2-aminocy clohexanol |
| 5-aminopentanol | (S)-(+)-2-amino-3-cyclohexyl-1-propanol |
| R,S-2-amino-2-phenylethanol | DL-2-amino-1-hexanol |
| 6-amino-1-hexanol | 1-(1S,2S)(+)2-amino-3-methoxy-1-phenyl-1-propanol |
| 2-amino-3-methyl-1-pentanol | 2-amino-4-methyl-1-pentanol |
| 2-(2-amino-4-nitroanilino)ethanol | D,L-2-amino-1-pentanol |
| 2-aminophenethyl alcohol | 2-amino-1-phenethylethanol |
| 2-amino-3-methyl-1-pentanol | (R)-(+)-2-amino-3-phenyl--1-propanol |
| (S)-(−)-2-amino-3-phenyl--1-propanol | 2-(-3aminophenylsulfonyl)ethanol |
| D,L-1-amino-2-propanol | D,L-2-amino-1-propanol |
| 3-amino-1-propanol | D-galactosamine |
| D-mannosamine | |

EXAMPLE XXX

A library of compounds is synthesized by using the appropriate blocked aninoaldehydes, aldehydes or ketones selected from commercially available sources or from synthetic routes known in the art. Aminoaldehydes are synthesized in a variety of ways from various starting materials such as L- and D-amino acids, aminoalcohols, or alcohols or carboxylic acid substituted with $NO_2$ or —CN groups. Aminoaldehydes are synthesized from appropriately blocked aminoalcohols by known procedures (Larack, R., In: *Comprehensive Organic Transformations*, VCH Publishers. Inc., NY, 1989, pp. 604–616). Aminoaldehydes are directly synthesized from appropriately blocked aminocarboxylic acids or blocked aminonitrile (supra at p. 616–617).

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the invention following, in general, the principles of the invention and including such departures from the present disclosure as come within known or customary practice within the art to which the invention pertains and as may be applied to the essential features herein before set forth as follows in the scope of the appended claims.

The invention claimed is:

1. A polyamine derivative, or salt thereof, wherein said derivative has the formula $R_1$—X—$R_2$,
   wherein $R_1$—X— is of the formula R—NH—CR'R"—CO—,
   wherein —NH—CR'R"—CO— is a D- or L-form of valine, asparagine, or glutamine, or the D-form of lysine or arginine;
   wherein R" is H, $CH_3$, $CH_2CH_3$, or $CHF_2$;
   wherein R is H or a head group selected from the group consisting of a straight or branched $C_{1-10}$ aliphatic, alicyclic, single or multiring aromatic, single or multiring aryl substituted aliphatic, aliphatic-substituted single or multiring aromatic, a single or multiring heterocyclic, a single or multiring heterocyclic-substituted aliphatic and an aliphatic-substituted aromatic; and
   wherein $R_2$ is a polyamine.

2. The derivative of claim 1 wherein R is H.

3. The derivative of claim 2 wherein —NH—CR'R"—CO— is the D-form of lysine.

4. The derivative of claim 3 wherein $R_2$ is spermine.

5. The derivative of claim 4 wherein $R_1$—X— is attached to spermine at the $N_1$ position of spermine.

6. A composition comprising a polyamine derivative or salt according to any one of claims 1–4 and one or more pharmaceutically acceptable excipients.

7. The composition of claim 6 further comprising a polyamine synthesis inhibitor.

8. The composition of claim 7 wherein said inhibitor is difluoromethylornithine (DFMO).

9. The composition of claim 6 wherein said one or more pharmaceutical excipients are suitable for treating a disease or condition in which the inhibition of polyamine transport is desirable.

10. The composition of claim 6 further comprising one or more auxiliary agents or one or more liquid carriers.

11. The composition of claim 10 comprising a preservative or a stabilizer or both as said auxiliary agent.

12. The composition of claim 11 comprising a stabilizer as an auxiliary agent.

13. The composition of claim 10 comprising peanut oil or olive oil as said liquid carrier.

14. The composition of claim 10 further comprising water.

15. The composition of claim 6 formulated as a solid.

16. The composition of claim 15 formulated as a capsule, impregnated wafer, tablet or powder.

17. A method comprising contacting a cell with a polyamine derivative or salt according to any one of claims 1–4.

18. The method of claim 17 wherein polyamine transport in said cell is inhibited.

19. The method of claim 17 wherein said cell is in a subject with a disease or condition associated with undesired cell proliferation.

20. The method of claim 19 wherein said undesired cell proliferation is associated with proliferation of cells of the immune system, cells of the vascular neontima, tumor cells, or with undesired angiogenesis.

21. The method of claim 20 wherein said disease or condition is cancer or post-angioplasty injury.

22. The method of claim 19 wherein said contacting is administration of said polyamine derivative or salt to said subject systemically or topically.

23. The method of claim 19 wherein said contacting is administration of said polyamine derivative or salt to said subject orally, parenterally, transdermally, intravaginally, intranasally, intrabronchially, intracranially, intraocularly, intraaurally, rectally, by infusion, or by injection.

24. The method of claim 23 wherein said administration by injection is intravenous, subcutaneous, intramuscular, intracranial, or intraperitoneal.

25. A method comprising contacting a cell with a polyamine derivative or salt thereof, wherein said derivative has the formula $R_1$—X—$R_2$,
 wherein $R_1$—X— is of the formula R—NH—CR'R"—CO—,
 wherein —NH—CR'R"—CO— is the L-form of lysine or arginine;
 wherein R" is H, $CH_3$, $CH_2CH_3$, or $CHF_2$;
 wherein R is H or a head group selected from the group consisting of a straight or branched $C_{1-10}$ aliphatic, alicyclic, single or multiring aromatic, single or multiring aryl substituted aliphatic, aliphatic-substituted single or multiring aromatic, a single or multiring heterocyclic, a single or multiring heterocyclic-substituted aliphatic and an aliphatic-substituted aromatic; and $R_2$ is a polyamine
 under conditions such that polyamine transport in said cell is inhibited.

26. The method of claim 25 wherein R" and R are H; $R_2$ is spermine; and $R_1$—X— is attached to $R_2$ at the $N_1$ position of spermine.

27. The method of claim 25 or 26 wherein said cell is in a subject with a disease or condition associated with undesired cell proliferation.

28. The method of claim 27 wherein said undesired cell proliferation is associated with proliferation of cells of the immune system, cells of the vascular neontima, tumor cells, or with undesired angiogenesis.

29. The method of claim 28 wherein said disease or condition is cancer or post-angioplasty injury.

30. The method of claim 27 wherein said contacting is administration of said polyamine derivative or salt to said subject systemically or topically.

31. The method of claim 27 wherein said contacting is administration of said polyamine derivative or salt to said subject orally, parenterally, transdermally, intravaginally, intranasally, intrabronchially, intracranially, intraocularly, intraaurally, rectally, by infusion, or by injection.

32. The method of claim 31 wherein said administration by injection is intravenous, subcutaneous, intramuscular, intracranial, or intraperitoneal.

33. A method comprising contacting a cell with a polyamine derivative or salt according to any one of claims 1–4 and a polyamine synthesis inhibitor.

34. The method of claim 23, wherein said inhibitor is DFMO.

35. The method of claim 33 wherein polyamine transport in said cell is inhibited.

36. The method of claim 33 wherein said cell is in a subject with a disease or condition associated with undesired cell proliferation.

37. The method of claim 36 wherein said undesired cell proliferation is associated with proliferation of cells of the immune system, cells of the vascular neontima, tumor cells, or with undesired angiogenesis.

38. The method of claim 37 wherein said disease or condition is cancer or post-angioplasty injury.

39. The method of claim 36 wherein said contacting is administration of said polyamine derivative or salt to said subject systemically or topically.

40. The method of claim 36 wherein said contacting is administration of said polyamine derivative or salt to said subject orally, parenterally, transdermally, intravaginally, intranasally, intrabronchially, intracranially, intraocularly, intraaurally, rectally, by infusion, or by injection.

41. The method of claim 40 wherein said administration by injection is intravenous, subcutaneous, intramuscular, intracranial, or intraperitoneal.

42. The method of claim 25 or 26, wherein said contacting further comprises contacting said cell with a polyamine synthesis inhibitor.

43. The method of claim 42, wherein said polyamine synthesis inhibitor is α-difluoromethylornithine.

44. The method of claim 42 wherein said cell is in a subject with a disease or condition associated with undesired cell proliferation.

45. The method of claim 43 wherein said cell is in a subject with a disease or condition associated with undesired cell proliferation.

46. The method of claim 44 wherein said undesired cell proliferation is associated with cancer.

47. The method of claim 45 wherein said undesired cell proliferation is associated with cancer.

48. The method of claim 19 wherein said undesired cell proliferation is associated with cancer.

49. The method of claim 27 wherein said undesired cell proliferation is associated with cancer.

* * * * *